US011845935B2

(12) United States Patent
Pan

(10) Patent No.: US 11,845,935 B2
(45) Date of Patent: Dec. 19, 2023

(54) REGULATION OF MIR-143 USING NUCLEIC ACID MOLECULES

(71) Applicant: CHILDREN'S HOSPITAL MEDICAL CENTER, Cincinnati, OH (US)

(72) Inventor: Dao Pan, Cincinnati, OH (US)

(73) Assignee: CHILDREN'S HOSPITAL MEDICAL CENTER, Cincinnati, OH (US)

(*) Notice: Subject to any disclaimer, the term of this patent is extended or adjusted under 35 U.S.C. 154(b) by 0 days.

(21) Appl. No.: 16/498,408

(22) PCT Filed: Mar. 29, 2018

(86) PCT No.: PCT/US2018/025002
§ 371 (c)(1),
(2) Date: Sep. 27, 2019

(87) PCT Pub. No.: WO2018/183594
PCT Pub. Date: Oct. 4, 2018

(65) Prior Publication Data
US 2020/0063132 A1  Feb. 27, 2020

Related U.S. Application Data

(60) Provisional application No. 62/478,109, filed on Mar. 29, 2017.

(51) Int. Cl.
*C12N 15/113*  (2010.01)
*A61P 35/00*  (2006.01)
*A61K 45/06*  (2006.01)

(52) U.S. Cl.
CPC ............ *C12N 15/113* (2013.01); *A61P 35/00* (2018.01); *A61K 45/06* (2013.01); *C12N 2310/13* (2013.01); *C12N 2310/141* (2013.01)

(58) Field of Classification Search
CPC .............. C12N 15/113; C12N 2310/13; C12N 2310/141
See application file for complete search history.

(56) References Cited

U.S. PATENT DOCUMENTS

| | | | | |
|---|---|---|---|---|
| 2010/0317713 | A1* | 12/2010 | Olson | A61K 45/06 435/325 |
| 2011/0190372 | A1* | 8/2011 | Tomic-Canic | A61P 17/02 514/44 A |
| 2012/0041048 | A1* | 2/2012 | Weinberg | A61P 35/04 514/44 A |
| 2014/0219974 | A1 | 8/2014 | Pan | |

FOREIGN PATENT DOCUMENTS

| | | | |
|---|---|---|---|
| WO | 2005/013901 A2 | 2/2005 | |
| WO | WO-2009142602 A1 * | 11/2009 | ............. C07K 14/34 |
| WO | 2010/129791 A1 | 11/2010 | |
| WO | 2011/084460 A1 | 7/2011 | |

OTHER PUBLICATIONS

Hollensen et al (RNA Biology 10:3, 406-414; Mar. 2013) (Year: 2013).*
Dimitrova et al (Cancer Discovery 6(2); 188-201, Feb. 2016) (Year: 2016).*
Hollensen et al (RNA Biology 10:3, 406-414, 2013 (Year: 2013).*
Hollensen et al (RNA Biology 10:3, 406-414, 2013, Supplemental Material (Year: 2013).*
Dong et al (bioRxiv 2020.01.30.927335) (Year: 2020).*
GenBank Accession NR_105060, *Homo sapiens* cardiac mesoderm enhancer-associated non-coding RNA (CARMN), transcript variant 2, long non-coding RNA (Year: 2020).*
Edbauer et al (Neuron 65, 373-384) (Year: 2010).*
Edbauer et al (Neuron 65, Supplemental Material, 15 pages) (Year: 2010).*
Gentner et al (Nature Methods 6(1):63-66, 2009) (Year: 2009).*
Gentner et al (Nature Methods 6(1): 5 pages of Supplementary Material, 2009) (Year: 2009).*
International Search Report from PCT/US2018/025002, dated Jul. 12, 2018, 5 pages.
Written Opinion from PCT/US2018/025002, dated Jul. 12, 2018, 5 pages.
Agarwal et al. (2015) "Predicting effective microRNA target sites in mammalian mRNAs" eLife, vol. 4, Article e05005 (38 pages).
Bagri et al. (2016) "Immunohistochemical analysis of mannose 6-phosphate/insulin-like growth factor 2 receptor in murine wild-type and mucopolysaccharidosis IIIB mutant central nervous system vasculature and implications for trans-blood brain barrier (BBB) transport" Molecular genetics and metabolism, vol. 117, No. 2, p. S24.

(Continued)

*Primary Examiner* — Richard A Schnizer
(74) *Attorney, Agent, or Firm* — ALGM LLP; Harry J. Guttman

(57) ABSTRACT

Some embodiments of the invention include a nucleic acid molecule comprising natural nucleotides, non-natural nucleotides, an LNA which comprises one or more RNA core molecules, or an RNA molecule which comprises more than one RNA core molecule. Some embodiments of the invention include a nucleic acid molecule comprising an RNA molecule which comprises more than one RNA core molecule. Other embodiments of the invention include a nucleic acid molecule comprising a DNA molecule encoding the RNA molecule (e.g., vector or viral vector). Other embodiments include compositions or pharmaceutical compositions that comprise the nucleic acid molecule. Some embodiments of the invention comprise reducing miR-143 in a cell. Other embodiments of the invention include methods to deliver a protein across the BBB. Other embodiments include methods for treating disease (e.g., LSD, neuronopathic disease, neurodegenerative disease, Hurler syndrome, or MPS I). Additional embodiments of the invention are also discussed herein.

19 Claims, 16 Drawing Sheets

Specification includes a Sequence Listing.

(56) References Cited

OTHER PUBLICATIONS

Bai et al. (2016) "Silencing microRNA-143 protects the integrity of the blood-brain barrier: implications for methamphetamine abuse" Scientific reports, vol. 6, Article 35642 (15 pages).

Banks et al. (2001) "Transport of human immunodeficiency virus type 1 pseudoviruses across the blood-brain barrier: role of envelope proteins and adsorptive endocytosis" Journal of Virology, vol. 75, No. 10, pp. 4681-4691.

Barbosa et al. (2003) "Improved and simple micro assay for sulfaled glycosaminoglycans quantification in biological extracts and its use in skin and muscle tissue studies" Glycobiology vol. 13, No. 9, pp. 647-653.

Begley et al. (2008) "Lysosomal storage diseases and the blood-brain barriel" Current pharmaceutical design, vol. 14, No. 16, pp. 1566-1580.

Betel et al. (2008) "The microRNA.org resource: targets and expression" Nucleic Acids Research, vol. 36(Database issue), pp. D149-D153.

Boustany (2013) "Lysosomal storage diseases—the horizon expands" Nature reviews. Neurology, vol. 9, No. 10, pp. 583-598.

Brooks et al. (2005) "Behavioural profiles of inbred mouse strains used as transgenic backgrounds. II: cognitive tests" Genes Brain Behav, vol. 4, No. 5, pp. 307-317.

Campos et al. (2012) "Mucopolysaccharidosis type I: current knowledge on its pathophysiological mechanisms" Metabolic brain disease, vol. 27, No. 2, pp. 121-129.

Chakraborty et al. (2017) "Therapeutic miRNA and siRNA: Moving from Bench to Clinic as Next Generation Medicine" Molecular therapy. Nucleic acids, vol. 8, pp. 132-143.

Cordes et al. (2009) "miR-145 and miR-143 regulate smooth muscle cell fate decisions" Nature, vol. 460, No. 7256, pp. 705-710.

Cressant et al. (2004) "Improved behavior and neuropathology in the mouse model of Sanfilippo type IIIB disease after adeno-associated virus-mediated gene transfer in the striatum" The Journal of neuroscience, vol. 24, No. 45, pp. 10229-10239.

Dahms et al. (1994) "The bovine mannose 6-phosphate/insulin-like growth factor II receptor. Localization of the insulin-like growth factor II binding site to domains 5-11" The Journal of biological chemistry, vol. 269, No. 5, pp. 3802-3809.

Dai et al. (2014) "Platelets are efficient and protective depots for storage, distribution, and delivery of lysosomal enzyme in mice with Hurler syndrome" Proc Natl Acad Sci U S A vol. 111, No. 7, pp. 2680-2685.

Ebert et al. (2007) "MicroRNA sponges: competitive inhibitors of small RNAs in mammalian cells" Nature methods, vol. 4, No. 9, pp. 721-726.

Ebert et al. (2010) "Emerging Roles for Natural MicroRNA Sponges" Current Biology, vol. 20, pp. R858-R861.

Ebert et al. (2010) "MicroRNA sponges: Progress and possibilities" RNA, vol. 16, pp. 2043-2050.

El-Amouri et al. (2014) "Normalization and improvement of CNS deficits in mice with hurler syndrome after long-term peripheral delivery of BBB-targeted iduronidase" Molecular Therapy: The Journal of the American Society of Gene Therapy, vol. 22, No. 12, pp. 2028-2037.

Elmen et al. (2008) "LNA-mediated microRNA silencing in non-human primates" Nature, vol. 452, pp. 896-900.

Enns et al. (2008) "Central nervous system therapy for lysosomal storage disorders" Neurosurgical focus, vol. 24, Nos. 3-4, Article E11 (12 pages).

Filiano et al. (2015) "Interactions of innate and adaptive immunity in brain development and function" Brain research, vol. 1617, pp. 18-27.

Friedman et al. (2015) "Blood-brain barrier in health and disease" Seminars in cell & developmental biology, vol. 38, p. 1.

Garmroudi et al. (1994) "Localization of the insulin-like growth factor II (IGF-II) binding/cross-linking site of the IGF-II/mannose 6-phosphate receptor to extracellular repeats 10-11" The Journal of biological chemistry, vol. 269, No. 43, pp. 26944-26952.

Gary-Bobo et al. (2007) "Mannose 6-phosphate receptor targeting and its applications in human Diseases" Curr Med Chem., vol. 14, No. 28, pp. 2945-2953.

Grubb et al., (2008) "Chemically modified beta-glucuronidase crosses blood-brain barrier and clears neuronal storage in murine mucopolysaccharidosis VII" PNAS, vol. 105, No. 7, pp. 2616-2621.

Guo et al. (2009) "Differential expression of microRNA species in human gastric cancer versus non-tumorous tissues" Journal of Gastroenterology and Hepatology, vol. 24, No. 4, pp. 652-657.

Ha et al. (2016) "Exosomes as therapeutic drug carriers and delivery vehicles across biological membranes: current perspectives and future challenges" Acta pharmaceutica Sinica. B, vol. 6, No. 4, pp. 287-296.

Haskell et al. (2002) "Retinoic acid signaling at sites of plasticity in the mature central nervous system" The Journal of comparative neurology, vol. 452, No. 3, pp. 228-241.

Hawkes et al. (2002) "Insulin-like growth factor-II/Mannose-6-phosphate receptor in the spinal cord and dorsal root ganglia of the adult rat" The European journal of neuroscience, vol. 15, No. 1, pp. 33-39.

Hawkes et al. (2003) "Insulin-like growth factor-II/mannose-6-phosphate receptor: widespread distribution in neurons of the central nervous system including those expressing cholinergic phenotype" The Journal of comparative neurology, vol. 458, No. 2, pp. 113-127.

Hawkes et al. (2004) "The insulin-like growth factor-II/mannose-6-phosphate receptor: structure, distribution and function in the central nervous system" Brain research reviews, vol. 44, Nos. 2-3, pp. 117-140.

Herculano-Houzel et al. (2005) "Isotropic fractionator: a simple, rapid method for the quantification of total cell and neuron numbers in the brain" The Journal of Neuroscience, vol. 25, No. 10, pp. 2518-2521.

Hille-Rehfeld (1995) "Mannose 6-phosphate receptors in sorting and transport of lysosomal enzymes" Biochimica et biophysica acta, vol. 1241, No. 2, pp. 177-194.

Janzen et al. (2017) "Cognitive and adaptive measurement endpoints for clinical trials in mucopolysaccharidoses types I, II, and III: A review of the literature" Molecular genetics and metabolism, vol. 121, No. 2, pp. 57-69.

Kasinski et al. (2011) "MicroRNAs en route to the clinic: progress in validating and targeting microRNAs for cancer therapy" Nature reviews Cancer, vol. 11, No. 12, pp. 849-864.

Klumperman et al. (1993) "Differences in the endosomal distributions of the two mannose 6-phosphate receptors" The Journal of cell biology, vol. 121, No. 5, pp. 997-1010.

Koeberl et al. (2012) "beta2 Agonists enhance the efficacy of simultaneous enzyme replacement therapy in murine Pompe disease" Molecular genetics and metabolism, vol. 105, No. 2, pp. 221-227.

Konishi et al. (2005) "Immunohistochemical distribution of cation-dependent mannose 6-phosphate receptors in the mouse central nervous system: comparison with that of cation-independent mannose 6-phophate receptors" Neuroscience letters, vol. 378, No. 1, pp. 7-12.

Körbelin et al. (2016) "A brain microvasculature endothelial cell-specific viral vector with the potential to treat neurovascular and neurological diseases" EMBO Molecular Medicine, vol. 8, No. 6, pp. 609-625.

Lidove et al. (2007) "Clinical results of enzyme replacement therapy in Fabry disease: a comprehensive review of literature" International journal of clinical practice, vol. 61, No. 2, pp. 293-302.

Lin et al. (2013) "Characterization of microRNA expression profiles and the discovery of novel microRNAs involved in cancer during human embryonic development" PloS One, vol. 8, No. 8, article e69230 (11 pages).

Lin et al. (2013) "Oligodendrocyte-specific activation of PERK signaling protects mice against experimental autoimmune encephalomyelitis" The Journal of Neuroscience, vol. 33, No. 14, pp. 5980-5991.

(56) References Cited

OTHER PUBLICATIONS

Liu et al. (2005) "Functional correction of CNS phenotypes in a lysosomal storage disease model using adeno-associated virus type 4 vectors" The Journal of neuroscience, vol. 25, No. 41, pp. 9321-9327.

Lopez-Ramirez et al. (2016) "Regulation of brain endothelial barrier function by microRNAs in health and neuroinflammation" FASEB journal, vol. 30, No. 8, pp. 2662-2672.

Morrione et al. (2013) "Dichotomy of decorin activity on the insulin-like growth factor-I system" FEBS J., vol. 280, No. 10, pp. 2138-2149.

Nixon (2013) "The role of autophagy in neurodegenerative disease" Nature medicine, vol. 19, No. 8, pp. 983-997.

Obermeier et al. (2013) "Development, maintenance and disruption of the blood-brain barrier" Nature medicine, vol. 19, No. 12, pp. 1584-1596.

Olson et al. (2004) "Structure of uPAR, plasminogen, and sugar-binding sites of the 300 kDa mannose 6-phosphate receptor" The EMBO journal, vol. 23, No. 10, pp. 2019-2028.

Pan (2011) "Cell- and gene-based therapeutic approaches for neurological deficits in mucopolysaccharidoses" Curr Pharm Biotechnol, vol. 12, No. 6, pp. 884-896.

Pan et al. (2002) "Biodistribution and toxicity studies of VSVG-pseudotyped lentiviral vector after intravenous administration in mice with the observation of in vivo transduction of bone marrow" Molecular therapy, vol. 6, No. 1, pp. 19-29.

Pan et al. (2008) "Progression of multiple behavioral deficits with various ages of onset in a murine model of Hurler syndrome" Brain research, vol. 1188, No. 241-253.

Pasquinelli (2012) "MicroRNAs and their targets: recognition, regulation and an emerging reciprocal relationship" Nature reviews. Genetics, vol. 13, No. 4, pp. 271-282.

Ponder et al. (2002) "Therapeutic neonatal hepatic gene therapy in mucopolysaccharidosis VII dogs" PNAS, vol. 99, No. 20, pp. 13102-13107.

Prada et al. (2013) "Neuronopathic lysosomal storage diseases: clinical and pathologic findings" Developmental disabilities research reviews, vol. 17, No. 3, pp. 226-246.

Sands et al. (2006) "Gene therapy for lysosomal storage diseases" Molecular therapy : the journal of the American Society of Gene Therapy, vol. 13, No. 5, pp. 839-849.

Scherr et al. (2007) "Lentivirus-mediated antagomir expression for specific inhibition of miRNA function" Nucleic acids research, vol. 35, No. 22, article e149 (9 pages).

Schultz et al. (2011) "Clarifying lysosomal storage diseases" Trends in neurosciences, vol. 34, No. 8, pp. 401-410.

Slaby et al. (2007) "Altered expression of miR-21, miR-31, miR-143 and miR-145 is related to clinicopathologic features of colorectal cancer" Oncology, vol. 72, Nos. 5-6, pp. 397-402.

Sly et al. (2013) "The final frontier—crossing the blood-brain barrier" EMBO molecular medicine 5(5):655-657.

Staba et al. (2004) Cord-blood transplants from unrelated donors in patients with Hurler's syndrome The New England journal of medicine, vol. 350, No. 19, pp. 1960-1969.

Stenvang et al. (2008) "The utility of LNA in microRNA-based cancer diagnostics and therapeutics" Seminars in Cancer Biology, vol. 18, pp. 89-102.

Tavazoie et al. (2008) "Endogenous human microRNAs that suppress breast cancer metastasis" Nature, vol. 451, No. 7175, pp. 147-152.

Urayama et al. (2004) "Developmentally regulated mannose 6-phosphate receptor-mediated transport of a lysosomal enzyme across the blood-brain barrier" PNAS, vol. 101, No. 34, pp. 12658-12663.

Urayama et al. (2007) "Epinephrine enhances lysosomal enzyme delivery across the blood-brain barrier by up-regulation of the mannose 6-phosphate receptor" PNAS, vol. 104, No. 31, pp. 12873-12878.

Urayama et al. (2008) "Mannose 6-phosphate receptor-mediated transport of sulfamidase across the blood-brain barrier in the newborn mouse" Molecular therapy : the journal of the American Society of Gene Therapy, vol. 16, No. 7, pp. 1261-1266.

Vogler et al. (1993) "Enzyme replacement with recombinant beta-glucuronidase in the newborn mucopolysaccharidosis type VII mouse" Pediatric research, vol. 34, No. 6, pp. 837-840.

Vogler et al. (1999) "Enzyme replacement in murine mucopolysaccharidosis type VII: neuronal and glial response to beta-glucuronidase requires early initiation of enzyme replacement therapy" Pediatric research, vol. 45, No. 6, pp. 838-844.

Wang et al. (2008) "Co-expression of MGMT(P140K) and alpha-L-iduronidase in primary hepatocytes from mucopolysaccharidosis type I mice enables efficient selection with metabolic correction" The Journal of Gene Medicine, vol. 10, No. 3, pp. 249-259.

Wang et al. (2009) "Reprogramming erythroid cells for lysosomal enzyme production leads to visceral and CNS cross-correction in mice with Hurler syndrome" Proc Natl Acad Sci USA, vol. 106, No. 47, pp. 19958-19963.

Wang et al. (2013) "Engineering a lysosomal enzyme with a derivative of receptor-binding domain of apoE enables delivery across the blood-brain barrier" Proceedings of the National Academy of Sciences of the United States of America, vol. 110, No. 8, pp. 2999-3004.

Wang et al. (2017) "Insulin-Like Growth Factor-II/Cation-Independent Mannose 6-Phosphate Receptor in Neurodegenerative Diseases" Molecular Neurobiology, vol. 54, No. 4, pp. 2636-2658.

Watson et al. (2006) "Intrathecal administration of AAV vectors for the treatment of lysosomal storage in the brains of MPS I mice" Gene Therapy, vol. 13, No. 11, pp. 917-925.

Worsham et al. (2006) "In vivo gene transfer into adult stem cells in unconditioned mice by in situ delivery of a lentiviral vector" Molecular Therapy, vol. 14, No. 4, pp. 514-524.

Wraith et al. (2004) "Enzyme replacement therapy for mucopolysaccharidosis I: a randomized, double-blinded, placebo-controlled, multinational study of recombinant human alpha-L-iduronidase (laronidase)" The Journal of Pediatrics, vol. 144, No. 5, pp. 581-588.

Xin et al. (2009) "MicroRNAs miR-143 and miR-145 modulate cytoskeletal dynamics and responsiveness of smooth muscle cells to injury" Genes & Development, vol. 23, No. 18, pp. 2166-2178.

Zheng et al. (2003) "Treatment of the mouse model of mucopolysaccharidosis I with retrovirally transduced bone marrow" Molecular Genetics and Metabolism, vol. 79, No. 4, pp. 233-244.

Zhu et al. (2009) "Glycoengineered Acid alpha-Glucosidase With Improved Efficacy at Correcting the Metabolic Aberrations and Motor Function Deficits in a Mouse Model of Pompe Disease" Molecular Therapy: The Journal of the American Society of Gene Therapy, vol. 17, No. 6, pp. 954-963.

\* cited by examiner

A

B

C

D

E

D

E

A

B

REGULATION OF MIR-143 USING NUCLEIC ACID MOLECULES

CROSS-REFERENCE TO RELATED APPLICATIONS

This application is a National Stage Entry of International Application No. PCT/US2018/025002 filed Mar. 29, 2018, entitled "NUCLEIC ACID MOLECULES AND THEIR METHODS OF USE" which is herein incorporated by reference in its entirety, and which claims the benefit of U.S. Provisional Application No. 62/478,109, filed Mar. 29, 2017, entitled "Manipulation of miR-143 regulates transfer of a lysosomal enzyme across the blood-brain barrier via Mannose 6-phosphate Receptor" which is herein incorporated by reference in its entirety.

REFERENCE TO A SEQUENCE LISTING

The instant application contains a Sequence Listing that has been submitted in ASCII format via EFS-Web and is hereby incorporated by reference in its entirety. (file name: 2020_11_seq_listing_36821_04040_ST25.txt, file creation date: Oct. 31, 2020, and file size: 31.5 KB)

BACKGROUND

Lysosomal storage disease (LSD) represents a category of inherited metabolic diseases triggered by the deficiency of lysosomal enzymes or components related to lysosomal functions. Some LSDs are caused by loss of or reduced lysosomal hydrolase activity, which can sometimes lead to accumulation of degradative intermediates and can result in multi-organ dysfunctions. Approximately two thirds of LSDs involve the central nervous system (CNS). The progressive CNS pathology can start at different ages and can cause neuronal dysfunctions and premature death if untreated, such as Pompe disease, Sandhoff's disease, mucopolysaccharidoses (MPS) type I, II and III. Hurler syndrome, a severe MPS I disease, is a neuronopathic LSDs that can be caused by the deficiency of α-L-iduronidase (IDUA) leading in some instances to accumulation of substrates (glycosaminoglycans (GAGs)) in multiple bodily tissues.

Prior treatments of enzyme replacement therapy (ERT) or hematopoietic stem-cell therapy (HSCT) are not fully successful and many challenges remain.

Certain embodiments of the invention address one or more of the deficiencies described above. For example, some embodiments of the invention include a nucleic acid molecule comprising natural nucleotides, non-natural nucleotides, an LNA which comprises one or more one RNA core molecules, or an RNA molecule which comprises more than one RNA core molecule. Some embodiments of the invention include a nucleic acid molecule comprising an RNA molecule which comprises more than one RNA core molecule. Still other embodiments of the invention include a nucleic acid molecule comprising a DNA molecule that encodes the RNA molecule (e.g., a vector or viral vector). Other embodiments of the invention include compositions or pharmaceutical compositions that comprise the nucleic acid molecule. Some embodiments of the invention comprise reducing miR-143 in a cell. Still other embodiments of the invention include methods to deliver a protein across the blood brain barrier (BBB). Yet other embodiments of the invention include methods for treating disease (e.g., lysosomal storage disease (LSD), a neuronopathic disease, a neurodegenerative disease, Hurler syndrome, or MPS I). Additional embodiments of the invention are also discussed herein.

SUMMARY

Some embodiments of the invention include a nucleic acid molecule comprising an RNA molecule where the RNA molecule comprises more than one RNA core molecule. In some instances, at least one of the more than one RNA core molecules is GAGCUACAGUGCUUCAUCUCA (SEQ ID NO:1) or SEQ ID NO:1 with one or more substitutions, one or more deletions, one or more insertions, or a combination thereof. In certain embodiments, the more than one RNA core molecules are linked together by one or more RNA core linkers which RNA core linkers each comprise one or more ribonucleotides. In other embodiments, at least one of the more than one RNA core molecules has a percent identity compared to SEQ ID NO:1, of at least about 33%, at least about 35%, at least about 38%, at least about 40%, at least about 42%, at least about 45%, at least about 47%, at least about 50%, at least about 52%, at least about 55%, at least about 57%, at least about 60%, at least about 61%, at least about 65%, at least about 66%, at least about 70%, at least about 71%, at least about 75%, at least about 76%, at least about 80%, at least about 81%, at least about 85%, at least about 90%, or at least about 95%. In yet other embodiments, all of the more than one RNA core molecules have a percent identity compared to SEQ ID NO:1, of at least about 33%, at least about 35%, at least about 38%, at least about 40%, at least about 42%, at least about 45%, at least about 47%, at least about 50%, at least about 52%, at least about 55%, at least about 57%, at least about 60%, at least about 61%, at least about 65%, at least about 66%, at least about 70%, at least about 71%, at least about 75%, at least about 76%, at least about 80%, at least about 81%, at least about 85%, at least about 90%, at least about 95%, or combinations thereof. In still other embodiments, the more than one RNA core molecules are selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:37, and SEQ ID NO:38. In some embodiments, at least one of the one or more RNA core linkers comprise 1, 2, 3, 4, 5, 6, 7, 8, 9, or 10 ribonucleotides. In other embodiments, all of the one or more RNA core linkers comprise 1, 2, 3, 4, 5, 6, 7, 8, 9, or 10 ribonucleotides. In some instances, at least one of the one or more RNA core linkers is selected from A, C, G, U, AA, CC, GG, UU, AC, AG, AU, CA, CG, CU, GA, GC, GU, UA, UC, UG, ACG, ACU, AGU, GCG, GCU, GGU, UCG, UCU, UGU, CGAU, CUAGA, or UCUAGA. In still other embodiments, the nucleic acid molecule comprises SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:39, or SEQ ID NO:40.

Some embodiments of the invention include a nucleic acid molecule comprising (a) a DNA molecule which encodes the RNA molecule of any of claims 1-8, (b) natural nucleotides and which binds to miR-143, (c) non-natural nucleotides and which binds to miR-143, (d) natural nucleotides and non-natural nucleotides and which binds to miR-143, or (e) an LNA which comprises one or more RNA core molecules. In other embodiments, the nucleic acid molecule is part of a vector, a viral vector, a retroviral vector, a lentiviral vector, an adenoviral vector, an adeno-associated viral vector, an AAV2, an scAAV, an AAV-Br1, a herpesviral vector, a chimeric viral vector, a plasmid, an expression vector, a conjugative vector, a nonconjugative vector, or a nanoparticle. In yet other embodiments, the nucleic acid molecule further comprises a promoter, a CMV promoter, a miniCMV promoter, an h1CMV promoter, an h2CMV promoter, an SV2 promoter, a U6 promoter, an H1 promoter, an SF promoter, an SFFV promoter, an EF promoter, an endothelial promoter, a Tie2 promoter, an RNA polymerase III promoter, a promotor for expression of shRNA, a promotor for expression of siRNA, or an RNA polymerase III promoter. In additional embodiments, the nucleic acid molecule further comprises a promoter and the promoter is directed to or specific to the brain, the liver, or the spleen. In certain embodiments, the nucleic acid molecule further comprises a promoter and the promoter is directed to or specific to a tissue, vascular endothelia, hepatocytes, smooth muscles, cardiomyocytes, hematopoietic stem/progenitors or their offspring, myeloid/erythroid progenitors or their offspring, an organ, brain, liver, kidney, spleen, heart, or lung. In some embodiments, the nucleic acid molecule further comprises DNA that encodes for a protein, a lysosomal protein, α-L-iduronidase (IDUA), iduronate-2-sulfatase, heparan N-sulfatase, N-acetyl-alpha-D-glucosaminidase, acid alpha-glucosidase, arylsulfatase A, or a protein that can be transported via M6PR.

Some embodiments of the invention include a composition comprising the nucleic acid molecule as disclosed herein (e.g., as disclosed above). In other embodiments, the amount of the nucleic acid molecule in the composition is from about 0.0001% (by weight total composition) to about 99%.

Some embodiments of the invention include a pharmaceutical composition comprising the nucleic acid molecule as disclosed herein (e.g., as disclosed above). In other embodiments, the amount of the nucleic acid molecule in the pharmaceutical composition is from about 0.0001% (by weight total composition) to about 50%.

Some embodiments of the invention include a method for reducing miR-143 (SEQ ID NO: 25) in a cell comprising administering the nucleic acid molecule as disclosed herein (e.g., as disclosed above), the composition as disclosed herein (e.g., as disclosed above), or the pharmaceutical composition as disclosed herein (e.g., as disclosed above).

Some embodiments of the invention include a method for delivering a protein across a blood brain barrier (BBB) in an animal comprising administering the nucleic acid molecule as disclosed herein (e.g., as disclosed above), the composition as disclosed herein (e.g., as disclosed above), or the pharmaceutical composition as disclosed herein (e.g., as disclosed above). In other embodiments of the method, the protein is endogenous, the protein is encoded in the nucleic acid molecule, the protein is encoded in a vector that is not part of the nucleic acid molecule, or a combination thereof. In yet other embodiments of the method, the protein is a lysosomal protein, α-L-iduronidase (IDUA), iduronate-2-sulfatase, heparan N-sulfatase, N-acetyl-alpha-D-glucosaminidase, acid alpha-glucosidase, arylsulfatase A, or a protein that can be transported via M6PR.

Some embodiments of the invention include a method for treating a disease in an animal comprising administering the nucleic acid molecule as disclosed herein (e.g., as disclosed above), the composition as disclosed herein (e.g., as disclosed above), or the pharmaceutical composition as disclosed herein (e.g., as disclosed above). In other embodiments, the disease can be a lysosomal storage disease (LSD), a neurological LSD, an inherited neurological LSD, Fabry Disease, Hurler syndrome (severe MPS I), Lysosomal Acid Lipase Deficiency, Mucopolysaccharidosis Type I (MPS I), Mucopolysaccharidosis Type II (MPS II), Mucopolysaccharidosis Type III (MPS III), MPS IIIA, MPS IIIB, Mucopolysaccharidosis Type IV (MPS IV), Mucopolysaccharidosis Type VI (MPS VI), Mucopolysaccharidosis Type VII (MPS VII), Neuronal Ceroid Lipofuscinosis, Pompe disease, Sandhoff's disease, metachromatic leukodystrophy, Thrombocytopenia, a neuronopathic disease, a neurodegenerative disease, Alzheimer's disease, Parkinson disease, or Huntington disease. In some embodiments, the disease can be a lysosomal storage diseases (LSD), neurological LSDs, inherited neurological LSDs, Fabry Disease, Gaucher Disease, Hurler syndrome (severe MPS I), Lysosomal Acid Lipase Deficiency, Mucopolysaccharidosis Type I (MPS I), Mucopolysaccharidosis Type II (MPS II), Mucopolysaccharidosis Type III (MPS III), MPS IIIA, MPS IIIB, MPS IIIC, MPS IIID, Mucopolysaccharidosis Type IV (MPS IV), Mucopolysaccharidosis Type VI (MPS VI), Mucopolysaccharidosis Type VII (MPS VII), Neuronal Ceroid Lipofuscinosis, Niemann-Pick disease, Pompe disease, Sandhoff's disease, Tay-Sachs, metachromatic leukodystrophy, Thrombocytopenia, neurodegenerative diseases, Alzheimer's disease, Parkinson disease, Huntington disease, cancers, tumors associated with cancers, acute myeloid leukemia (AML), HPV associated cancers, multiple myeloma, lymphoma, leukemia, bone marrow cancer, non-Hodgkin lymphoma, diffuse large B-cell lymphoma, glioblastoma multiforme, endometrial cancer, melanoma, prostate cancer, lung cancer, breast cancer, kidney cancer, chemotherapy resistant cancers, bladder cancer, urothelial cancer, renal cancer, basal cell carcinoma, thyroid cancer, squamous cell carcinoma, neuroblastoma, ovarian cancer, renal cell carcinoma, hepatocellular carcinoma, HPV associated cancers, colon cancer, pancreatic cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, cancer metastasis, or uterine cancer. In certain embodiments, the disease can be an LSD, a neurological LSD, a neuronopathic disease, a neurodegenerative disease, Hurler syndrome, cancer or MPS I. In some embodiments, the animal is a mammal, human, mouse, or rat. In other embodiments, the age of the animal is at least about two months, at least about three months, at least about four months, at least about one year, at least about two years, at least about three years, or at least about ten years. In yet other embodiments, the animal is a human and the age of the animal is at least about three years or at least about ten years. In still other embodiments, animal is a mouse or a rat and the age of the animal is at least about four months or at least about one year. In some embodiments, the administration comprises parenteral administration, a mucosal administration, intravenous administration, subcutaneous administration, topical administration, intradermal administration, oral administration, sublingual administration, intranasal administration, or intramuscular administration. In other embodiments, the nucleic acid molecule concentration is administered to the animal in a therapeutically effective amount or is administered to the animal in an amount of from about 0.01 mg of mg/kg animal body weight to about 15 mg of mg/kg animal body weight. In certain embodiments, the animal is in need of treatment. In yet other embodiments, the method further comprises administering a second vector that (a) does not comprise an inventive nucleic acid molecule as disclosed herein (e.g., as disclosed above) and (b) does encode a protein. In other embodiments, (1) the vector further comprises a promoter, (2) the protein is to be transported across the BBB after administration of the second vector, or (3) both. In certain embodiments, the protein is a lysosomal protein, α-L-iduronidase (IDUA), iduronate-2-sulfatase, heparan N-sulfatase, N-acetyl-alpha-D-glucosaminidase, acid alpha-glucosidase, arylsulfatase A, or a protein that can be transported via M6PR.

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
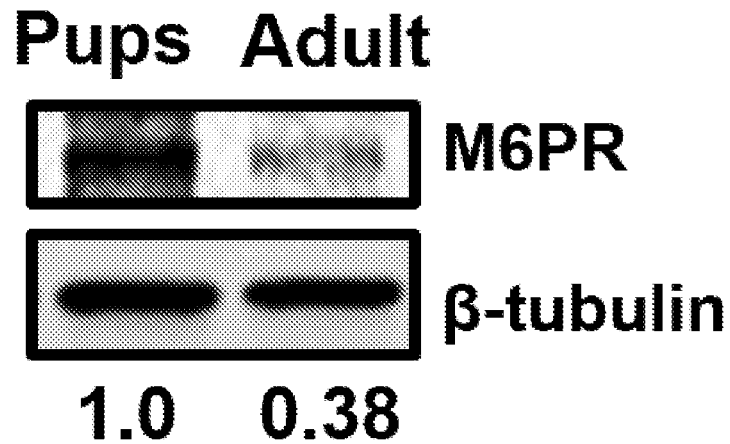
FIG. 1: Diminishing Mannose 6-Phosphate Receptor (M6PR, also known as IGF2R) protein expression in adult Brain MicroVasculature (BrMV) is associated with increase of miR143 compared to BrMV from pups. (A) Immunoblotting analysis of M6PR protein in BrMV from pups and adult mice. Numbers indicate relative M6PR levels (intensity of signals) with β-tubulin served as an internal loading control; n=12 for pups (8~10 days) and 11 for adult (~3 months) samples. (B) M6PR mRNA levels in BrMV isolated from pups and adult mice by TaqMan real time qPCR using β-actin as reference gene. Data are derived from 3-5 BrMV samples (each from n=10~15 mice), each with two RT reactions and quantified in triplicates. Results represent mean±SEM, *P<0.05. (C) Heat map representation of murine miRNA microarray showing miRNA clustering analysis of cerebral microvasculature in pups and adult mice. Data are derived from 2 pairs of BrMV samples (each from n=10~15 mice), and miRNA expression values >1,000 and p<0.05 are presented. (D) Venn diagram shows miR-143 as the only overlapped miRNA among two sets (using prediction algorithms TargetScan and miRanda) of predicted miRNAs targeting to 3'UTR of M6PR and upregulation miRNA candidate in microarray. (E) Relative expression of miR-143 and miR145a by real time qPCR analysis, validating the increasing abundance of miR-143/145a cluster in adult BrMV. The same sets of small RNA samples used in FIG. 1C were subjected to qPCR.
Figure 1:
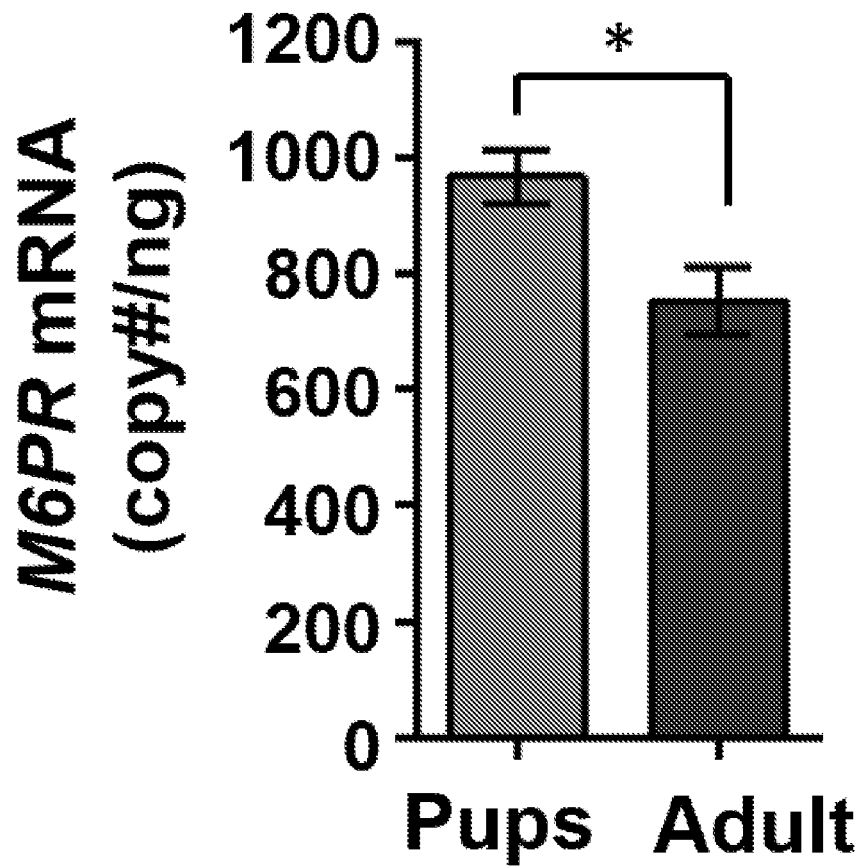
Figure 1:
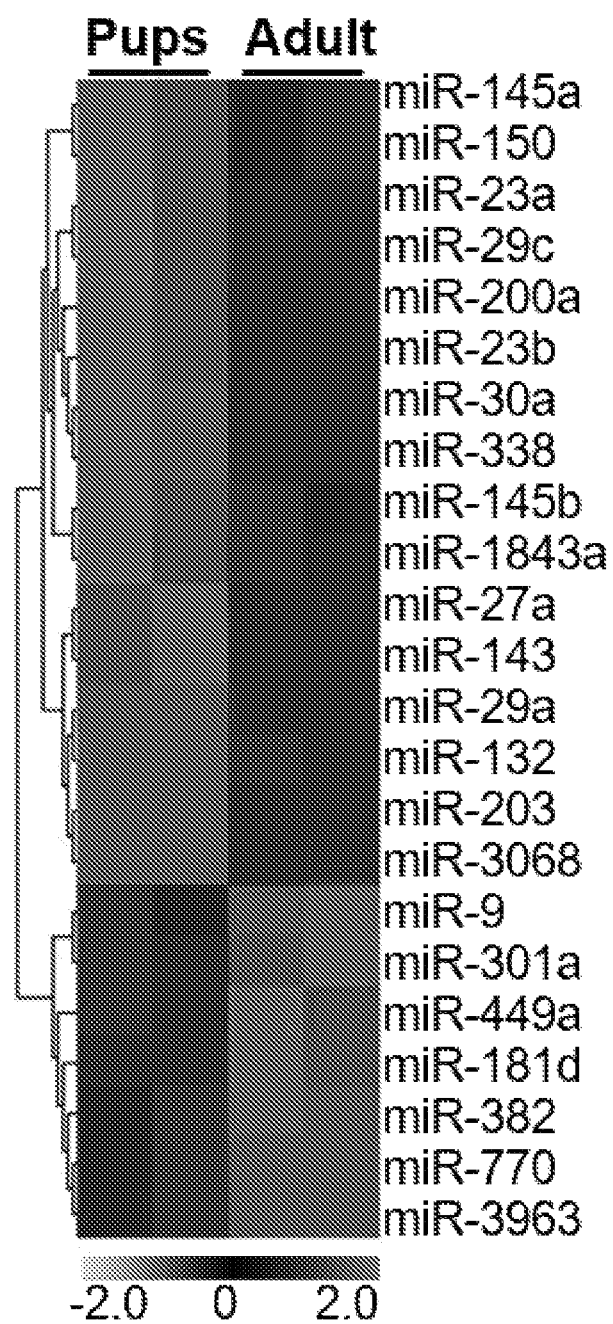
Figure 1:
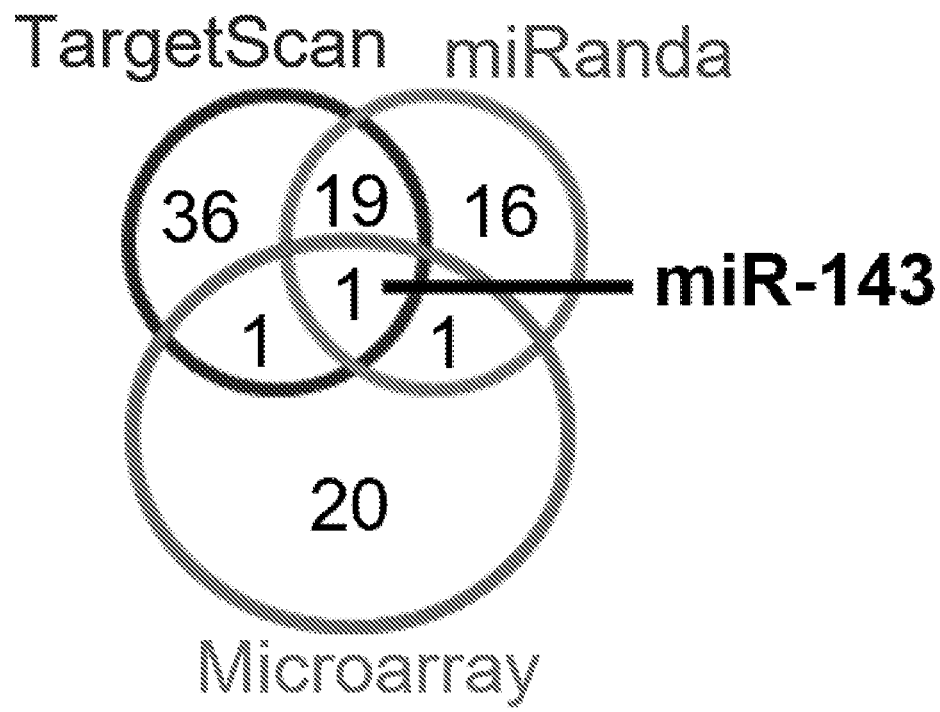
Figure 1:
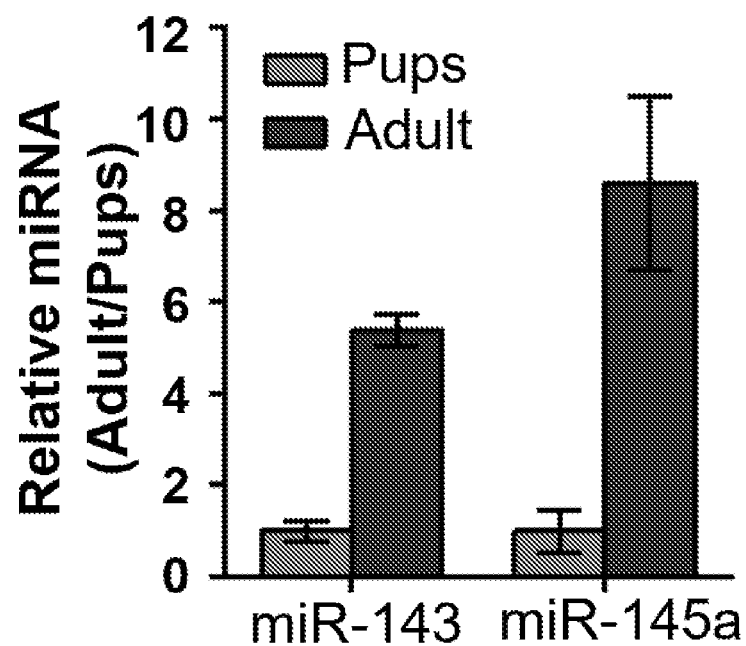

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include a nucleic acid molecule comprising natural nucleotides, non-natural nucleotides, an LNA which comprises one or more RNA core molecules, or an RNA molecule which comprises more than one RNA core molecule. Some embodiments of the invention include a nucleic acid molecule comprising an RNA molecule which comprises more than one RNA core molecule. Still other embodiments of the invention include a nucleic acid molecule comprising a DNA molecule that encodes the RNA molecule (e.g., a vector or viral vector). Other embodiments of the invention include compositions or pharmaceutical compositions that comprise the nucleic acid molecule. Some embodiments of the invention comprise reducing miR-143 in a cell. Still other embodiments of the invention include methods to deliver a protein across the blood brain barrier (BBB). Yet other embodiments of the invention include methods for treating disease (e.g., lysosomal storage disease (LSD), a neuronopathic disease, a neurodegenerative disease, Hurler syndrome, or MPS I). Additional embodiments of the invention are also discussed herein.

Nucleic Acid Molecules

Some embodiments of the invention include inventive nucleic acid molecules. In other embodiments, the inventive nucleic acid molecule comprises natural nucleotides (e.g., A, C, G, T, or U), non-natural nucleotides (e.g., those used in locked nucleic acids (LNA), or morpholinos, 2'-O-methyl, or 2'-O-methoxyethyl-modified nucleotides or oligonucleotides), or a combination thereof. In some embodiments, the inventive nucleic acid molecule comprises non-natural nucleotides (e.g., those used in locked nucleic acids, or morpholinos, 2'-O-methyl, or 2'-O-methoxyethyl-modified nucleotides or oligonucleotides) (see Stevang et al., "The utility of LNA in microRNA-based cancer diagnostics" Seminars in Cancer Biology (2008) Vol. 18, pp. 89-102 (which is herein incorporate by reference in its entirety); Elmen et al., "LNA-mediated microRNA silencing in non-human primates" Nature (2008) Vol. 452, pp. 896-900 (which is herein incorporate by reference in its entirety)). In other embodiments, the inventive nucleic acid molecule can be designed to bind to (e.g., does bind to) one or more miR-143 (SEQ ID NO:25). In some embodiments, the inventive nucleic acid molecule comprises non-natural nucleotides (e.g., those used in locked nucleic acids, or morpholinos, 2'-O-methyl, or 2'-O-methoxyethyl-modified nucleotides or oligonucleotides) and the inventive nucleic acid molecule can be designed to bind to (e.g., does bind to) one or more miR-143 (SEQ ID NO:25). In some embodiments, the inventive nucleic acid molecule comprises natural nucleotides and the inventive nucleic acid molecule can be designed to bind to (e.g., does bind to) one or more miR-143 (SEQ ID NO:25). In some embodiments, the inventive nucleic acid molecule comprises natural nucleotides and non-natural nucleotides, and the inventive nucleic acid molecule can be designed to bind to (e.g., does bind to) one or more miR-143 (SEQ ID NO:25). In some embodiments, the inventive nucleic acid molecule comprises a locked nucleic acid (LNA) and the inventive nucleic acid molecule is designed to bind to (e.g., does bind to) one or more miR-143.

In other embodiments, the inventive nucleic acid molecule comprises an inventive RNA molecule. In other embodiments, the inventive RNA molecule comprises natural nucleotides (e.g., A, C, G, or U), non-natural nucleotides (e.g., those used in locked nucleic acids (LNA), or morpholinos, 2'-O-methyl, or 2'-O-methoxyethyl-modified nucleotides or oligonucleotides), or a combination thereof. In other embodiments, the inventive RNA molecule can be designed to bind to (e.g., does bind to) one or more miR-143 (SEQ ID NO:25). In some embodiments, the inventive RNA molecule comprises non-natural nucleotides and the inventive RNA molecule can be designed to bind to (e.g., does bind to) one or more miR-143. In some embodiments, the inventive RNA molecule comprises natural nucleotides and the inventive RNA molecule can be designed to bind to (e.g., does bind to) one or more miR-143. In some embodiments, the inventive RNA molecule comprises non-natural nucleotides and natural nucleotides, and the inventive RNA molecule can be designed to bind to (e.g., does bind to) one or more miR-143. In some embodiments, the inventive RNA molecule comprises a locked nucleic acid (LNA) and the inventive nucleic acid molecule is designed to bind to (e.g., does bind to) one or more miR-143. In some embodiments, the inventive RNA molecule comprises an shRNA (short hairpin RNA). In some embodiments, the inventive RNA molecule comprises an shRNA (short hairpin RNA) and the inventive RNA molecule is designed to bind to (e.g., does bind to) one or more miR-143. In certain embodiments, the inventive RNA molecule (e.g., comprising natural nucleotides, non-natural nucleotides, or a combination thereof, or an LNA) comprises one or more (e.g., more than one) RNA core molecules. In certain embodiments, the inventive RNA molecule (e.g., comprising natural nucleotides, non-natural nucleotides, or a combination thereof, or an LNA) comprises one or more (e.g., more than one) RNA core molecules and the inventive RNA molecule is designed to bind to (e.g., does bind to) one or more miR-143 (SEQ ID NO:25). In some embodiments, the RNA core molecule can be GAGCUACAGUGCUUCAUCUCA (SEQ ID NO:1), or can be SEQ ID NO:1 with one or more substitutions (e.g., one or more substitutions of 1, 2, 3, 4, 5, 6, 7, 8, 9, or 10 nucleotides each), SEQ ID NO:1 with one or more deletions (e.g., one or more deletions of 1, 2, 3, 4, 5, 6, 7, 8, 9, 10, 11, 12, 13, 14, 15, 16, 17, 18, 19, 20, or 21 nucleotides each), or SEQ ID NO:1 with one or more insertions (e.g., one or more insertions of 1, 2, 3, 4, 5, 6, 7, 8, 9, or 10 nucleotides each, which can be added on the terminal nucleotide of the sequence (e.g., 5' or 3' end) or between two nucleotides of the sequence), or a combination thereof. In other embodiments, the percent identity (i.e., compared to GAGCUACAGUGCUUCAUCUCA (SEQ ID NO:1)) of at least one of the RNA core molecules (e.g., 1, 2, 3, 4, 5, 6, 7, 8, 9, 10, 12, 13, 14, 15, or 16 RNA core molecules, or all RNA core molecules) is about 33%, about 35%, about 38%, about 40%, about 42%, about 45%, about 47%, about 50%, about 52%, about 55%, about 57%, about 60%, about 61%, about 65%, about 66%, about 70%, about 71%, about 75%, about 76%, about 80%, about 81%, about 85%, about 90%, about 95%, about 100%, of at least about 33%, at least about 35%, at least about 38%, at least about 40%, at least about 42%, at least about 45%, at least about 47%, at least about 50%, at least about 52%, at least about 55%, at least about 57%, at least about 60%, at least about 61%, at least about 65%, at least about 66%, at least about 70%, at least about 71%, at least about 75%, at least about 76%, at least about 80%, at least about 81%, at least about 85%, at least about 90%, at least about 95%, or combinations thereof. In certain embodiments, one or more RNA core molecules bind to miR-143 (e.g., with a predicted ΔG (e.g., using RNAhybrid software (<<bibiserv2.cebitec.uni-bielefeld.de/rnahybrid>>) of about −5, about −10, about −20, about −30, about −40, about −50, or about −60 kcal/mol, or combinations thereof). In certain embodiments, the number of RNA core molecules in the inventive RNA molecule with different sequences is 1, 2, 3, 4, 5, 6, 7, 8, 9, 10, 11, 12, 13, 14, 15, or 16. In some embodiments, the RNA molecules comprises more than one copy of one or more RNA core molecule (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30). In certain embodiments, the RNA core molecules can be linked together by one or more RNA core linkers (e.g., 1, 2, 3, 4, 5, 6, 7, 8, 9, 10, 11, or 12 RNA core linkers which each may have different sequences) comprising one or more ribonucleotides (e.g., 1, 2, 3, 4, 5, 6, 7, 8, 9, 10, 11, or 12 ribonucleotides). In some instances, there is one RNA core linker between each RNA core molecule and each RNA core linker can be the same or different (e.g., each RNA core linker can have the same sequence or different sequence and/or can have the same or different number of nucleotides). Nonlimiting examples of RNA core linkers include A, C, G, U, AA, CC, GG, UU, AC, AG, AU, CA, CG, CU, GA, GC, GU, UA, UC, UG, ACG, ACU, AGU, CGA, GCG, GCU, GGU, UCG, UCU, UGU, CGAU, CUUC, CAAU, CUCA, UCCA, CUAGA, or UCUAGA. Some nonlimiting embodiments of RNA core molecules can comprise:

(SEQ ID NO: 1)
GAGCUACAGUGCUUCAUCUCA, (SEQ ID NO: 2)
GAGCUACAGACGUCAUCUCA, (SEQ ID NO: 3)
GAGCUACAGUGGAUCCUUCAUCUCA, (SEQ ID NO: 4)
GAGCUACAGUGCUUCAUCGAUCUCA, (SEQ ID NO: 5)
GGAUCAGCUACAGUGCUUCAUCUCA (SEQ ID NO: 6)
GAUCGAGCUACAGUGCUUCAUCUCA (SEQ ID NO: 7)
GAGCUACAGACGUCAUCGAUCUCA, (SEQ ID NO: 8)
GGAUCAGCUACAGACGUCAUCGAUCUCA, (SEQ ID NO: 9)
AAGCCACAUGCAUCUCAC, (SEQ ID NO: 10)
GCUCCGUGCCCUACCUCAUCUCU, (SEQ ID NO: 11)
UGAGCUGUAGGUCUCAUCUCU, (SEQ ID NO: 37)
UUUGGGUAUAGGUCUCAUCUCU,
or (SEQ ID NO: 38)
GCAUAAGGCCGGACGCAUCUCAA.

Nonlimiting examples of inventive RNA molecules can comprise one or more of the following sequences:

(SEQ ID NO: 12)
(CUAGAGAGCUACAGACGUCAUCUCACGAUGAGCUACAGUGGAUCCUUCAU CUCAU)$_4$ (see FIG. 3C), (SEQ ID NO: 13)
(CUAGAGAGCUACAGACGUCAUCUCACGAUGAGCUACAGUGGAUCCUUCAU CUCAU)$_3$, (SEQ ID NO: 14)
(AGUGAGCUACAGUGCUUCAUCUCAUGGAGCUACAGUGGAUCCUUCAUCUC A)$_5$, (SEQ ID NO: 15)
(AGUGAGCUACAGUGCUUCAUCUCAUGGAGCUACAGUGGAUCCUUCAUCUC A)$_2$, (SEQ ID NO: 16)
UGGAGCUACAGUGGAUCCUUCAUCUCA(AGUGAGCUACAGUGCUUCAUCUC AUGGAGCUACAGUGGAUCCUUCAUCUCA)$_2$, (SEQ ID NO: 17)
(CAUGAGCUACAGUGGAUCCUUCAUCUCACGAUGAGCUACAGUGGAUCCUU CAUCUCA)$_4$, (SEQ ID NO: 18)
(CAUGAGCUACAGUGGAUCCUUCAUCUCACAUGAGCUACAGUGGAUCCUUC AUCUCA)$_4$, (SEQ ID NO: 19)
(UCCAUGAGCUACAGUGGAUCCUUCAUCUCAAGAGCUACAGUGCUUCAUCU CA)$_3$, (SEQ ID NO: 20)
(CAUAAGCCACAUGCAUCUCACUGCUCCGUGCCCUACCUCAUCUCU)$_4$ (SEQ ID NO: 21)
(CUGCUCCGUGCCCUACCUCAUCUCUUAUGAGCUGUAGGUCUCAUCUCU)$_4$ (SEQ ID NO: 22)
(CUGCUCCGUGCCCUACCUCAUCUCUUCCAUGAGCUGUAGGUCUCAUCUC U)$_3$ (SEQ ID NO: 23)
(CUUCUGAGCUGUAGGUCUCAUCUCUCAGCUCCGUGCCCUACCUCAUCUC U)$_4$, (SEQ ID NO: 24)
(CUCAUGAGCUGUAGGUCUCAUCUCUCGAGCUCCGUGCCCUACCUCAUCUC U)$_5$, (SEQ ID NO: 39)
(CUAGAGAGCUACAGACGUCAUCUCACGAUGAGCUACAGUGGAUCCUUCAU CUCAU)$_2$,
or (SEQ ID NO: 40)
(CUAGAGAGCUACAGACGUCAUCUCACGAUGAGCUACAGUGGAUCCUUCAU CUCAU)$_1$.

In some embodiments, the inventive nucleic acid molecule comprises an inventive DNA molecule that encodes an inventive RNA molecule as disclosed herein. In certain embodiments, the inventive RNA molecule comprises natural nucleotides (e.g., A, C, G, or U), non-natural nucleotides (e.g., those used in locked nucleic acids (LNA), or morpholinos, 2'-O-methyl, or 2'-O-methoxyethyl-modified nucleotides or oligonucleotides), or a combination thereof. In other embodiments, the inventive RNA molecule can be designed to bind to (e.g., does bind to) one or more miR-143 (SEQ ID NO:25). In some embodiments, the inventive RNA molecule comprises non-natural nucleotides (e.g., those used in locked nucleic acids, or morpholinos, 2'-O-methyl, or 2'-O-methoxyethyl-modified nucleotides or oligonucleotides) (see Stevang et al., "The utility of LNA in microRNA-based cancer diagnostics" Seminars in Cancer Biology (2008) Vol. 18, pp. 89-102 (which is herein incorporate by reference in its entirety); Elmen et al., "LNA-mediated microRNA silencing in non-human primates" Nature (2008) Vol. 452, pp. 896-900 (which is herein incorporate by reference in its entirety)). In some embodiments, the inventive RNA molecule comprises non-natural nucleotides and the inventive RNA molecule can be designed to bind to (e.g., does bind to) one or more miR-143. In some embodiments, the inventive RNA molecule comprises natural nucleotides and the inventive RNA molecule can be designed to bind to (e.g., does bind to) one or more miR-143. In some embodiments, the inventive RNA molecule comprises non-natural nucleotides and natural nucleotides, and the inventive RNA molecule can be designed to bind to (e.g., does bind to) one or more miR-143. In some embodiments, the inventive RNA molecule comprises a locked nucleic acid (LNA) and the inventive nucleic acid molecule is designed to bind to (e.g., does bind to) one or more miR-143. In some embodiments, the inventive RNA molecule comprises an shRNA (short hairpin RNA). In some embodiments, the inventive RNA molecule comprises an shRNA (short hairpin RNA) and the inventive RNA molecule is designed to bind to (e.g., does bind to) one or more miR-143. In other embodiments, the inventive DNA molecule encodes an RNA molecule that comprises one or more RNA core molecules. In still other embodiments, the inventive DNA molecule encodes an RNA molecule that comprises more than one RNA core molecule and RNA core linkers. In other embodiments, the inventive DNA molecule encodes an RNA molecule that comprises more than one RNA core molecule and RNA core linkers, and the encoded RNA molecule is designed to bind to (e.g., does bind to) one or more miR-143 (SEQ ID NO:25). In some embodiments, the inventive DNA molecule comprises an artificial 3'UTR.

In certain embodiments, the inventive nucleic acid molecule is included in a vector (e.g., a viral vector, a retroviral vector, a lentiviral vector, an adenoviral vector, an adeno-associated viral vector, an AAV2, an scAAV, an AAV-Br1 (e.g., see KORBELIN et al., "A brain microvasculature endothelial cell-specific viral vector with the potential to treat neurovascular and neurological diseases" EMBO Mol. Med. (2016) Vol. 8, pp., 609-625), a herpes viral vector, a chimeric viral vector, a plasmid, an expression vector, a conjugative vector, a nonconjugative vector, or a nanoparticle (e.g., metal, gold, liposome, calcium phosphate with liposome, PEGylated metal such as gold, cationic, or nanoparticles made from or comprising the inventive DNA)). In some embodiments, the nucleic acid molecule, as disclosed herein, is operatively linked to a promoter operable under conditions whereby the encoded RNA is made. Any suitable promoter can be used, including but not limited to a CMV promoter, a miniCMV promoter, an h1CMV promoter, an h2CMV promoter, an SV2 promoter, a U6 promoter, an SF promoter, an SFFV promoter, an EF promoter, an endothelial promoter (e.g., Tie2 promoter), an RNA polymerase III promoter (e.g., U6 promoter or H1 promoter), or a promotor for expression of shRNA or siRNA (e.g., an RNA polymerase III promoter, such as U6 promoter or H1 promoter). In some embodiments, the promotor can be directed to or specific to a tissue (e.g., vascular endothelia, hepatocytes, smooth muscles, cardiomyocytes, hematopoietic stem/progenitors, myeloid/erythroid progenitors, or their offspring) or an organ (e.g., brain, liver, kidney, spleen, heart, or lung). In other embodiments, the vector further comprises DNA that encodes for a protein (e.g., to be delivered across the BBB), such as but not limited to IDUA, IDUAmyc, iduronate-2-sulfatase, heparan N-sulfatase, N-acetyl-alpha-D-glucosaminidase, acid alpha-glucosidase, arylsulfatase A, or a protein that can be transported via M6PR (e.g., a protein that has been modified with M6PR residues to use a transport pathway via M6PR). In certain embodiments, the DNA that encodes the protein may be under the control of the same or different promotor (e.g., those described herein) as the promotor linked to the DNA encoding the RNA molecule.

In some embodiments, the inventive nucleic acid molecule is in a cell, which in some instances the cell can be administered as part of a treatment (e.g., as disclosed herein).

Compositions and Pharmaceutical Compositions

In certain embodiments, one or more inventive nucleic acid molecules (e.g., a DNA molecule that encodes an RNA molecule that comprises one or more RNA core molecules, such as a vector, or an LNA which comprises one or more RNA core molecules) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%. In certain embodiments, a vector that does not comprise the inventive nucleic acid molecule but which does comprise DNA encoding a protein (e.g., to be delivered across the BBB) can be in the same composition as the inventive nucleic acid molecules as described herein (e.g., with the amounts as described herein) or can be in a separate composition with the amounts as described herein.

In some embodiments, one or more inventive nucleic acid molecules (e.g., a DNA molecule that encodes an RNA molecule that comprises one or more RNA core molecules or an LNA which comprises one or more RNA core molecules) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more one or more inventive nucleic acid molecules (e.g., a DNA molecule that encodes an RNA molecule that comprises one or more RNA core molecules or an LNA which comprises one or more RNA core molecules). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as but not limited to measurement of the amount of miR-143 in the cell, the miR-143 activity in the cell, the M6RP (also known as IGF2R) concentration in a cell, the M6RP expression in a cell, the BBB permeability of one or more proteins, the BBB permeability of one or more lysosomal proteins (e.g., IDUA), the IDUA concentration or activity in the CNS, the extent of one or more CNS abnormalities caused by an LSD, the accumulation of substrates (e.g., glycosaminoglycans (GAGs)) in one or more bodily tissues, or the reduction of cancer growth or delay/prevention of metastasis. The blood brain barrier (BBB) comprises a network of cerebral blood vessels formed by continuous layer of endothelial cells and supporting cells that regulate the passage of solutes between circulation and brain.

In some embodiments, one or more one or more inventive nucleic acid molecules (e.g., a DNA molecule that encodes an RNA molecule that comprises one or more RNA core molecules or an LNA which comprises one or more RNA core molecules) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In certain embodiments, a vector that does not comprise the inventive nucleic acid molecule but which does comprise DNA encoding a protein (e.g., to be delivered across the BBB) can be in the same pharmaceutical composition as the inventive nucleic acid molecules as described herein (e.g., with the amounts as described herein) or can be in a separate composition (e.g., pharmaceutical composition) with the amounts as described herein. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, a mucosal administration, intravenous administration, depot injection (e.g., solid or oil based), subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or arachis oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the one or more inventive nucleic acid molecules (e.g., a DNA molecule that encodes an RNA molecule that comprises one or more RNA core molecules or an LNA which comprises one or more RNA core molecules) substantially immediately upon the administration or any substantially predetermined time or time after administration. Such formulations can include, for example, controlled release formulations such as various controlled release compositions and coatings. For example, an injection could be used for a controlled release (e.g., of a DNA molecule that encodes an RNA molecule that comprises one or more RNA core molecules), and in some instances, could be injected once per month (or once per day, once per week, once per three months, once per six months, or once per year).

Other formulations (e.g., formulations of a pharmaceutical composition) can, in certain embodiments, include those incorporating the one or more inventive nucleic acid molecules (e.g., a DNA molecule that encodes an RNA molecule that comprises one or more RNA core molecules or an LNA which comprises one or more RNA core molecules) (or control release formulation) into food, food stuffs, feed, or drink. For example, a DNA molecule that encodes an RNA molecule that comprises one or more RNA core molecules could be administered orally once per day, twice per day, three times per day, once per two days, or once per week.

Some embodiments of the invention can include methods of treating an organism for a disease (e.g., lysosomal storage disease, a neuronopathic disease, a neurodegenerative disease, or both). In certain embodiments, treating comprises administering at least one of the one or more inventive nucleic acid molecules (e.g., a DNA molecule that encodes an RNA molecule that comprises one or more RNA core molecules or an LNA which comprises one or more RNA core molecules). In other embodiments, treating comprises administering at least one of the one or more inventive nucleic acid molecules (e.g., a DNA molecule that encodes an RNA molecule that comprises one or more RNA core molecules or an LNA which comprises one or more RNA core molecules) to an animal that is effective to treat disease (e.g., LSDs, neurological LSDs, neurodegenerative diseases, Hurler syndrome, or MPS I). In some embodiments, a composition or pharmaceutical composition comprises at least one of the one or more inventive nucleic acid molecules (e.g., a DNA molecule that encodes an RNA molecule that comprises one or more RNA core molecules or an LNA which comprises one or more RNA core molecules) which can be administered to an animal (e.g., mammals, primates, monkeys, or humans) in an amount of about 0.005 to about 100 mg/kg body weight, about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some conditions, the dosage can be about 0.5 mg/kg human body weight, about 5 mg/kg human body weight, about 6.5 mg/kg human body weight, about 10 mg/kg human body weight, about 50 mg/kg human body weight, about 80 mg/kg human body weight, or about 100 mg/kg human body weight. In some instances, some animals (e.g., mammals, mice, rabbits, feline, porcine, or canine) can be administered a dosage of about 0.005 to about 100 mg/kg body weight, about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, one or more inventive nucleic acid molecules (e.g., a DNA molecule that encodes an RNA molecule that comprises one or more RNA core molecules or an LNA which comprises one or more RNA core molecules) can be administered in combination with one or more other therapeutic agents (e.g., a vector that does not comprise the inventive nucleic acid molecule but which does comprise DNA encoding a protein (e.g., to be delivered across the BBB) with the amounts as described herein) or can be in a separate composition (e.g., a pharmaceutical composition) (e.g., with the amounts as described herein) to treat a given disease (e.g., lysosomal storage disease, a neuronopathic disease, a neurodegenerative disease, neurological disease, or cancer).

In some embodiments, the compositions can include a unit dose of one or more of the one or more inventive nucleic acid molecules (e.g., a DNA molecule that encodes an RNA molecule that comprises one or more RNA core molecules or an LNA which comprises one or more RNA core molecules) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Methods to Reduce microRNA in a Cell

Some embodiments of the invention include methods to reduce miR-143 (UGAGAUGAAGCACUGUAGCUC (SEQ ID NO: 25)) in a cell. In some embodiments, the method to reduce miR-143 comprises administering an inventive nucleic acid molecule (e.g., as disclosed herein), such as an inventive DNA molecule (e.g., a vector) as disclosed herein, administering a composition as disclosed herein, or administering a pharmaceutical composition, as disclosed herein.

Methods to Deliver a Protein Across the Blood-Brain Barrier (BBB)

Some embodiments of the invention include methods to deliver a protein across the BBB. In certain embodiments, the delivery of the protein across the BBB is via M6PR (e.g., via an M6PR-transcytosis pathway). In other embodiments, the protein to be delivered is endogenous. In some embodiments, the protein to be delivered is not endogenous. In certain embodiments, the method to deliver a protein across the BBB comprises administering an inventive nucleic acid molecule (e.g., as disclosed herein) to an animal (e.g., a mammal, human, mouse, or rat). In other embodiments, the protein is encoded in the vector comprising the inventive nucleic acid molecule. In still other embodiments, the protein is encoded in a vector that does not comprise an inventive nucleic acid molecule, and the vector encoding the protein can be administered together with (e.g., simultaneously or in the same solution) or separately from (e.g., in separate solutions at different times) from the administration of the vector comprising the inventive nucleic acid molecule.

In some embodiments, the protein to be delivered is a recombinant protein. In other embodiments, the protein to be delivered is a protein (e.g., a recombinant protein) that has been modified with one or more M6PR residues (e.g., via additions or substitutions of amino acids in the original protein) so that it can be transported via a CI-M6PR/IGF2R pathway (e.g., via M6PR). In other embodiments, the protein to be delivered is a protein (e.g., a recombinant protein) that has been tagged with IGF2 (e.g., at the N-terminal, C-terminal, or in between) so that it can be transported via a CI-M6PR/IGF2R pathway (e.g., via M6PR).

In some embodiments, the protein to be delivered is endogenous, is not encoded in the vector comprising the inventive nucleic acid molecule, and is not administered in a separate vector. In certain embodiments, the endogenous protein (i.e., no protein is added via a vector) is transported across the BBB.

In yet other embodiments, more than one protein can be delivered across the BBB. In some embodiments, at least one of the more than one protein is endogenous. In some embodiments, at least one of the more than one protein is added by a vector (e.g., a vector also comprising the inventive nucleic acid, a vector not comprising the inventive nucleic acid, or a combination thereof). In other embodiments, at least one of the more than one protein is endogenous and at least one of the more than one protein is added by a vector (e.g., a vector also comprising the inventive nucleic acid, a vector not comprising the inventive nucleic acid, or a combination thereof).

In some embodiments, the protein to be delivered across the BBB can be a lysosomal protein (e.g., a lysosomal enzyme or a lysosomal hydrolase), α-L-iduronidase (IDUA), iduronate-2-sulfatase, heparan N-sulfatase, N-acetyl-alpha-D-glucosaminidase, acid alpha-glucosidase, arylsulfatase A, or a protein that can be transported via M6PR (e.g., a protein that has been modified with mannose-6-phosphate receptor residues to use a transport pathway via M6PR). In some embodiments, the protein is a fusion protein.

Methods to Treat Disease

Some embodiments of the invention include treatment of disease (e.g., LSDs, neurological LSDs, neurodegenerative diseases, Hurler syndrome, or MPS I) by administering one or more inventive nucleic acid molecules (e.g., a DNA molecule that encodes an RNA molecule that comprises one or more RNA core molecules or an LNA which comprises one or more RNA core molecules), as disclosed herein, administering a composition as disclosed herein, or administering a pharmaceutical composition, as disclosed herein. One or more inventive nucleic acid molecules (e.g., a DNA molecule that encodes an RNA molecule that comprises one or more RNA core molecules or an LNA which comprises one or more RNA core molecules) can be administered to animals by any number of suitable administration routes or formulations. One or more inventive nucleic acid molecules (e.g., a DNA molecule that encodes an RNA molecule that comprises one or more RNA core molecules or an LNA which comprises one or more RNA core molecules) can also be used to treat animals for a variety of diseases. Animals include but are not limited to mammals, primates, rodents, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of one or more inventive nucleic acid molecules (e.g., a DNA molecule that encodes an RNA molecule that comprises one or more RNA core molecules or an LNA which comprises one or more RNA core molecules) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, a mucosal administration, intravenous administration, depot injection, subcutaneous administration, topical administration, intradermal administration, oral administration, sublingual administration, intranasal administration, or intramuscular administration. The choice of administration route can depend on the inventive nucleic acid molecule identity (e.g., the physical and chemical properties of the inventive nucleic acid molecules) as well as the age and weight of the animal, the particular disease (e.g., LSDs, neurological LSDs, neurodegenerative diseases, Hurler syndrome, or MPS I), and the severity of the disease (e.g., stage or severity of disease). Of course, combinations of administration routes can be administered, as desired.

Some embodiments of the invention include a method for providing a subject with a composition comprising one or more inventive nucleic acid molecules (e.g., a DNA molecule that encodes an RNA molecule that comprises one or more RNA core molecules or an LNA which comprises one or more RNA core molecules) described herein (e.g., a pharmaceutical composition) which comprises one or more administrations of one or more such compositions; the compositions may be the same or different if there is more than one administration.

Diseases that can be treated in an animal (e.g., mammals, porcine, canine, avian (e.g., chicken), bovine, feline, primates, rodents, monkeys, rabbits, mice, rats, and humans) using one or more inventive nucleic acid molecules (e.g., a DNA molecule that encodes an RNA molecule that comprises one or more RNA core molecules or an LNA which comprises one or more RNA core molecules) include, but are not limited to lysosomal storage disease, a neuronopathic disease, a neurodegenerative disease, or cancer.

In some embodiments, diseases that can be treated in an animal (e.g., mammals, porcine, canine, avian (e.g., chicken), bovine, feline, primates, rodents, monkeys, rabbits, mice, rats, and humans) using an one or more inventive nucleic acid molecules (e.g., a DNA molecule that encodes an RNA molecule that comprises one or more RNA core molecules or an LNA which comprises one or more RNA core molecules) include, but are not limited to lysosomal storage diseases (LSD), neurological LSDs, inherited neurological LSDs, Fabry Disease, Gaucher Disease, Hurler syndrome (severe MPS I), Lysosomal Acid Lipase Deficiency, Mucopolysaccharidosis Type I (MPS I), Mucopolysaccharidosis Type II (MPS II), Mucopolysaccharidosis Type III (MPS III, such as MPS IIIA, MPS IIIB, MPS IIIC, or MPS IIID), Mucopolysaccharidosis Type IV (MPS IV), Mucopolysaccharidosis Type VI (MPS VI), Mucopolysaccharidosis Type VII (MPS VII), Neuronal Ceroid Lipofuscinosis, Niemann-Pick disease, Pompe disease, Sandhoff's disease, Tay-Sachs, metachromatic leukodystrophy, Thrombocytopenia, neurodegenerative diseases, Alzheimer's disease, Parkinson disease, Huntington disease, cancers, tumors associated with cancers, acute myeloid leukemia (AML), HPV associated cancers, multiple myeloma, lymphoma, leukemia, bone marrow cancer, non-Hodgkin lymphoma (e.g., diffuse large B-cell lymphoma), glioblastoma multiforme, endometrial cancer, melanoma, prostate cancer, lung cancer, breast cancer, kidney cancer, chemotherapy resistant cancers, bladder cancer, urothelial cancer, renal cancer, basal cell carcinoma, thyroid cancer, squamous cell carcinoma, neuroblastoma, ovarian cancer, renal cell carcinoma, hepatocellular carcinoma, HPV associated cancers, colon cancer, pancreatic cancer, chronic lymphocytic leukemia (CLL), acute lymphoblastic leukemia, rhabdomyosarcoma, meningioma, gastric cancer, Glioma, oral cancer, nasopharyngeal carcinoma, rectal cancer, stomach cancer, cancer metastasis, or uterine cancer. In some embodiments, diseases that can be treated can include lysosomal storage diseases (LSD), neurological LSDs, inherited neurological LSDs, Fabry Disease, Gaucher Disease, Hurler syndrome (severe MPS I), Lysosomal Acid Lipase Deficiency, Mucopolysaccharidosis Type I (MPS I), Mucopolysaccharidosis Type II (MPS II), Mucopolysaccharidosis Type III (MPS III, such as MPS IIIA, MPS IIIB, MPS IIIC, or MPS IIID), Mucopolysaccharidosis Type IV (MPS IV), Mucopolysaccharidosis Type VI (MPS VI), Mucopolysaccharidosis Type VII (MPS VII), Neuronal Ceroid Lipofuscinosis, Niemann-Pick disease, Pompe disease, Sandhoff's disease, metachromatic leukodystrophy, Tay-Sachs, Thrombocytopenia, neurodegenerative diseases, Alzheimer's disease, Parkinson disease, or Huntington disease. In some embodiments, diseases that can be treated can include lysosomal storage diseases (LSD), neurological LSDs, inherited neurological LSDs, Fabry Disease, Hurler syndrome (severe MPS I), Lysosomal Acid Lipase Deficiency, Mucopolysaccharidosis Type I (MPS I), Mucopolysaccharidosis Type II (MPS II), Mucopolysaccharidosis Type III (MPS III, such as MPS IIIA, MPS IIIB, MPS IIIC, or MPS IIID), Mucopolysaccharidosis Type IV (MPS IV), Mucopolysaccharidosis Type VI (MPS VI), Mucopolysaccharidosis Type VII (MPS VII), Neuronal Ceroid Lipofuscinosis, Pompe disease, Sandhoff's disease, metachromatic leukodystrophy, Thrombocytopenia, neurodegenerative diseases, Alzheimer's disease, Parkinson disease, or Huntington disease. In certain embodiments, diseases that can be treated can include LSDs, neurological LSDs, neurodegenerative diseases, Hurler syndrome, or MPS I.

Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or a lysosomal storage disease). In some embodiments, the age of the animal (e.g., mammal, human, or mouse) can be about 1 month, about 2 months, about 3 months, about 4 months, about 5 months, about 6 months, about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 30 years, about 40 years, about 50 years, about 60 years, about 70 years, about 80 years, about 90 years, about 100 years, no more than about 2 months, no more than about 3 months, no more than about 1 year, no more than about 2 years, no more than about 3 years, no more than about 4 years, at least about 3 months, at least about 4 months, at least about 6 months, at least about 1 year, at least about 2 years, at least about 3 years, at least about 4 years, at least about 5 years, at least about 10 years, at least about 20 years, at least about 50 years, or at least about 70 years. In other embodiments, the age of the animal (e.g., human) can be at least about 1 year, at least about 2 years, at least about 3 years, at least about 4 years, at least about 5 years, or at least about 10 years.

In some embodiments, the animal is at least about two months, at least about three months, at least about four months, at least about six months, at least about one year, at least about two years, at least about three years, at least about five years, or at least about ten years. In other embodiments, the animal is a human and the age of the animal is at least about six months, at least about one year, at least about two years, at least about three years, at least about five years, or at least about ten years. In other embodiments, the animal is a human and the age of the animal is at least about three years, at least about five years, or at least about ten years. In yet other embodiments, the animal is a rodent (e.g., mouse or a rat) and the age of the animal is at least about two months, at least about three months, at least about four months, at least about six months, or at least about one year. In yet other embodiments, the animal is a rodent (e.g., mouse or a rat) and the age of the animal is at least about four months, at least about six months, or at least about one year.

In some embodiments, diseases (e.g., LSDs, neurological LSDs, neurodegenerative diseases, Hurler syndrome, cancer, or MPS I) that can be treated in an animal (e.g., mammals, porcine, canine, avian (e.g., chicken), bovine, feline, primates, rodents, monkeys, rabbits, mice, rats, and humans) using one or more inventive nucleic acid molecules (e.g., a DNA molecule that encodes an RNA molecule that comprises one or more RNA core molecules or an LNA which comprises one or more RNA core molecules) include, but are not limited to diseases (e.g., LSDs, neurological LSDs, neurodegenerative diseases, Hurler syndrome, cancer, or MPS I) that can be treated by decreasing miR-143 activity/levels in a cell, increasing M6RP concentration in a cell, increasing M6RP expression in a cell, increasing M6RP activity in a cell, increasing β-hexosaminidase amounts/activities/expression (e.g., in one or more organs/tissues and/or in circulation), decreasing β-hexosaminidase amounts/activities/expression (e.g., in one or more organs/tissues and/or in circulation), normalizing β-hexosaminidase amounts/activities/expression (e.g., in one or more organs/tissues and/or in circulation), increasing the levels of protein of interest that reach the brain parenchyma (e.g. CNS), rectifying the CNS lesions resulting from the implementation of prior treatments (e.g., enzyme replacement therapy (ERT)), or a combination thereof.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating diseases (e.g., LSDs, neurological LSDs, neurodegenerative diseases, Hurler syndrome, cancer, or MPS I), treating can include but is not limited to prophylactic treatment and therapeutic treatment. As such, treatment can include, but is not limited to: preventing disease (e.g., LSDs, neurological LSDs, neurodegenerative diseases, Hurler syndrome, cancer, or MPS I); ameliorating or relieving symptoms of disease (e.g., LSDs, neurological LSDs, neurodegenerative diseases, Hurler syndrome, cancer, or MPS I); inhibiting the development or progression of disease (e.g., LSDs, neurological LSDs, neurodegenerative diseases, Hurler syndrome, cancer, or MPS I); reducing the severity of disease (e.g., LSDs, neurological LSDs, neurodegenerative diseases, Hurler syndrome, cancer, or MPS I) or one or more of the symptoms associated with disease (e.g., LSDs, neurological LSDs, neurodegenerative diseases, Hurler syndrome, cancer, or MPS I) (e.g., a decrease in the amount of IDUA); or causing remission of disease (e.g., LSDs, neurological LSDs, neurodegenerative diseases, Hurler syndrome, cancer, or MPS I). In some embodiments, treating does not include prophylactic treatment of disease (e.g., LSDs, neurological LSDs, neurodegenerative diseases, Hurler syndrome, cancer, or MPS I) (e.g., preventing or ameliorating future disease (e.g., LSDs, neurological LSDs, neurodegenerative diseases, Hurler syndrome, cancer, or MPS I)).

Treatment of an animal (e.g., human) can occur using any suitable administration method (such as those disclosed herein) and using any suitable amount of one or more inventive nucleic acid molecules (e.g., a DNA molecule that encodes an RNA molecule that comprises one or more RNA core molecules or an LNA which comprises one or more RNA core molecules). In some embodiments, methods of treatment comprise treating an animal for disease (e.g., LSDs, neurological LSDs, neurodegenerative diseases, Hurler syndrome, cancer, or MPS I). Some embodiments of the invention include a method for treating a subject (e.g., an animal such as a human or primate) with a composition comprising one or more inventive nucleic acid molecules (e.g., a DNA molecule that encodes an RNA molecule that comprises one or more RNA core molecules or an LNA which comprises one or more RNA core molecules) (e.g., a pharmaceutical composition) which comprises one or more administrations of one or more such compositions; the compositions may be the same or different if there is more than one administration.

In some embodiments, the method of treatment includes administering an effective amount of a composition comprising one or more inventive nucleic acid molecules (e.g., a DNA molecule that encodes an RNA molecule that comprises one or more RNA core molecules or an LNA which comprises one or more RNA core molecules). As used herein, the term "effective amount" refers to a dosage or a series of dosages sufficient to affect treatment (e.g., to treat disease, such as for example, LSDs, neurological LSDs, neurodegenerative diseases, Hurler syndrome, or MPS I) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of one or more inventive nucleic acid molecules (e.g., a DNA molecule that encodes an RNA molecule that comprises one or more RNA core molecules or an LNA which comprises one or more RNA core molecules) (which can be administered to an animal such as mammals, primates, monkeys or humans) can be an amount of about 0.005 to about 50 mg/kg body weight, about 0.005 to about 80 mg/kg body weight, about 0.005 to about 100 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In regard to some embodiments, the dosage can be about 0.5 mg/kg human body weight, about 5 mg/kg human body weight, about 6.5 mg/kg human body weight, about 10 mg/kg human body weight, about 50 mg/kg human body weight, about 80 mg/kg human body weight, or about 100 mg/kg human body weight. In some instances, an effective amount of one or more inventive nucleic acid molecules (e.g., a DNA molecule that encodes an RNA molecule that comprises one or more RNA core molecules or an LNA which comprises one or more RNA core molecules) (which can be administered to an animal such as mammals, rodents, mice, rabbits, feline, porcine, or canine) can be an amount of about 0.005 to about 50 mg/kg body weight, about 0.005 to about 100 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, an effective amount of one or more inventive nucleic acid molecules (e.g., a DNA molecule that encodes an RNA molecule that comprises one or more RNA core molecules or an LNA which comprises one or more RNA core molecules) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In regard to some conditions, the dosage can be about 5 mg/kg human body weight, about 10 mg/kg human body weight, about 20 mg/kg human body weight, about 80 mg/kg human body weight, or about 100 mg/kg human body weight. In some instances, an effective amount of one or more inventive nucleic acid molecules (e.g., a DNA molecule that encodes an RNA molecule that comprises one or more RNA core molecules or an LNA which comprises one or more RNA core molecules) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 80 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg.

"Therapeutically effective amount" means an amount effective to achieve a desired and/or beneficial effect (e.g., increasing IDUA in the CNS). A therapeutically effective amount can be administered in one or more administrations. For some purposes of this invention, a therapeutically effective amount is an amount appropriate to treat an indication (e.g., to treat disease, such as for example, LSDs, neurological LSDs, neurodegenerative diseases, Hurler syndrome, cancer, or MPS I). By treating an indication is meant achieving any desirable effect, such as one or more of palliate, ameliorate, stabilize, reverse, slow, or delay disease (e.g., LSDs, neurological LSDs, neurodegenerative diseases, Hurler syndrome, cancer, or MPS I) progression, increase the quality of life, or to prolong life. Such achievement can be measured by any suitable method, such as but not limited to measurement of the amount of miR-143 in the cell, the miR-143 activity in the cell, the M6RP concentration in a cell, the M6RP expression in a cell, the M6RP activity in a cell, the β-hexosaminidase amount (e.g., in one or more organs/tissues and/or in circulation), the β-hexosaminidase activity (e.g., in one or more organs/tissues and/or in circulation), the extent of rectifying the CNS lesions resulting from the implementation of prior treatments (e.g., enzyme replacement therapy (ERT)), the BBB permeability of one or more proteins, the BBB permeability of one or more lysosomal proteins (e.g., IDUA), the IDUA concentration in the CNS, the IDUA activity in the CNS, the extent of one or more CNS abnormalities caused by an LSD, the accumulation of substrates (e.g., glycosaminoglycans (GAGs)) in one or more bodily tissues, or the reduction or cancer growth or metastasis.

In some embodiments, other treatments of disease (e.g., LSDs, neurological LSDs, neurodegenerative diseases, Hurler syndrome, cancer, or MPS I) are optionally included, and can be used with the inventive treatments described herein (e.g., administering one or more inventive nucleic acid molecules (e.g., a DNA molecule that encodes an RNA molecule that comprises one or more RNA core molecules or an LNA which comprises one or more RNA core molecules)). Other treatments of disease (e.g., LSDs, neurological LSDs, neurodegenerative diseases, Hurler syndrome, cancer, or MPS I) can include any known treatment that is suitable to treat the disease (e.g., LSDs, neurological LSDs, neurodegenerative diseases, Hurler syndrome, cancer, or MPS I). Examples of known LSD treatments include but are not limited to allogeneic hematopoietic stem cell transplantation, enzyme replacement therapy by periodic injection of recombinant enzyme or gene therapy, or enhanced delivery of protein (e.g., IDUA) across the BBB by fusion protein targeted delivery (e.g., via fusion with an apoE or apoB receptor binding region) (see, US Pat. Appl. Pub. No. 2014/0219974 A1 dated Aug. 7, 2014 to Pan, which is herein incorporated by reference in its entirety).

In some embodiments, administration of a vector that does not comprise the inventive nucleic acid molecule but that does comprise a protein to be transported across the BBB, can be used as part of the treatment regime (i.e., in addition to administration of one or more inventive nucleic acid molecules (e.g., a DNA molecule that encodes an RNA molecule that comprises one or more RNA core molecules or an LNA which comprises one or more RNA core molecules) and as an other disease treatment); administration of a vector that does not comprise the inventive nucleic acid molecule but that does comprise a protein to be transported across the BBB, can include separate administrations (i.e., in a separate composition from the inventive nucleic acid molecule) or can be added to the composition comprising the inventive nucleic acid molecules (e.g., a DNA molecule that encodes an RNA molecule that comprises one or more RNA core molecules or an LNA which comprises one or more RNA core molecules). In certain embodiments, the protein is a lysosomal protein, IDUA, iduronate-2-sulfatase, heparan N-sulfatase, N-acetyl-alpha-D-glucosaminidase, acid alpha-glucosidase, arylsulfatase A, or a protein that can be transported via M6PR (e.g., a protein that has been modified with mannose-6-phosphate residues to use a transport pathway via M6PR).

In some embodiments, additional optional treatments (e.g., as an other disease treatment) can also include one or more of surgical intervention, hormone therapies, immunotherapy, and adjuvant systematic therapies.

The presently-disclosed subject matter is further illustrated by the following specific but non-limiting examples. The following examples may include compilations of data that are representative of data gathered at various times during the course of development and experimentation related to the present invention.

EXAMPLES

Materials and Methods

Cell lines and animals. Human umbilical vein cell (HUVEC) and human brain endothelial cell line (hCMEC/D3) were routinely maintained in endothelial growth medium 2-MV (EGM-2 MV, Lonza), which consists of endothelial basal medium-2 (EBM-2), 5% fetal bovine serum (FBS), and the supplemental growth factors VEGF, bFGF, epidermal growth factor, and insulin-like growth factor in concentrations as suggested by the manufacturer. miR-143 knock out mice (miR-143KO) on the background of C57BL/6 were generated and kindly provided by Dr. Mei Xin (Cincinnati Children's Hospital Medical Center, CCHMC) (XIN et al. "MicroRNAs miR-143 and miR-145 modulate cytoskeletal dynamics and responsiveness of smooth muscle cells to injury" Genes & development (2009) Vol. 23, No. 18, pp. 2166-2178.). The MPS I mice model (Idua$^{-/-}$ mice, C57BL/6 background) was purchased from the Jackson Laboratory. The MPS I/miR-143KO (MPS I/143KO) breeding colony was established from heterozygous mating pairs, and genotyping was performed on ear clip DNA. All animal procedures were approved by Institutional Animal Care and Use Committee of CCHMC.

Brain microvasculature isolation. Murine cerebral microvessels were isolated as previously reported with modifications (BANKS et al. "Transport of human immunodeficiency virus type 1 pseudoviruses across the blood-brain barrier: role of envelope proteins and adsorptive endocytosis." Journal of virology (2001) Vol. 75, No. 10, pp. 4681-4691.). Briefly, 8~12 well perfused cerebral cortexes (reagent volumes may be proportionately adjusted for number of brains used) were pooled and emulsified in stock buffer [25 mM HEPES, 1% dextran (Mw ~70,000, Sigma) in minimum essential medium] on ice with a glass tissue grinder (20 strokes), which has been coated with 1% BSA-PBS to minimize adhesion. After homogenization, the even mixture was filtered through 200 µm (1×), 100 µm (2×) nylon mesh (Fisher scientific), then mixed with equal volume of 40% dextran in stock buffer followed by centrifugation at 3,500 g for 15 min at 4° C. The myelin layer was collected as capillary depleted brain (CDB). The pellet was collected and suspended in stock buffer and filtered through 25 µm nylon mesh (Biodesign Inc.). The microvessels were washed from the surface of the membrane with stock buffer and centrifuged at 5,000 g for 15 min at 4° C. Cell pellets were collected as brain microvessel (BrMV).

MicroRNA Microarray Analysis. miRNA-enriched fraction (<200nt) from BrMV of adult and postnatal day 9-14 mice were isolated using the miRNeasy Kit (Qiagen). As described (GUO et al. "Differential expression of microRNA species in human gastric cancer versus non-tumorous tissues." Journal of gastroenterology and hepatology (2009) Vol. 24, No. 4, pp. 652-657; LIN et al. "Characterization of microRNA expression profiles and the discovery of novel microRNAs involved in cancer during human embryonic development" PLOS ONE (2013) Vol. 8, No. 8, Article No. e69230 (11 pages).), microarray was performed by sample hybridization on a µParaflo™ microfluidic chip (LC Sciences), which detects 1265 murine mature miRNA transcripts listed in Sanger miRBase Release 19.0 (<<www.mirbase.org>>). Data were normalized and analyzed by service provider (LC sciences). All pooled BrMV from either the same WT littermate (adult, 8-12 mice) or two litters (10-16 pups) was considered as a biological replicate. Two biological replicates were used and each sample represents isolation from different litter(s) performed on different dates.

Quantification of miRNAs/mRNAs with real-time PCR. In general, total RNA from BrMV or cell lines was extracted by RNeasy Kit (Qiagen) according to the manufacturer's manual. For quantification of mature miR-143 and miR-145a, TaqMan MicroRNA assays (Invitrogen) was used as previously described (SLABY et al. "Altered expression of miR-21, miR-31, miR-143 and miR-145 is related to clinicopathologic features of colorectal cancer." Oncology (2007) Vol. 72, Nos. 5-6, pp. 397-402; TAVAZOIE et al. "Endogenous human microRNAs that suppress breast cancer metastasis." Nature (2008) Vol. 451, No. 7175, pp. 147-152.). Briefly, cDNA was synthesized using miRNA-specific (stem-looped) primers followed by the recommendations of TaqMan MicroRNA Reverse Transcription kit (Invitrogen). PCR reactions were performed in triplicate and each 20 µl reaction contains 10 µl 2× TaqMan Universal PCR Master Mix (Invitrogen), 1 µl reverse transcription product, 1 μl of TaqMan primers and probe mix (20×). Reactions were incubated in a 96-well optical plate at 95° C. for 10 min, followed by 40 cycles of 95° C. for 15 s and 60° C. for 1 min. For M6PR, MECA32 mRNA quantification, cDNA was similarly generated by using a High Capacity cDNA Reverse Transcription kit (ThermoFisher). Real-time PCR were performed by using: for human M6PR mRNA, sense 5'-GAGCTACGCTCATCACCTTTCTC-3' (SEQ ID NO:26), antisense 5'-TGGTGTACCACCGGAAGTTGT-3' (SEQ ID NO:27); for mouse M6PR mRNA, sense 5'-CACACTGATTACCTTCCTCTGTGA-3' (SEQ ID NO:28); antisense 5'-GGTGTACCACCGGAAGTTGTAG-3' (SEQ ID NO:29) and common probe 5'-FAM-ATATCAG-GAAGAGGACAACT-3' (SEQ ID NO:30). U6 snRNA was used as an endogenous control for miRNA expression analysis, while Actb or Gapdh (Invitrogen) were served as internal controls for mRNA quantification or Western blot analysis.

UTR reporter assay. An M6PR 3' UTR fragment (1304 bp, wild type)(SEQ ID NO:31)(see also full 3'UTR at SEQ ID NO:35) containing predicted miR-143 binding sites was amplified from mouse genomic DNA and cloned into the pEZX-MT01 dual Firefly/*Renilla* luciferase reporter vector (GeneCopoeia). (a portion of the last exon of murine M6PR with the three binding sites is SEQ ID NO:32—see also SEQ ID NO:36 for the full sequence of the last exon of murine M6PR) Meanwhile, the seed region in each predicted binding site was mutated to remove all complementarity to the first 1-7 (site 1) or 2-8 nt (site 2 and 3) of miR-143 using the QuikChange Site-Directed Mutagenesis (Stratagene) to generate single mutants Mut1 (see FIGS. 2A and 2B), Mut2 (see FIGS. 2A and 2B), and Mut3 (see FIGS. 2A and 2B) and triple mutant Mut123 (see FIGS. 2A and 2B). Both wild type and mutant 3'UTRs were co-transfected with or without cytomegalovirus (CMV)-driven miR-143 or 145a overexpression constructs (pCMV6-miR-143 or pCMV6-miR-145a) into HEK 293T cells in 12-well plate using lipofectamine 2000 (Invitrogen). Cells were lysed 48 hours after transfection, the ratios between Firefly luciferase and *Renilla* luciferase activity were determined with a dual-luciferase assay system (Promega). *Renilla* luciferase was used as an internal control for normalization of transfection efficacy.

Manipulation of miR-143 in human vascular endothelial cells. We generated miR-143 sponge vector by taking advantage of antagomir and bulged miRNA sponge designing which have been described previously (SCHERR et al. "Lentivirus-mediated antagomir expression for specific inhibition of miRNA function." Nucleic acids research (2007) Vol. 35, No. 22, Article e149 (9 pages); EBERT et al. "MicroRNA sponges: competitive inhibitors of small RNAs in mammalian cells." Nature methods (2007) Vol. 4, No. 9, pp. 721-726.). Oligonucleotides (sense, 5'-CTAGAGAGC-TACAGACGTCATCT CACGATGAGCTACAGTG-GATCCTTCATCTCAT-3' (SEQ ID NO:33); antisense, 5'-CTAGATGAGATGAAG GATCCACTGTAGCT-CATCGTGAGATGACGTCTGTAGCTCT-3' (SEQ ID NO:34)) for one bulged miR-143 binding site as well as one perfect site with a 4-nt spacer were annealed, ligated and cloned into a Xba I linearized LV backbone LV-TW (EL-AMOURI et al., "Normalization and improvement of CNS deficits in mice with hurler syndrome after long-term peripheral delivery of BBB-targeted iduronidase" Molecular Therapy: The Journal of the American Society of Gene Therapy (2014) Vol. 22, No. 12, pp. 2028-2037; WOR-SHAM et al., "In vivo gene transfer into adult stem cells in unconditioned mice by in situ delivery of a lentiviral vector." Molecular Therapy: The Journal of the American Society of Gene Therapy (2006) Vol. 14, No. 4, pp. 514-524.) at the downstream of green fluorescent protein (GFP), which was driven by an SFFV promoter and served as an indicator for cell sorting. Sequencing data shows four unidirectional inserts, in total 8 miR-143 binding sites, were merged at downstream of GFP. For overexpression of miR-143, a CMV-miR-143 cassette was amplified from pCMV6-miR-143 vector and constructed into the same LV backbone. Lentivirus was generated by 4-plasmid packaging system and concentrated through ultracentrifugation, as previously described (WANG et al., "Co-expression of MGMT(P140K) and alpha-L-iduronidase in primary hepatocytes from mucopolysaccharidosis type I mice enables efficient selection with metabolic correction." The Journal of Gene Medicine (2008) Vol. 10, No. 3, pp. 249-259.). Virus particles were then used to transduce HUVEC and hCMEC/D3 in the presence of 8 μg/mL polybrene (Sigma). GFP positive cells were selected through fluorescence activated cell sorting (FACS). MiR-143 expression was confirmed in all cases using quantitative TaqMan PCR.

Binding and internalization of IDUA enzyme in vascular cells. Binding and internalization of IDUA enzyme was performed as previously described with modifications (WANG et al. "Engineering a lysosomal enzyme with a derivative of receptor-binding domain of apoE enables delivery across the blood-brain barrier." Proceedings of the National Academy of Sciences of the United States of America (2013) Vol. 110, No. 8, pp. 2999-3004.). Briefly, virus transduced vascular endothelial cells ($5 \times 10^5$ per well) were seeded in 12-well plates. Twenty-four hours later, mannose 6-phosphate (M6P, 1,500 μM; Sigma) was added to specifically inhibit M6PR mediated uptake 30 min before and during the incubation. Treated or untreated cells were then exposed at 4° C. for 20 min to enzyme containing EGM-2 medium (~20,000 U/mL), which was generated in HEK 293-based cells that can stalely overexpress IDUA. Cells were then cultured in fresh medium at 37° C. for 1 h after multiple washes with PBS. IDUA activity in cell lysates was assayed as described (WANG et al. "Engineering a lysosomal enzyme with a derivative of receptor-binding domain of apoE enables delivery across the blood-brain barrier." Proceedings of the National Academy of Sciences of the United States of America (2013) Vol. 110, No. 8, pp. 2999-3004.). Each experiment group was performed in triplicate. Net endocytosed IDUA was calculated by subtracting the endogenous IDUA in each cell line.

M6PR (also known as IGF2R), LAMP2 antibody (ab) internalization assay. Freshly isolated BrMV from WT (n=8) or miR-143KO (n=8) was incubated with warm serum free EGM-2 basic medium without growth factor. Internalization was performed by adding 1.8 μg/mL rabbit anti-M6PR (Cell Signal Technology) alone or together with 10 μg/mL rat anti-LAMP2 (Abcam) at 37° C. for 1 h. Cells were then washed and cyto-spun onto glass slides at speed of 1,000 rpm for 5 min After fixation in 4% PFA for 30 min and permeabilized with 0.3% Triton X-100/PBS, slides were blocked and incubated with primary Ab (LAMP2, if not used in internalization step) or secondary Ab and Lectin (fluorescein labeled Lycopersicon Esculentum Lectin; Vector Laboratories). After multiple washes, slides were mounted with Vectashield antifade medium containing DAPI (Vector Laboratories). Micrographs were obtained on an inverted fluorescence microscope Nikon Ti-E equipped with a 60× oil immersion objective lens and an additional 1.5× digital zoom was applied.

Short-term in vivo gene transfer by hydrodynamic tail vein injection. A total of 50 μg of the IDUA-3'myc expressing plasmid from a liver-specific promoter were i.v. injected into the tail vein of 6 wk-old MPS I or MPS I/miR-143KO mice in a volume of 0.9% NaCl solution equivalent to 10% (vol/wt) of body mass over a period of 5-8 s by using a 26-gauge insulin syringe (ThermoFisher). Mice were monitored for 5 min after the injection to ensure the recovery to normal activity. Mice were bled periodically (day 1 and day 2) from the tail vein to monitor plasma IDUA activity. Forty-eight hours after injection, mice were anesthetized by i.p. injection with pentobarbital (Abbott Laboratories) and transcardially perfused with cold PBS as previously described (WANG et al. "Engineering a lysosomal enzyme with a derivative of receptor-binding domain of apoE enables delivery across the blood-brain barrier." Proceedings of the National Academy of Sciences of the United States of America (2013) Vol. 110, No. 8, pp. 2999-3004; WATSON et al., "Intrathecal administration of AAV vectors for the treatment of lysosomal storage in the brains of MPS I mice." Gene Therapy (2006) Vol. 13, No. 11, pp. 917-925.) to minimize the effect of blood IDUA on brain enzyme levels.

Quantification of α-L-Iduronidase and β-hexosaminidase. The catalytic activity of α-L-Iduronidase (IDUA) or β-hexosaminidase (β-hex) was determined as previously described (WANG et al., "Co-expression of MGMT(P140K) and alpha-L-iduronidase in primary hepatocytes from mucopolysaccharidosis type I mice enables efficient selection with metabolic correction." The Journal of Gene Medicine (2008) Vol. 10, No. 3, pp. 249-259; ZHENG et al., "Treatment of the mouse model of mucopolysaccharidosis I with retrovirally transduced bone marrow." Molecular Genetics and Metabolism (2003) Vol. 79, No. 4, pp. 233-244.) with modifications. For the IDUA assay, cells or an aliquot of CDB derived from brain parenchyma was homogenized and ultrasonicated in lysis buffer (150 mM NaCl and 50 mM Tris-HCl with 1% Triton X-100). 10 µl of cleared lysate, plasma, or culture medium were reacted with 25 µl of 2.5 mM fluorogenic substrate (4-methy-lumbelliferyl (4MU) α-L-idopyranosiduronic acid sodium salt; Toronto Research Chemicals) in 0.4 M of sodium formate buffer (pH 3.2) at 37° C. for 1 h. To stop the reaction, 1 mL of 0.1 M glycine carbonate buffer (pH 11.0) was added. For determination of β-hexosaminidase activity, the corresponding CDB aliquot used in the IDUA assay was homogenized in 150 mM NaCl solution containing 1% Triton X-100, followed by dilution (1:250 and 1:500) in distilled water. The diluted homogenates (10 µl) were incubated with 10 µl of 1.2 mM 4MU-β-N-acetylglucosaminide (Sigma) in 10 mM citrate/20 mM phosphate buffer, pH 4.5, for 1 h at 37° C. The reaction was stopped by the addition of 0.5 ml of 0.1 M glycine carbonate buffer (pH 11.0). The fluorescent product released in both reactions was detected with using a SpectraMax M2 fluorometer plate reader (MDS Analytical Technologies) at an excitation wavelength of 365 nm and an emission wavelength of 450 nm. In both assays, one unit (U) of enzyme activity is defined as the release of 1 nmol 4MU in a one-hour reaction at 37° C. IDUA or β-hex catalytic activity was presented as U/ml in plasma or medium, or U/protein amount which was determined by Pierce BCA Protein Assay (ThermoFisher) in CDB or cell lysate. All specimens were assayed in duplicate and quantified in quadruplicate wells in parallel with buffer controls.

Quantification of Glycosaminoglycans (GAGs). Dissected cortical parenchyma were homogenized with 10% vol/weight of ice cold water. The raw protein concentration was measured by using Pierce BCA Protein Assay (ThermoFisher). Equivalent amounts of proteins (0.5 mg) per mouse were defatted by incubating with 0.5 ml chloroform:methanol (1:2) solution at RT for 3 h, then washed with 100% ethanol. Pellets was re-suspended and ultrasonicated (40 sec/4 times on ice) in papain buffer (0.1M sodium acetate pH 5.5, 5 mM EDTA, 5 mM L-Cysteine pH 5.5). The second (2°) protein assay was performed by using Bradford protein assay (BioRad). To release the soluble GAGs from cell body, we digested samples with 100 mM papain at 65° C. for 3 hours, followed by DNA digestion through incubation with DNase (1 U/µl) for 30 min at 37° C. Free GAGs in solution were quantified in triplicate by reacting with 1,9-dimethylmethylene blue chloride dye as previously described (BARBOSA et al., "Improved and simple micro assay for sulfated glycosaminoglycans quantification in biological extracts and its use in skin and muscle tissue studies." Glycobiology (2003) Vol. 13, No. 9, pp. 647-653.). OD value of the color reaction was measured at 656 nm by using a SpectraMax M2 fluorometer plate reader. All GAGs values were calculated by comparing with a standard curve generated with heparan sulfate (Sigma), and normalized to the amounts of protein determined in the 2° protein assay.

Immunofluorescence staining. Brains from well perfused mice were dissected and post fixed by immersion in 4% paraformaldehyde (PFA) at 4° C. overnight, cryopreserved in 30% sucrose (wt/vol) and frozen in Tissue-Tek CRYO-OCT (Fisher Scientific). Frozen sections (10 µm), BrMV cytological smears were fixed in 4% PFA and permeabilized in 0.3% Triton X-100 solution and blocked with 5% goat serum before stained with the following primary antibodies: mouse c-Myc antibody (1:50, Santa Cruz Biotechnology), rabbit anti-NeuN (1:100, Cell Signal Technology), Rat anti-CD68 (1:100, Fisher Scientific), rabbit anti-M6PR (1:50) and rat anti-LAMP2 (1:100), followed by incubation with Alexa Fluor 488/568-conjugated secondary antibodies (1:500, Invitrogen) or with fluorescein conjugated Lectin (Vector Laboratories). Slides were mounted with Vectashield DAPI containing medium (Vector Laboratories) and visualized by using a DMI6000 B microscopy system or an inverted fluorescence microscope Nikon Ti-E. For IDUA distribution analysis after HTV, two brain samples with comparable IDUA activities per genotype from three independent experiments were analyzed. The percentage of c-Myc positive neurons (NeuN+) or tissue macrophages (CD68+) were counted and calculated from over 500 NeuN+ or CD68+ cells. For spectrophotometric quantification of M6PR and LAMP2 signal, mean grey density in vascular was measured with ImageJ/Fiji (NIH) by outlining vascular profiles followed lectin staining. Over 100 brain endothelial cells were quantified per genotype and quantification was carried out blind.

Statistical analysis. Quantitative assays were performed in duplicate or triplicate from at least two individual experiments. An unpaired student's t-test (GraphPad Prism 6 Software) was applied for comparison. P values <0.05 were considered as statistically significant.

Results

Identification of the miRNAs Regulating Mannose 6-Phosphate Receptor (M6PR, also known as IGF2R) expression in developing Blood-Brain Barrier (BBB). To directly identify the developmental expression change of M6PR on BBB, we isolated Brain MicroVasculature (BrMV) from adult (n=11, >12 weeks of age) and pups (n=12, 8-10 days of age) Immunoblotting results indicated a 62% decrease of M6PR protein in adult brain compared with pups (FIG. 1A). Meanwhile, M6PR transcript copy number from the same sample pair showed approximately 20% reduction in adult BrMV by real time TaqMan PCR (FIG.

1B). Subtle decline of M6PR transcripts contributing to downregulation of protein suggested that it may potentially involve a posttranscriptional regulation. Therefore, we investigated the changes of miRNAs profile in developing brain capillaries. By using two pairs of BrMVs that showed relatively high and comparative purity from adult and pups (~90% for adult samples and ~75% for pup samples as determined by RT-qPCR analyses for Cldn5 and Pecam1 mRNA levels (data not shown)), we identified 16 miRNAs with >2-fold up-regulation and 7 with down-regulation during the maturation of blood brain barrier (FIG. 1C). In combination of bioinformatic tools including TargetScan (AGARWAL et al., "Predicting effective microRNA target sites in mammalian mRNAs" eLife (2015) Vol. 4, Article e05005 (DOI: 10.7554/eLife.05005.001) (38 pages)) and miRanda (BETEL et al., "The microRNA.org resource: targets and expression" Nucleic acids research (2008) Vol. 36 (Database issue), pp. D149-D153), these differentially expressed miRNAs were crossed over with predicted and conserved M6PR targeting miRNAs in vertebrates. miR-143 came out to be the only overlapped and up-regulated microRNA with presumed targets in M6PR transcripts as depicted in the Venn diagram in FIG. 1D. Further TaqMan PCR confirmed the elevated expression of miR-143 in adult brain (FIG. 1E). Consistent with the coordinated expression of miR-143/145a clusters as polycistronic precursors undergoing posttranscriptional processing, another member, miR-145a, also displayed a comparable expression (FIG. 1E); however, miR-145a is not predicted to target M6PR transcript.

Figure 2:
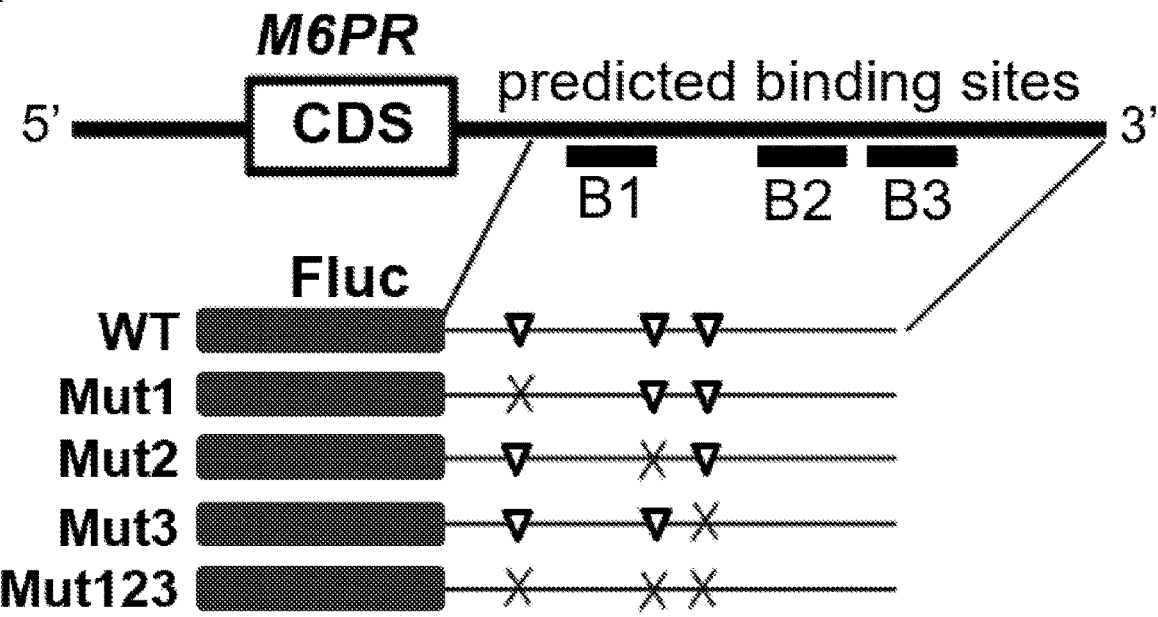
FIG. 2: miR-143 directly regulates M6PR by interacting with its 3'UTR. (A) Schematic diagram of predicted miR-143 binding sites (B1, B2, B3) on 3' UTR of M6PR mRNA and luciferase-based reporter system. UTR fragments containing wild-type binding sites (V) or mutated variants (X) were constructed downstream of firefly luciferase (Fluc). (B) Potential binding pattern of miR-143 (SEQ ID NO:25) to the wild type or mutated M6PR 3'UTRs. Seed sequence of each predicted binding site was shown in numbers on left panels (B1 M6PR 307-313nt (SEQ ID NO:9); B2 M6PR 672-678nt (SEQ ID NO:10); B3 M6PR 826-832nt (SEQ ID NO:11)). Binding region in seed sequence of each site was mutated and highlighted in gray lowercase letters on right panels (Mut1 (SEQ ID NO:41); Mut2 (SEQ ID NO:42); Mut3 (SEQ ID NO:43)). (C) miR-143, not miR-145a, specifically represses luciferase expression. Plasmids expressing Fluc-WT (0.5 µg) alone, or with equal amount of pCMV6-miR-143 or miR-145a overexpressing vectors (0.5 µg) were co-transfected into HEK 293T cells in 12-well plate. Data are shown as the ratio of firefly luciferase/*Renilla* luciferase (Rluc) activity. Rluc serves as internal normalization control for transfection. (D) The reduction of Fluc expression is dose-dependent upon miR-143. (E) miR-143-specific dual luciferase reporter assay. HEK 293T cells were co-transfected with WT or mutated vectors (300 ng) together with miR-143/145a expression construct (1200 ng) in 24-well plate. Data are normalized to Rluc and shown as the mean±SD of three replicates and are representative of two independent experiments. *, p<0.001, , p<0.01, *, p<0.05 by two-tailed t test; ns, not significant.
Figure 2:
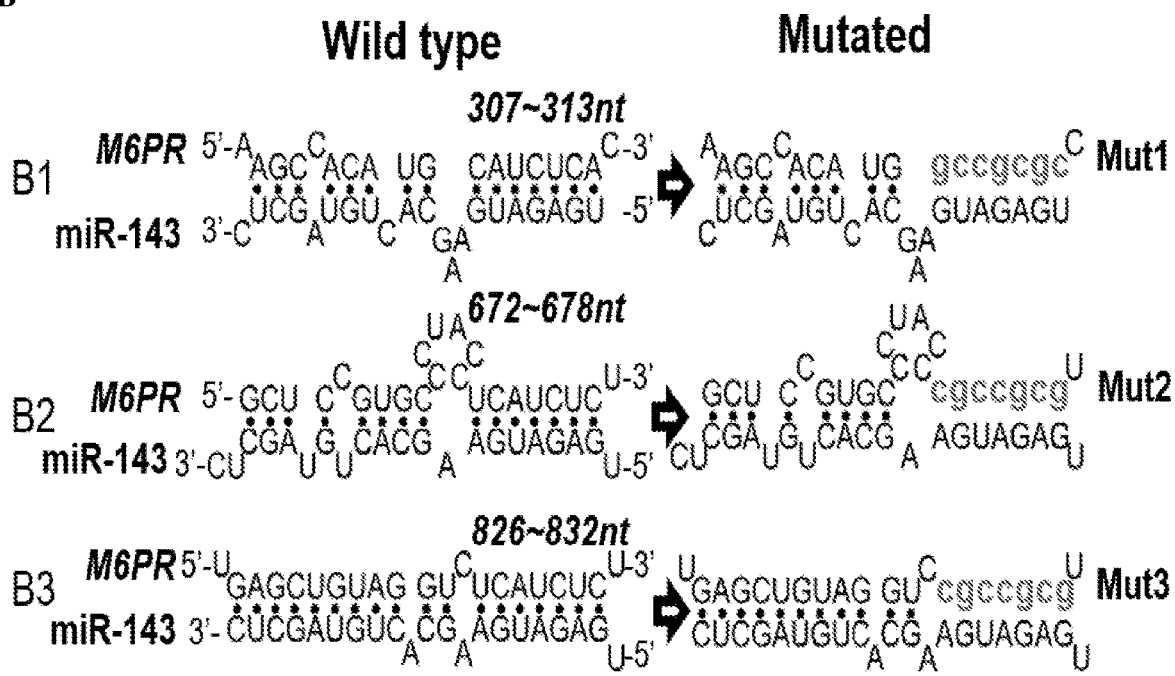
Figure 2:
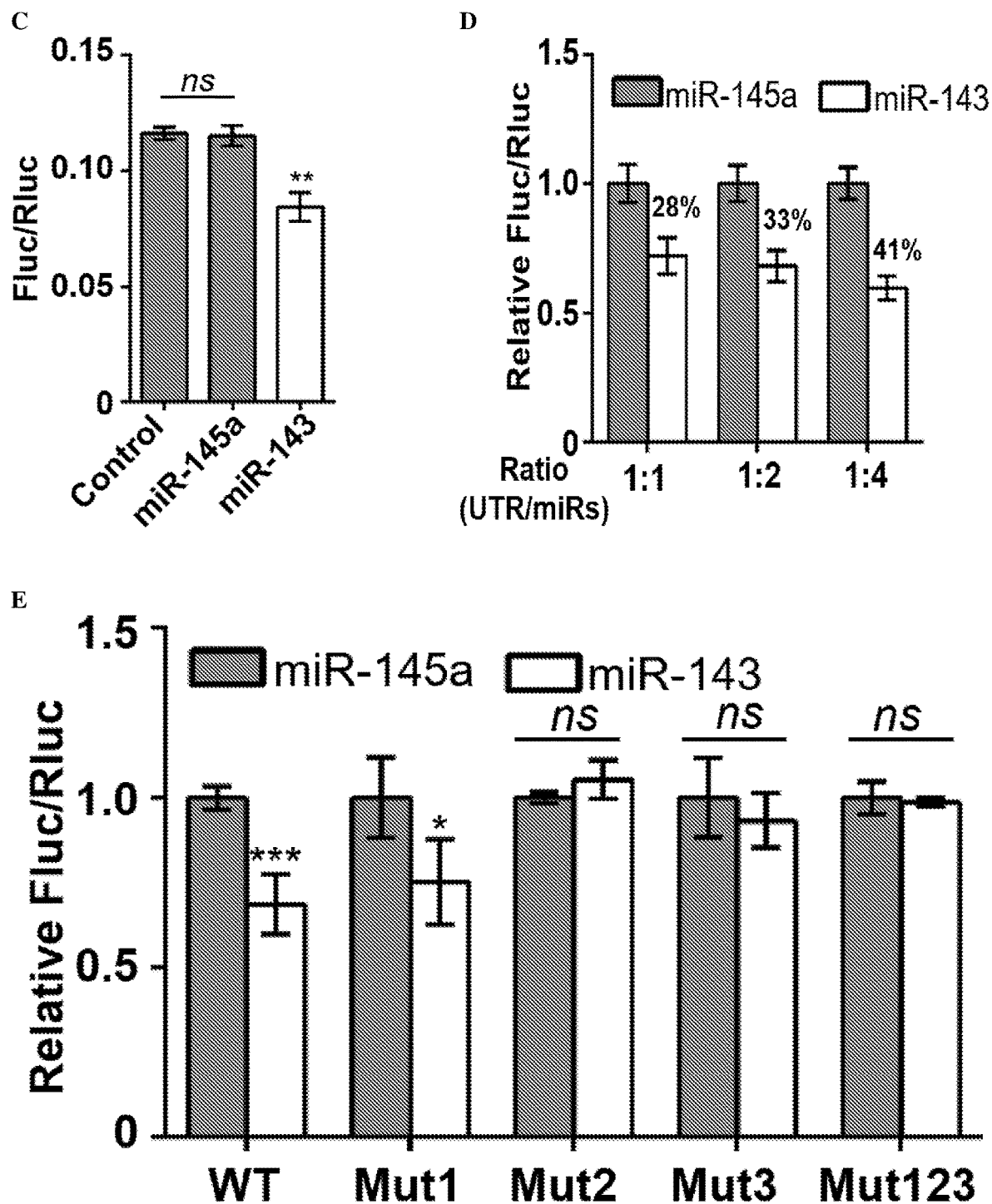
Figure 3:
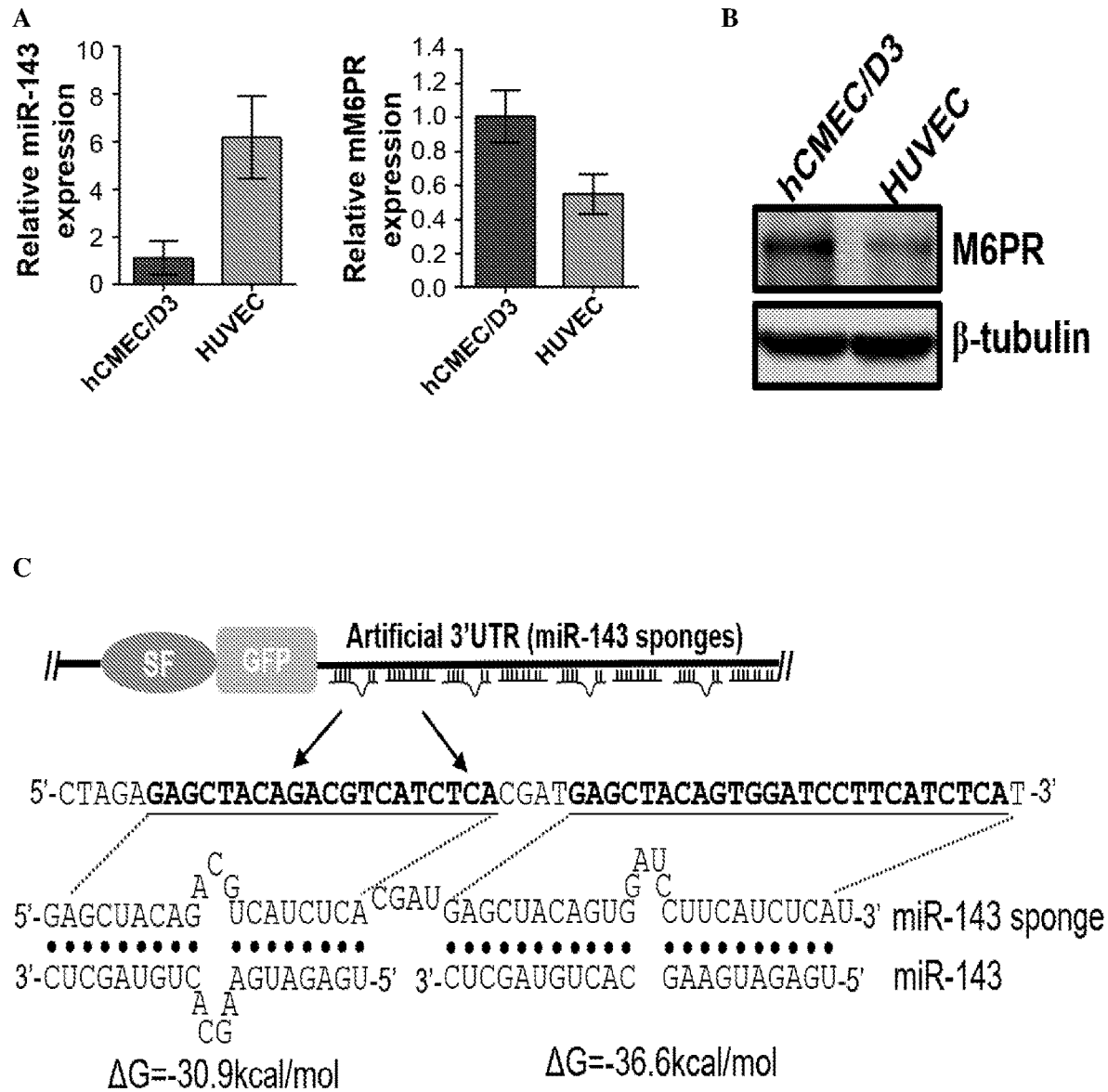
FIG. 3: miR-143 reversely controls M6PR expression and affects M6PR-mediated endocytosis. (A) Relative endogenous expression of mature miR-143 (left panel) and M6PR transcripts (right panel) were determined by TaqMan qPCR using total RNA isolated from two human endothelial cell lines. (B) Western blot shown M6P receptor protein levels in HUVEC and hCMEC/D3 cells. (C) Diagrams of miR-143 sponge designing. Projected bindings of miR143 (SEQ ID NO:25) with sponge sequences are indicated (DNA sequence (SEQ ID NO:33); RNA sequence (SEQ ID NO:44)). (D) Diagrams of lentiviral vectors for knocking down of endogenous miR-143 (LV-143Spg) or overexpression of miR-143 (LV-miR-143). The sponge cluster contains four units of miR-143 binding sites, and each unit consists of a bulged complementary binding site and a perfectly matching site. The sponge sequence was designed as an artificial 3' UTR of GFP which was driven by a SFFV promoter. For overexpression of miR-143, mature miR-143 with ~370 bp flanking sequence was cloned from genome and driven under CMV promoter. (E, F) The knocking down of miR-143 in HUVEC (E) or the overexpression of miR-143 in hCMEC/D3 cells (F) reversely regulates M6PR transcripts and protein expression. Stably transduced cell lines were generated by FACS sorting for GFP cells (>98%) after transduction (MOI=0.5) with either LV-143Spg, LV-miR-143 or the parental GFP-expressing LVs to serve as controls (Control). Relative changes are shown for miR-143 expression (left-panel) and M6PR mRNA (mid-panel) by RT-qPCR, and for M6PR protein by Western blot analysis (right-panel). (G) Mannose 6-Phosphate (M6P) receptor-specific uptake of IDUA-myc fusion proteins in vascular endothelial cells. Inhibitory uptake was detected in HUVEC and hCMEC/D3 cells by M6P competition, suggesting M6PR-mediated specific uptake. Cells were exposed for 1 h to the IDUA-myc conditioned medium (~20,000 U/mL) in the presence of various concentration of M6P inhibitor as indicated. Data were derived from two experiments, each performed in duplicate wells. Median inhibitory concentration ($IC_{50}$) is significantly higher in HUVEC (347.5 µM) than in hCMEC/D3 cells (57.2 µM). This data indicated that hCMEC/D3 cells were much more sensitive to M6P inhibitor than HUVEC ($IC_{50}$ 57.2 µM vs 347.5 µM, FIG. 3G). The significant levels of M6PR-independent uptake in HUVEC cells (plateau at ~18%) could be derived from pinocytotic events that are more frequent in HUVEC, a non-brain originated endothelial cell line. (H, I) Changes in M6PR-mediated IDUA uptake by binding and internalization assays. Transduced HUVEC or hCMEC/D3 cells were exposed to IDUA containing medium (~20,000 U/mL) with or without M6P inhibitor (1500 µM) at 4° C. for 20 mins. to allow binding, and followed by culturing in fresh medium at 37° C. for 1 hour for endocytosis. Variations of intracellular IDUA specific activities are presented as fold changes of control cells. Data were derived from two independent experiments in duplicate or triplicate wells. In all bar graphs, data are shown as mean±SEM; *p<0.05,  p<0.01, *p<0.001 by two-tailed t test.
Figure 3:
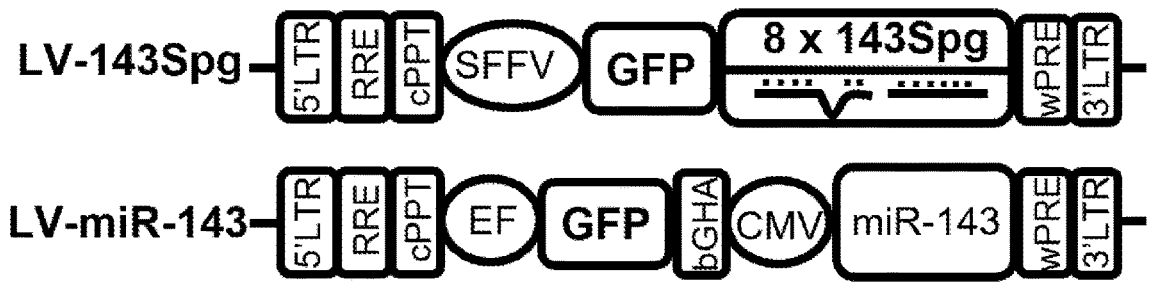
Figure 3:
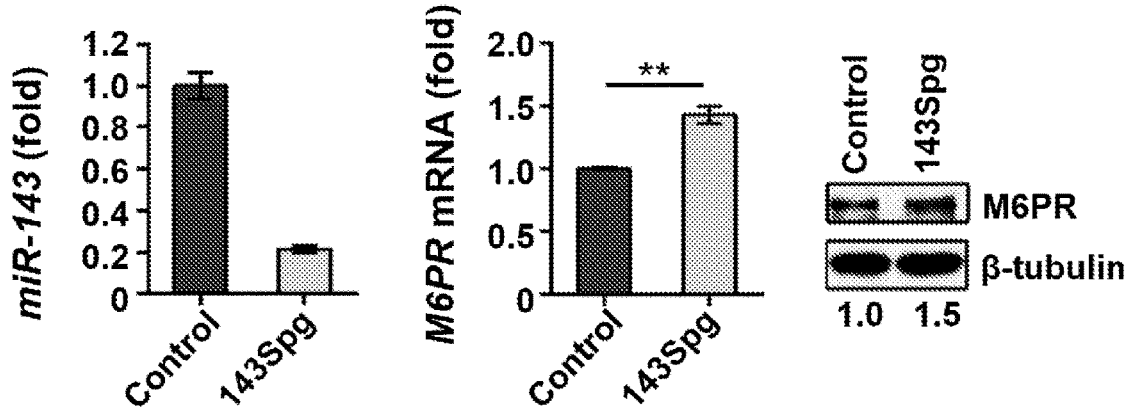
Figure 3:
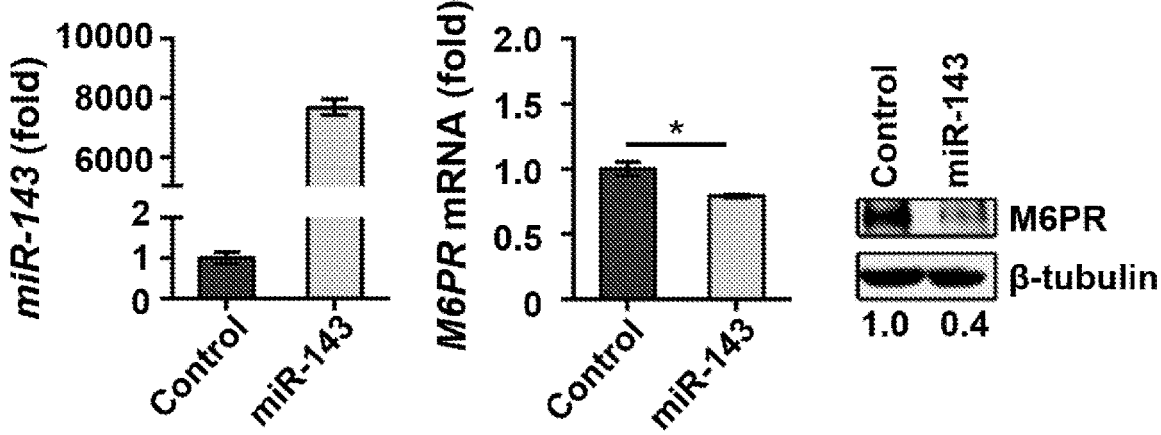
Figure 3:
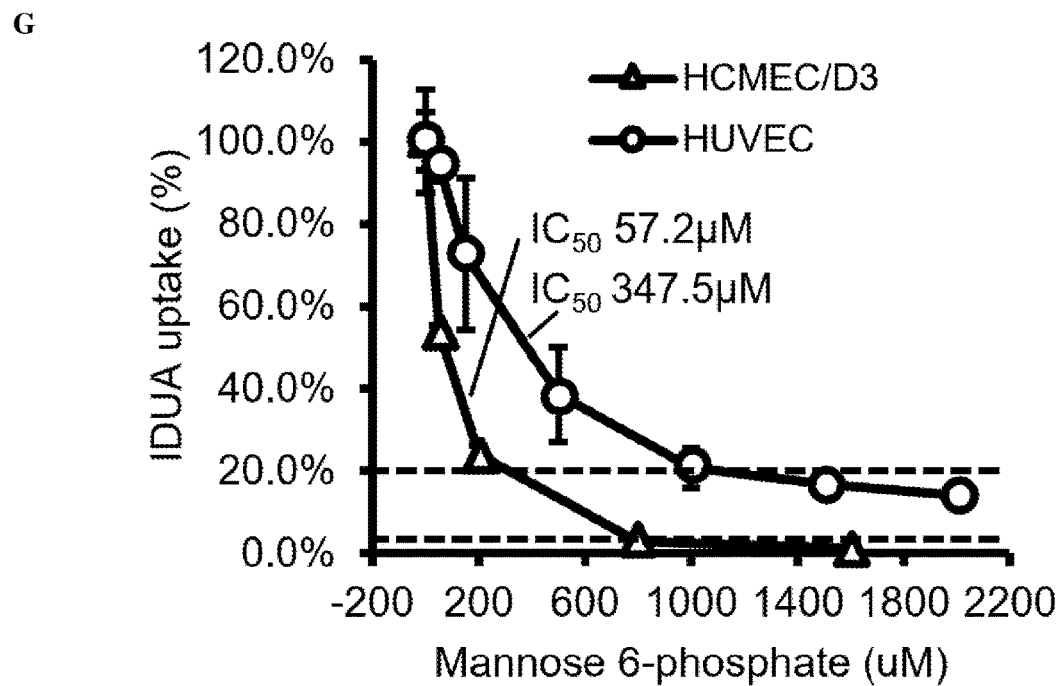
Figure 3:
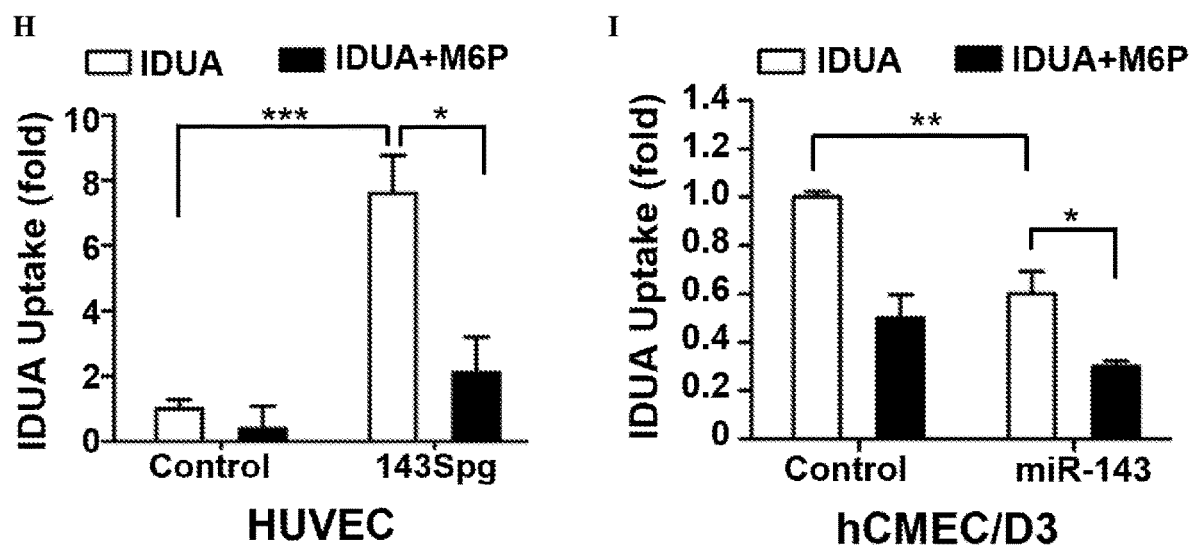

Taken together, these data defined the changes of miRNAs expression in developing BBB and indicated miR-143 as a potential M6PR regulator that may contribute to its function loss on mature BBB in a posttranscriptional manner.

miR-143 Directly Regulates M6PR by Interacting with Its 3'UTR. Mature miR-143 and miR-145a sequences are identical between mouse (mmu-miR-143-3p and mmu-miR-145a) and human (hsa-mir-143 and hsa-mir-145), respectively. However, they show no homology with each other in mature sequence, which suggests they may regulate distinct targets. In TargetScan mouse 7.1, miR-143 binds to three potential sites in the 3'UTR of M6PR, one conserved (binding site 3, B3) and two poorly conserved sites (B1 and B2) (FIGS. 2A and 2B), but there is no miR-145a putative binding site on M6PR transcript. To confirm the interaction between miR-143 and M6PR 3'UTR, we fused full length of M6PR 3'UTR (WT), as well as single (Mut1, Mut2, Mut3) or triple mutated UTRs (Mut123) in each binding site to downstream of Firefly luciferase (Fluc) coding sequence (FIG. 2A). Upon co-transfection with miRNA expression plasmid, miR-143, but not miR-145a, specifically suppressed Fluc expression (FIG. 2C) that was further confirmed by a dose dependent inhibition when increase UTR to miR-143 ratio from 1:1 to 1:4 (FIG. 2D). Specificity of the miR-143 effect on M6PR-UTR was further demonstrated by mutation of seed sequence in the miR-143 targeted regions, which led to an apparent complete abrogation of inhibitory effect of miR-143 on Fluc expression in site 2 and 3 (Mut2, Mut3 and Mut123); Mut1 still showed significant but attenuated reduction (FIG. 2E). Thus, M6PR 3'UTR can specifically interact with miR-143 (e.g., via binding sites of 2 and 3).

miR-143 Negatively Controls M6PR Functions in Vascular Endothelial Cells. To further understand the functional correlation between miR-143 and M6PR, two human vascular endothelial cell lines HUVEC and hCMEC/D3 were used. HUVEC showed 6-fold higher miR-143 and lower M6PR mRNA and protein expression than those in hCMEC/D3 (FIGS. 3A and 3B). HIV-based lentiviral sponge vector (LV-143Spg) that traps endogenous miR-143 resulting in its degradation, as well as a miR-143 overexpression construct driven by CMV promoter were generated for manipulation of endogenous miR-143 (FIG. 3C; FIG. 3D). Depletion of miR-143 by LV-143Spg in HUVEC (143Spg) resulted in 80% decrease of miR-143 expression (FIG. 3E, left panel) and ~1.5-fold increase of M6PR mRNA (FIG. 3E, middle panel) and protein (FIG. 3E, right panel) compared to those control cells transduced with empty lentivirus as determined by RT-qPCR and western blot, respectively. On the contrary, elevating miR-143 expression in hCMEC/D3 lowered M6PR mRNA and attenuated over 60% protein expression (FIG. 3F), thereby confirming the negative effect of miR-143 on M6PR expression in both human endothelial cells.

Figure 4:
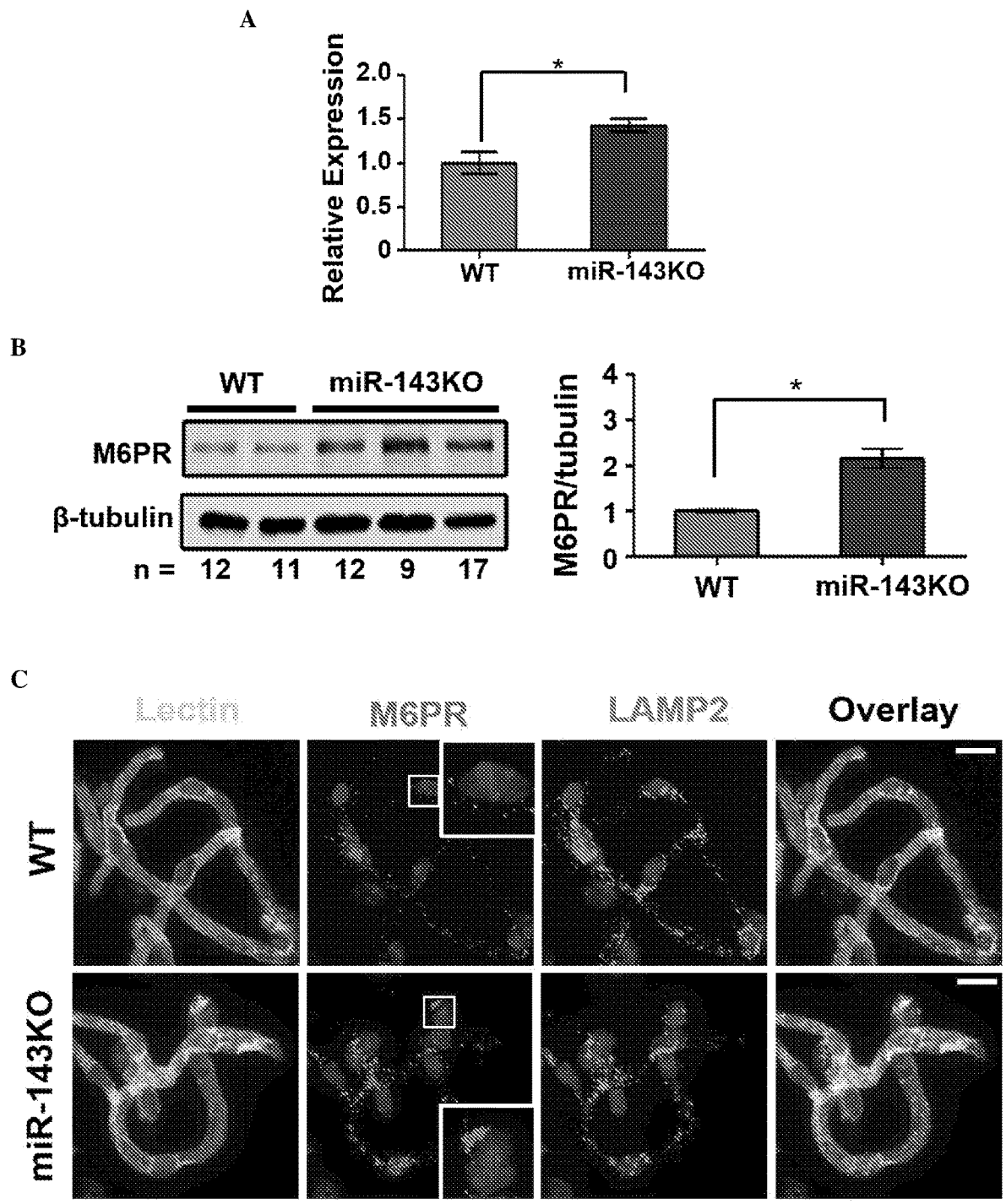
FIG. 4: Loss of miR-143 increases M6PR expression and M6PR-mediate uptaking in brain vasculatures from miR143 KO mice. (A) Upregulation of M6PR mRNA was evident in miR-143-null mice as determined by real time qPCR. Small RNA fragments (<200 nt) extracted from two BrMV isolations (n=12 mice, ~3-month old) in each group were subjected to reverse transcription and qPCR (triplicate reactions) in two independent experiments. (B) Western blot analysis of M6PR expression in BrMV from WT and miR-143 knock out mice. The number of mice contributing to each sample is indicated as n. Semi-quantification of gray densities in western blot by ImageJ is shown in the right panel. (C) Representative images of immunofluorescence staining of BrMV isolates. Cytospin of BrMV samples were stained with anti-M6PR (red) as well as anti-LAMP2 (purple) for lysosomes, fluorescein-labeled lectin (green) for brain endothelial cells and DAPI for nuclei (blue). Areas within white squares were enlarged and shown as insets. (D) Semi-quantification of mean fluorescence intensity showed significant increase of M6PR signals, but not LAMP2, in BrMV from miR-143KO mice compared to WT. Over 100 brain endothelial cells were quantified per genotype. (E) Antibody internalization in BrMV. Left panel, freshly isolated BrMV were incubated with anti-M6PR and anti-LAMP2 in serum/cytokine free EGM-2 media at 37° C. for 1 h, and followed by cyto-spinning, fixation and staining with 2° antibodies for M6PR and LAMP2, as well as lectin and DAPI. The data show the increase of M6PR on the surface of BrMV while LAMP2 serves as a intracellular control. Right panel, BrMV were subjected to the same procedures as left panel except that only anti-M6PR was added for binding-internalization and LAMP2 was stained afterwards to validate LAMP2 staining. Arrowheads indicate internalized M6PR antibody. Scale bars in C and D, 20 μm. Data in bar graphs are expressed as mean±SD for A, and mean±SEM for B and D; *$p<0.05$ by two-tailed t test.
Figure 4:
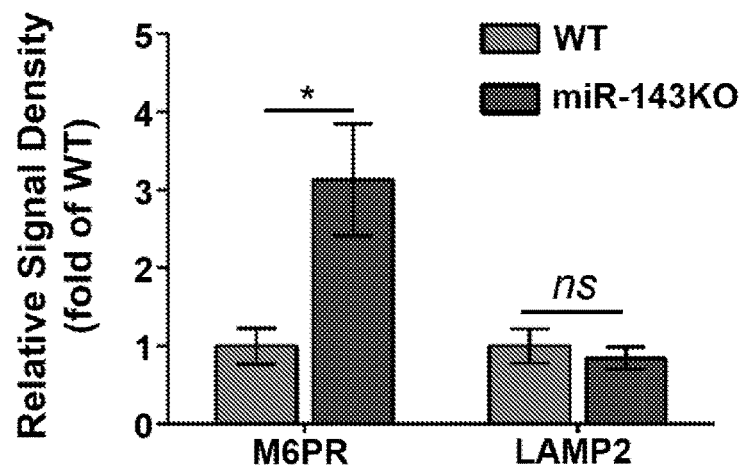
Figure 4:
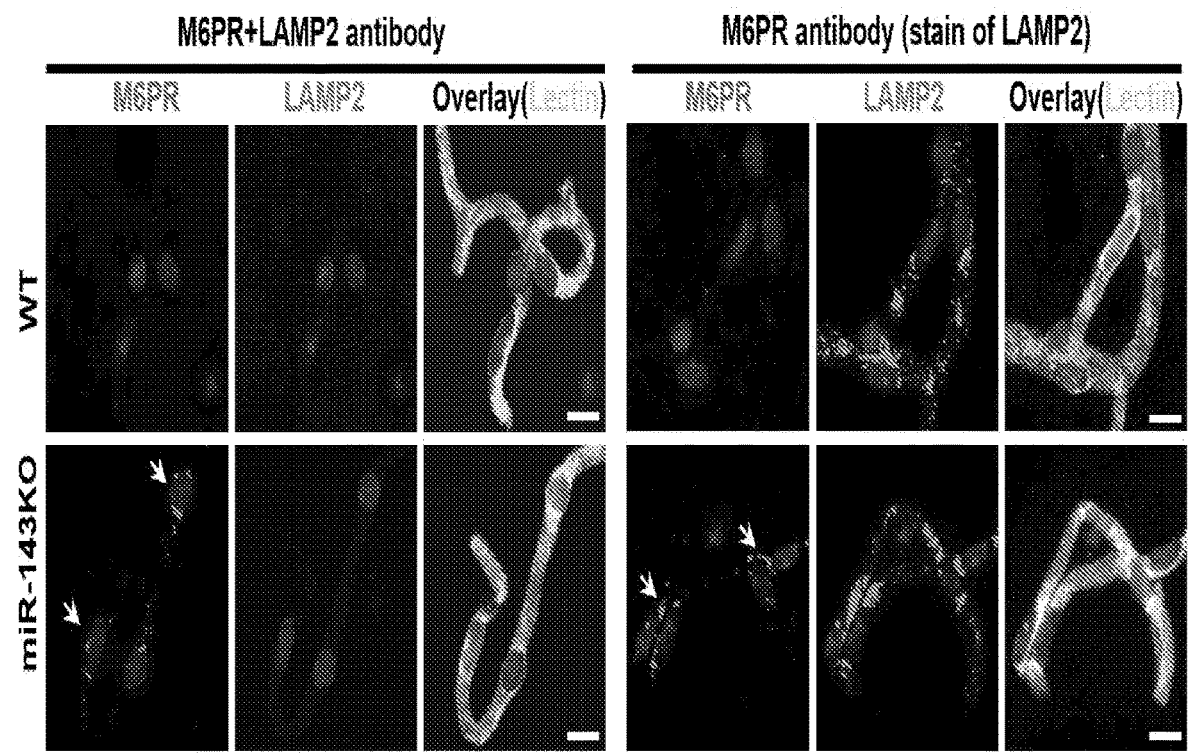

IDUA enzymes generated from HEK293-IDUA cells that stably overexpressing human IDUA cDNA with normal M6P "tag" were accessible in M6PR mediated lysosomal trafficking pathway in human vascular cells by competitive uptake assay (FIG. 3G). hCMEC/D3 is derived from human brain vascular endothelial cells, and HUVEC is human umbilical vascular endothelial cells. The data suggest greater sensitivity of hCMEC/D3 cells to M6P inhibitor than HUVEC ($IC_{50}$ 57.2 µM vs 347.5 µM, FIG. 3G). The levels of M6PR-independent uptake in HUVEC cells (plateau at ~18%) could be derived from pinocytotic events that are more frequent in HUVEC, a non-BBB originated endothelial cell line. To minimize the effect of pinocytosis, binding and internalization assay was applied to evaluate M6PR receptor-specific uptake pathway in those miR-143 manipulated cell lines. After incubation in IDUA conditioned media with the equal amounts of enzymatic activities at 4° C., the net IDUA that was taken up by the miR-143 sponge transduced cells (143Spg) increased approximately 7-fold compared to mock transduced HUVEC cells (control). Meanwhile, it could be specifically blocked upon M6P inhibition (1.5 mM) (FIG. 3H). Contrary to miR-143 knock down, elevating miR-143 expression in hCMEC/D3 cells repressed the IDUA intake as shown by a ~40% reduced intracellular enzyme activity compared to that in control cells (FIG. 3I). These functional analyses highlighted that miR-143 negatively regulates the M6PR-mediated uptake pathway in human vascular endothelial cells in vitro.

miR-143 Represses M6PR Function in Brain Microvasculature. To determine if miR-143 is involved in regulation of M6PR on BBB in vivo, we examined the M6PR function in adult BrMV from a miR-143 knockout (miR-143KO) mouse model. A 42% increase of M6PR transcripts as well as an averaged 2-fold higher M6PR protein in adult miR-143KO BrMV (3 months) over WT brains (FIGS. 4A and 4B) were showed by quantitative PCR and western blot, respectively. Immunostaining also showed more abundant granulated M6PR signals in miR-143KO brain endothelium, which is labeled with lectin to give complete staining of brain capillaries (FIG. 4C) in BrMV isolates. Semi-quantitative analysis showed greater than 3-fold increase in M6PR fluorescent density in miR-143KO mice compared to WT control (FIGS. 4C and 4D). Whereas lysosomal-associated membrane protein 2 (LAMP2), a glycoprotein housing lysosomal membrane, showed comparable level in both capillary isolates (FIGS. 4C and 4D).

Although a majority of M6P receptors are expressed in cytoplasmic vesicles (e.g. lysosomes and trans-Golgi network (TGN)), 10~15% receptors are present at the cell surface that mediate endocytosis or recapturing a variety of M6P-containing lysosome enzymes. Changes to the accessibility to these receptors on the cell surface were examined by ex vivo antibody (ab) uptake assay. An M6P ab that recognizes the ectodomain of transmembrane M6P receptor, together with an antibody that can only adherent to the luminal domain of LAMP2 were applied. In miR-143KO BrMV, M6PR ab was obviously engulfed and a sizeable proportion of them aggregated around nuclei (white arrows, FIG. 4E, left and bottom panel) which were further visualized to colocalize with lysosomes by LAMP2 staining afterwards (FIG. 4E, right panel). However, barely detectable M6PR ab was endocytosed in adult age-matched BrMV from wild type mice (FIG. 4E, left and top panel). LAMP2 ab could not be taken in by both BrMV isolates, because it was unable to interact with LAMP2 intracellular domain in the alive endothelium (FIG. 4E, left panel in the middle), and thus served as a negative control.

Figure 5:
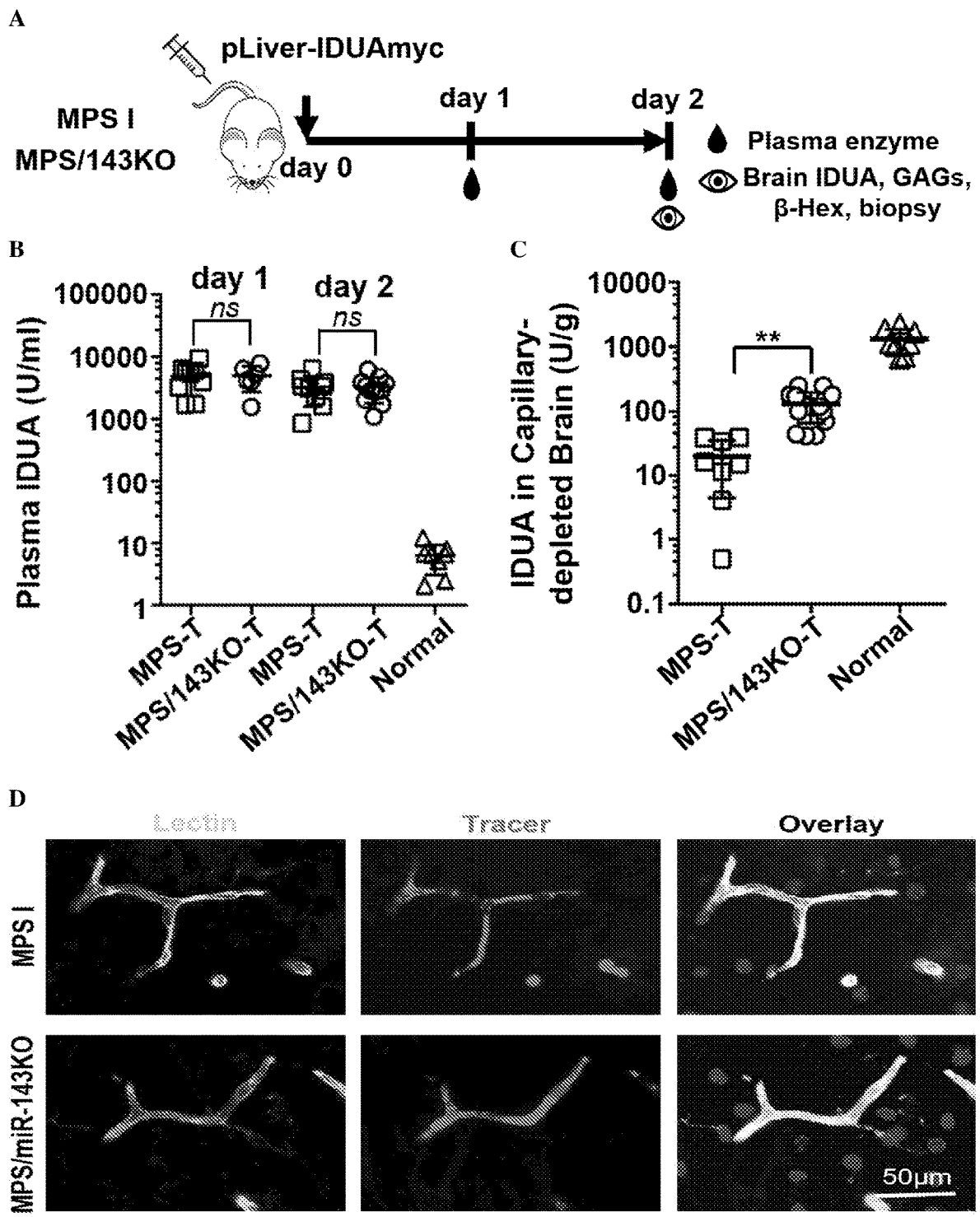
FIG. 5: Deprivation of miR-143 facilitates brain delivery of peripheral IDUA in MPS I mice with improved therapeutic potential. (A) Schematic diagram of experimental design. Adult mice (~7 wks old) were injected with a plasmid expressing IDUAmyc from a liver-specific promoter by liver-targeted hydrodynamic injection. Two days after injection, whole brains were collected from well perfused animals for dissection and detection of IDUA, GAGs and β-hexosaminidase. (B) Enzyme activities in plasma at indicated time points. n=6~8 mice in treated MPS I (MPS-T) and MPS I/143KO groups (MPS/143KO-T). Heterozygous littermates were used as normal controls (Normal). (C) IDUA activity in capillary-depleted brain parenchyma. (D) Evaluation of BBB integrity in MPS I and MPS/143KO mice. Tracer, tetramethylrhodamine (red) conjugated 10-kDa Dextran (4 mg/ml, 90 ul/mouse), was injected into the left ventricle of heart with a Hamilton syringe. After 5 min of circulation, brains were dissected. Frozen sections of 10 μm were collected and stained with lectin to visualize cerebral microvessels. Representative images showed that all tracer was confined in capillaries, suggesting an intact BBB in both MPS and MPS/143KO mice. (E, F) Glycosaminoglycan (GAG) levels and β-hexosaminidase activities in the brain. All data are expressed as mean±SD. *$p<0.05$, **$p<0.01$, ∞, $p<0.0001$ by two-tailed t test; ns, not significant.
Figure 5:
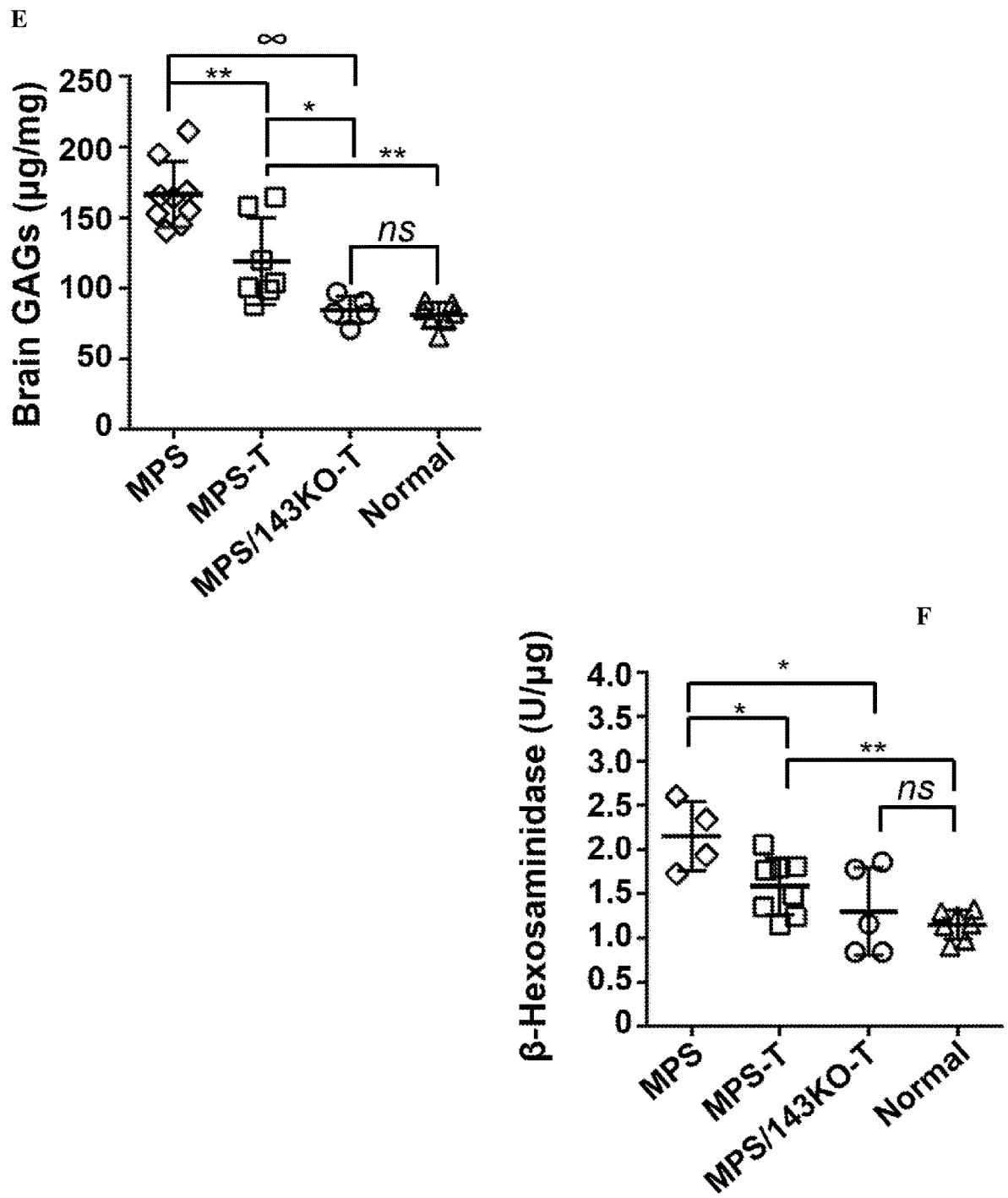

Together with our demonstration of differential M6PR presence in young and adult BBB-containing BrMV, these data suggest that knocking out miR-143 in adult mice reversed the M6PR expression pattern which is analogous to what we have previously observed in neonatal brains. Therefore, we speculated that repressing miR-143 levels on BBB may enhance CNS delivery of therapeutic enzymes to diseased brain via M6PR pathway.

miR-143 Ablation Leads to Increased IDUA Brain Delivery in MPS I Mice. To address this hypothesis, a two-day period of gene delivery by hydrodynamic tail-vein injection was performed. We generated miR-143 knockout mice in an MPS I background (MSP/143KO). Plasmid pLiver-IDUAmyc expressing IDUA-3'myc (IDUAmyc), which was driven by a liver-specific hybrid promoter to eliminate any possible enzyme generation in the CNS, were administered via hydrodynamic injection in the tail vein of adult MSP/143KO and MPS I mice (6~7-wk old) (FIG. 5A). In the observation period of day 1 and day 2, robust and relatively continuous IDUA with comparative activities were observed in the circulation of both genotypes (FIG. 5B). However, capillary-depleted brain tissues from well perfused MPS/143KO mice (MPS/143KO-T) exhibited ~6-fold (mean of 131 U/g vs 22 U/g) higher IDUA activity than MPS I treatment control (MPS-T) after two days' treatment (FIG. 5C), confirming that miR-143 null brain is more 'permeable' to IDUA. Nevertheless, a leaky BBB might lead to non-specific diffuse of IDUA (~70 kDa) from blood to brain in MPS/143KO mice. Interestingly, previous reports indicate that silencing miR-143 may protect the BBB (i.e., instead of disrupting) from drug abuse mediated vascular dysfunction. BBB integrity of the experimental animals then was assayed by injection of dextran-tracer (10 kDa), which is much smaller than IDUA in molecular weight, into circulation from left ventricle of heart. For tracer distribution in the brain, dextran was confined within vasculatures but not in adjacent parenchyma cells both in MPS I and MPS/143KO (FIG. 5D), indicating an intact and functional BBB for both experimental animals.

Deficiency of IDUA leads to abnormal accumulation of glycosaminoglycan (GAG) in the brain. Abnormally high GAG accumulation in untreated MPS I mice was normalized in MPS/143KO-T mice (p=0.68 compared to normal mice) (FIG. 5E), which correlated with the higher brain IDUA activity. Despite a slight decline, treated MPS I mice (MPS-T) demonstrated higher GAG storage than normal (FIG. 5E). The reduction of β-hexosaminidase (β-hex) in the brain was also assessed. Although there was variation among different animals, MPS/143KO-T mice demonstrated statistically normalized β-hex activity compared to those detected in heterozygous littermates (p=0.47, FIG. 5F). In contrast, group MPS-T showed partially reduced but still higher β-hex activity than that in normal controls (FIG. 5F).

These findings suggested that sufficient metabolic correction was achieved even in a short-term of peripheral enzyme delivery in brain of MPS/143KO mice, which is positively correlated with the higher M6P receptor presence on miR-143 knockout blood-brain barrier.

Figure 6:
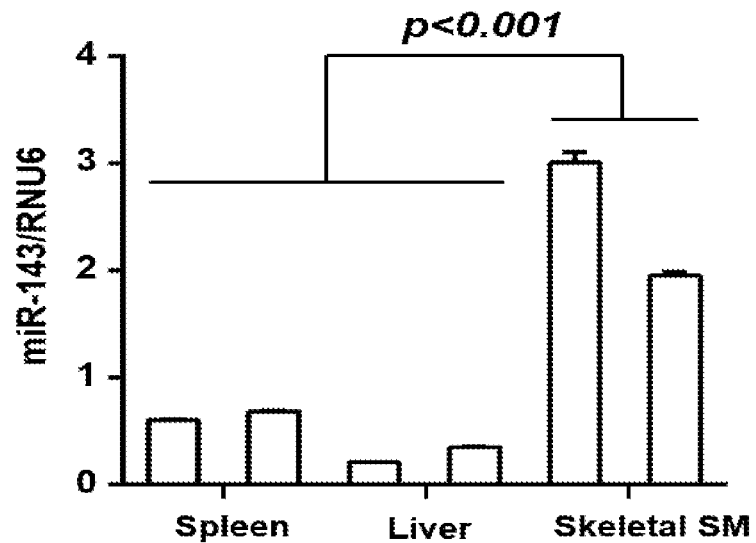
FIG. 6: MiR-143/M6PR endogenous expression in peripheral organs or tissues; IDUA distribution in brain micro-vasculatures, neurons and microglial/brain macrophages. (A) miR-143 endogenous levels in spleen, liver and skeletal smooth muscle (skeletal SM) from adult wild type mice (n=2) as determined by real time quantitative PCR. Data are shown as relative expression n compared to RNU6 as internal reference. (B) Western blot analysis of M6PR expression in spleen, liver and skeletal SM. Semi-quantification of gray densities in western blot by ImageJ is shown in the lower panel. *$p<0.05$ by two-tailed t test. These data are consistent with the down-regulation of M6PR by miR143. (C) Representative images from immunofluorescence analysis of cerebral sections. Brains from treated mice with similar plasma IDUA activities (~3,000 U/ml, day 2 after HTV injection) were stained with antibody against myc-tag for IDUA (red), lectin for brain endothelial cells (green), and counterstained with DAPI for nuclei (blue). Areas within white squares are enlarged and shown on the right. Arrowheads indicate IDUA, demonstrating delivery of IDUA into none-capillary parenchymal cells of MPS/143KO, but not MPS I brain. (D, F) Representative images from immunofluorescence analysis of cerebral sections. Brains from treated mice with similar plasma IDUA activities (~3,000 U/ml, day 2) were stained with antibodies against myc-tag for IDUA (green), NeuN for neurons (red) in brain stem (in D) or CD68 for activated micrglia/brain macrophages (red) in cerebral cortex (in F), and counterstained with DAPI for nuclei (blue). Areas within white squares are enlarged and shown on the right. Arrowheads indicate IDUA positive neurons or macrophages. (E, G) Quantification of IDUA$^+$ neurons and microglia/brain macrophages in cerebrum of MPS I and MPS/143KO mice 2 days after treatment. Data were derived from brain sections of two pairs (MPS I and MPS/143KO) of IDUA (plasma)-matching mice, each with 9 sections and >500 NeuN$^+$ (in E) or CD68$^+$ (in G) cells counted separately for each of the brain regions, including brain stem, cortex and middle brain. All data are presented as mean±SEM. *$p<0.05$, $p<0.01$, *$p<0.001$ by two-tailed t test.
Figure 6:
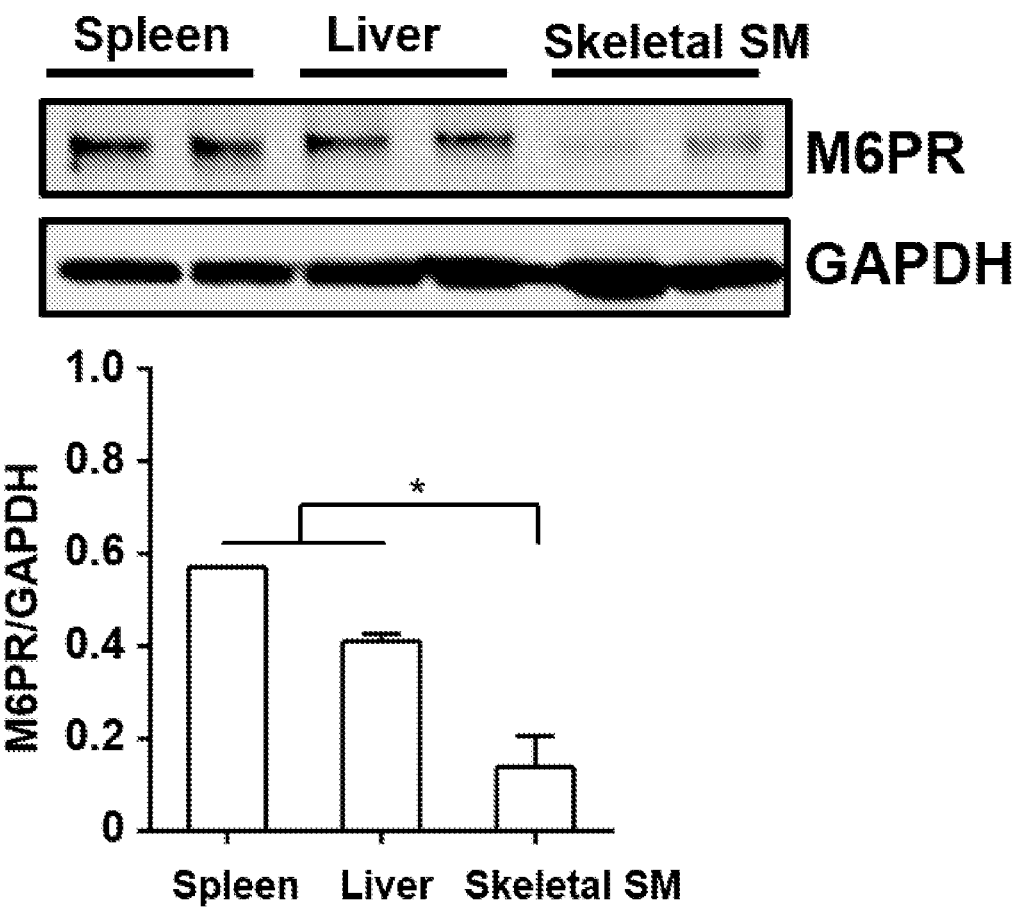
Figure 6:
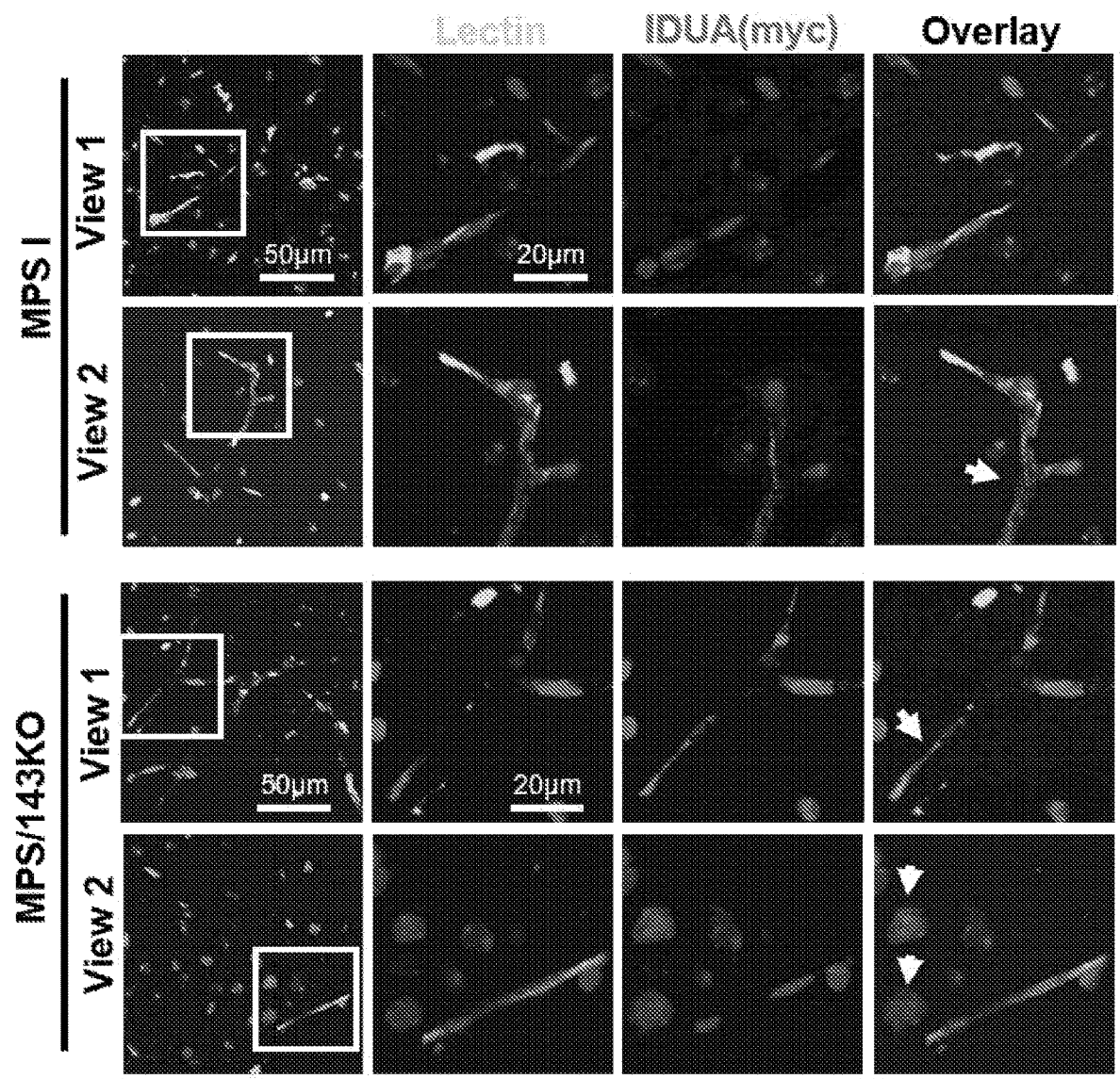
Figure 6:
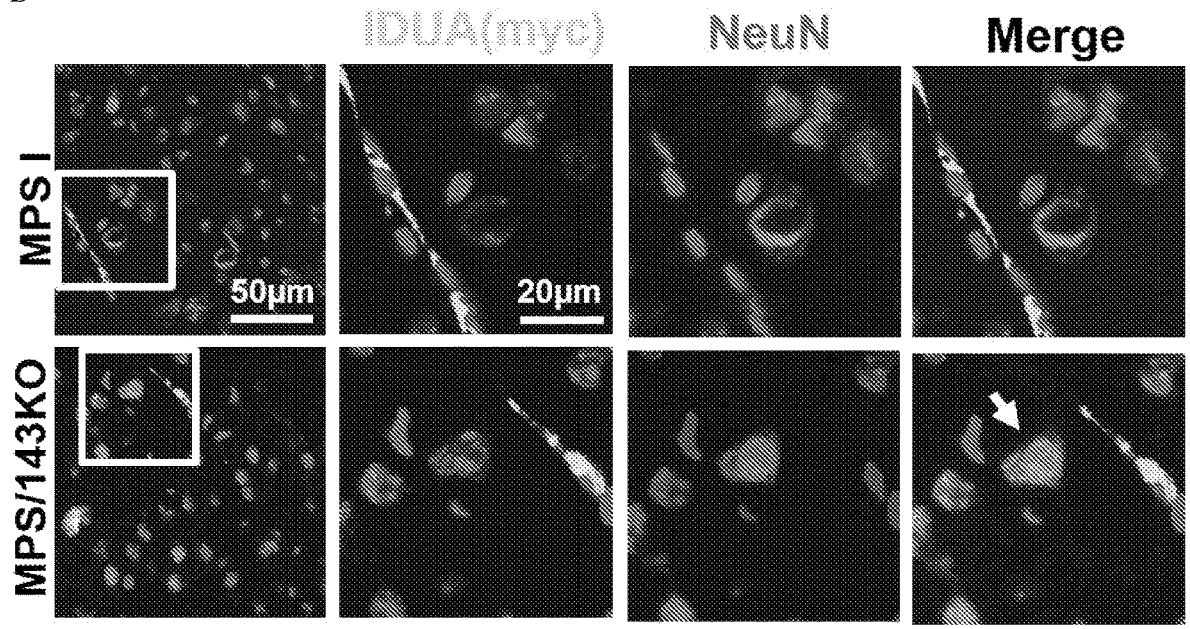
Figure 6:
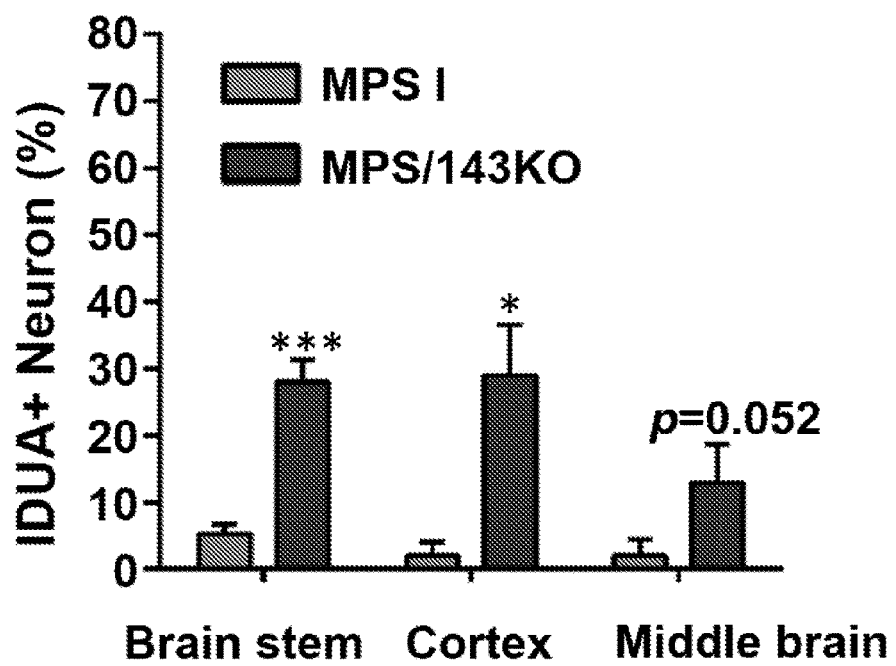
Figure 6:
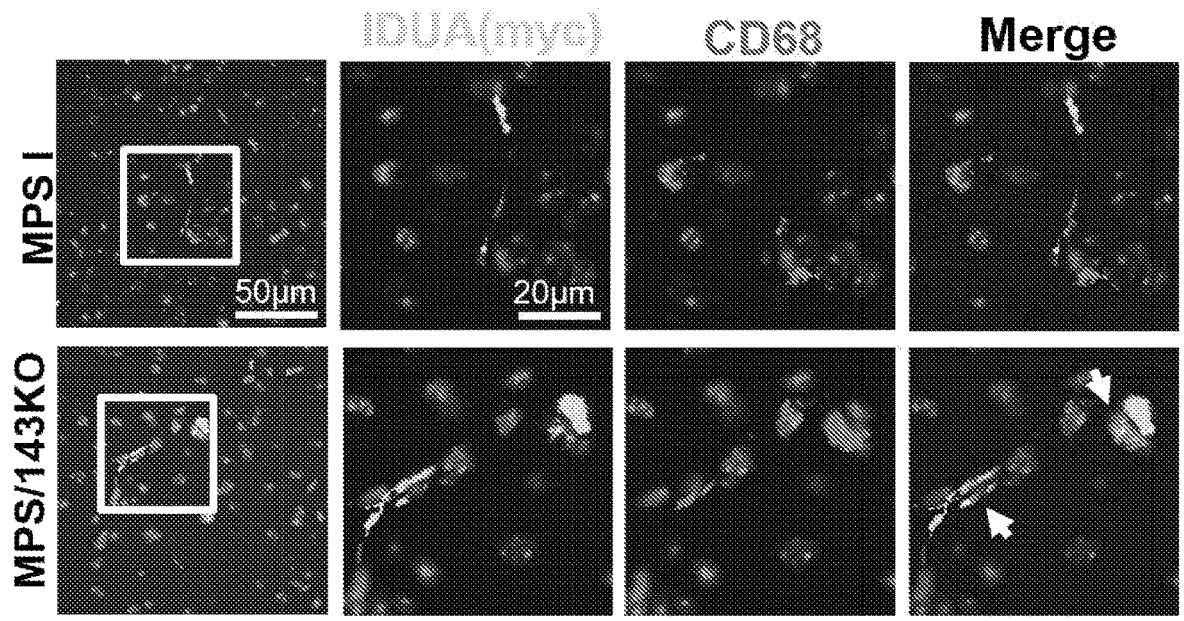
Figure 6:
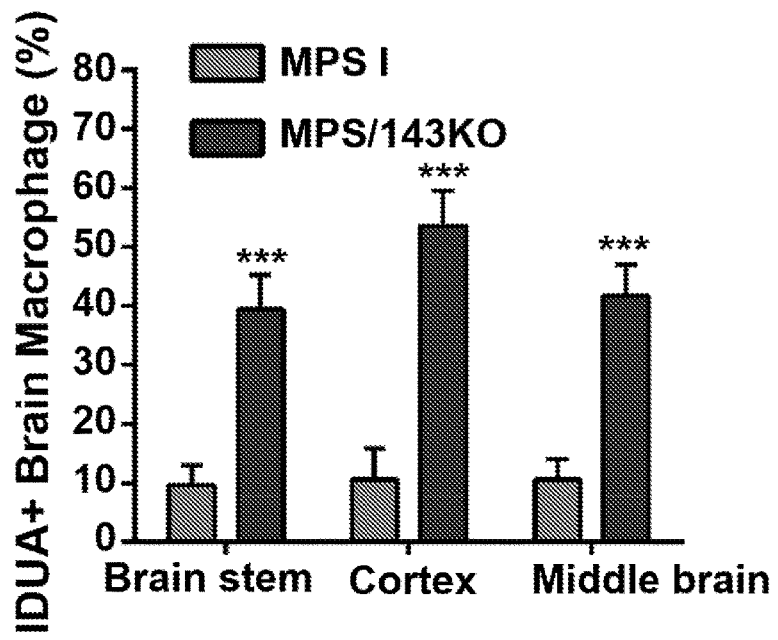

Loss of miR-143 Facilitates IDUA Delivery across BBB to Multiple Brain Cell types. To dissect the distribution of enzyme in hydrodynamic injected brain, immunofluorescence analysis was performed among different types of brain cells. The transportation of IDUAmyc was visualized by myc-positive staining in the BBB-forming capillary endothelial cells labeled by lectin (FIGS. 6A and 6B). Brain microvasculatures in MPS I brain showed barely detectable IDUA (FIG. 6C, view 1) or very limited number of them displayed IDUA presence that more likely existed in the luminal side of vascular endothelium layer, but not in the cell body (FIG. 6C, view 2). However, we observed more enzymes in MPS/143KO brain that colocalized with brain endothelial cells. Brain parenchyma cells adjacent to the IDUA containing endothelium also showed IDUA positive staining (FIG. 6C, view 1 and 2). To distinguish the cell types involved, we stained brain sections with myc (IDUA) as well as NeuN, a nuclear marker associated with the vast majority of mature neurons or CD68, a marker for macrophage. As shown in FIG. 6D, IDUA positive cells were located both in capillary-like endothelium and perivascular parenchymal cells in miR-143 null MPS I brain, while IDUA positive cells were restricted in BBB derived endothelial cells in MPS I. Furthermore, semi-quantification by ImageJ showed higher percentages of IDUA positive cells that colocalized with neurons in the brain stem, cerebral cortex and middle brain of MPS/143KO compared to those in MPS I (FIG. 6E).

Resident macrophage cells can act as the first and main form of active immune defense in the CNS. In FIG. 6F, more juxta-vascular CD68+ cells carrying IDUA has been indicated in the brain of MPS/143KO than in MPS I. Statistically, approximately 10% of brain macrophages showed IDUA co-staining in treated MPS I brain (FIG. 6G). However, it increased to 39%, 54% and 42% in brain stem, cortex and middle brain, respectively, from MPS/143KO compared to those in MPS I controls (FIG. 6G).

Collectively, these findings further support the concept that M6PR is specifically tempered by miR-143 on BBB to facilitate CNS penetration of proteins (e.g., therapeutic enzymes for disease treatment).

DISCUSSION

In this study, we found that modulation of M6PR expression on BBB could occur through the action of miRNAs and could be one of the mechanisms to hinder CNS delivery of lysosomal enzymes. The neonatal BrMV possesses higher M6PR expression both in transcripts and receptor proteins compared to those in the adult brain. miRNA profiling defined a set of miRNAs involved in promoting the maturation of blood-brain barrier among the early perinatal period. Concurrent genomic organization revealed that miR-143/145 are co-transcribed and expressed from the same gene, which was further confirmed by our microRNA array and qRT-PCR data (FIGS. 1C and 1E). Combined with bioinformatics tools, miR-143, but not miR-145a, was identified as a potential M6PR targeted regulator. Our gene ontology (GO) annotation of predicted miR-145a targeting genes indicated that it might be involved in nervous system development, cell differentiation, and negatively regulate cell migration, etc. (data not shown).

Our luciferase reporter assay confirmed the direct interaction between mature miR-143 and murine M6PR 3'UTR (NM_010515.2) in vitro. Sequence blast analysis (TargeScan program) showed that 3'UTR of human M6PR mRNA (NM_NM_000876.3) contains two potential binding sites for miR-143, which were conserved among vertebrates. This indicates miR-143 may modulate M6PR in humans as well. Moreover, in human endothelial cells, we emphasized the reverse relationship of miR-143 levels with M6PR functions by using miR-143 decoy or overexpression cassette. Upon introduction of an miR-143 sponge or an miR-143 gene, the expression of M6PR protein in whole cell lysate was increased 1.5-fold in HUVEC cells or decreased more than 2-fold in hCMEC/D3 cells, respectively (FIGS. 3E and 3F). Such changes in M6PR protein levels were functionally associated with increased or declined uptake of IDUA enzyme via MPR-mediated pathway as determined by inhibitory uptake assay Immunofluorescence staining in miR-143-null BrMV indicated an almost 3-fold increase of M6PR expression compare to WT BrMV. Although only a relative low percent (about 10~15%) of M6PR are anchored on the cell surface, about 1.5~3-fold increases in total protein per endothelial cell will likely result in approximate 15~45% of receptor in total. Distribution on the cell surface and desired luminal presence on the BBB is not apparently affected by miR-143. In the adult brain, genetic removal of miR-143 increased M6PR expression, as well as at least some of its biological function (e.g., receptor-mediated endocytosis of a non-natural ligand, M6PR antibody, via ex vivo uptake assay).

In a miR-143 KO murine MPS I model, appropriate circulatory IDUA, released by hydrodynamic injected liver, can be more efficiently trafficked into brain vascular endothelium as well as nonendothelial perivascular cells, such as neurons and brain macrophages compared to MPS I. The diseased brain of MPS I/miR-143KO was treated by apparent complete correction of accumulated GAG and elevated β-hexosaminidase. Our findings not only provide direct evidence of the phenomenon of progressive loss of M6PR during BBB maturation in mice, but also demonstrate that expression of M6PR can be restored by manipulating miR-143 in the adult BBB, a novel concept for drug delivery across the BBB. Of note, the mRNA of CI-MPR is too large in size (over 14 kb in human and near 9 kb in mouse) to currently be manipulated by direct expression via any in vivo gene transfer. Therefore, in consideration of miR-143's role in shaping a highly restricted M6PR transport capacity in mature BBB, rescue M6PR by specific inhibiting miR-143 on BBB may be applied as a comprehensive therapeutic strategy (e.g., to rectify the CNS lesions resulting from the implementation of enzyme replacement therapy (ERT) in those diseases such as Fabry disease, Pompe disease, Sandhoff's disease, MPS VII and MPS I patients).

Also, we observed that loss of miR-143 alone does not appear to affect the lifespan or reproductivity in mice (unpublished). Additionally, ablation of miR-143 in the MPS I diseased brain did not seem to demolish blood-brain barrier (FIG. 5D).

In conclusion, our study highlights the molecular mechanism that miR-143 modulates M6PR in developing BBB endothelium, and provides a novel opportunity to treat diseases (e.g., neurological lysosomal storage diseases).

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner Indeed, various modifications of the invention in addition to those described herein will become apparent to those skilled in the art from the foregoing description and the accompanying figures. Such modifications are intended to fall within the scope of the appended claims.

What is claimed is:

1. A nucleic acid molecule, wherein
   (A) the nucleic acid molecule comprises SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:39, or SEQ ID NO:40; or
   (B) the nucleic acid molecule comprises an RNA molecule, where the RNA molecule consists of more than one RNA core molecule and one or more RNA core linkers,
   wherein
      the more than one RNA core molecules are linked together by one or more RNA core linkers which RNA core linkers each comprise one or more ribonucleotides;
   wherein
      the more than one RNA core molecules are selected from the group consisting of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:37, and SEQ ID NO:38,
      at least one of the one or more RNA core linkers consists of from 1 to 10 ribonucleotides,
      there is only one RNA core linker linking any two adjacent RNA core molecules,
      each RNA core linker can be the same or different, and
      the nucleic acid molecules of (B) consist of from 110 to 255 ribonucleotides.

2. The nucleic acid molecule of claim 1, wherein all of the more than one RNA core molecules have a percent identity compared to SEQ ID NO:1, of at least about 35%.

3. The nucleic acid molecule of claim 1, wherein at least one of the one or more RNA core linkers consists of from 1 to 7 ribonucleotides.

4. The nucleic acid molecule of claim 1, wherein all of the one or more RNA core linkers consist of from 1 to 7 ribonucleotides.

5. The nucleic acid molecule of claim 1, wherein at least one of the one or more RNA core linkers is selected from A, C, G, U, AA, CC, GG, UU, AC, AG, AU, CA, CG, CU, GA, GC, GU, UA, UC, UG, ACG, ACU, AGU, GCG, GCU, GGU, UCG, UCU, UGU, CGAU, CUAGA, or UCUAGA.

6. The nucleic acid molecule of claim 1, wherein the nucleic acid molecule comprises SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:39, or SEQ ID NO:40.

7. A nucleic acid molecule comprising a DNA molecule which encodes the RNA molecule of claim 1.

8. The nucleic acid molecule of claim 7, wherein the nucleic acid molecule is part of a vector, a viral vector, a retroviral vector, a lentiviral vector, an adenoviral vector, an adeno-associated viral vector, an AAV2, an scAAV, an AAV-Br1, a herpesviral vector, a chimeric viral vector, a plasmid, an expression vector, a conjugative vector, a non-conjugative vector, or a nanoparticle.

9. The nucleic acid molecule of claim 7, wherein the nucleic acid molecule further comprises a promoter, a CMV promoter, a miniCMV promoter, an h1CMV promoter, an h2CMV promoter, an SV2 promoter, a U6 promoter, an H1 promoter, an SF promoter, an SFFV promoter, an EF promoter, an endothelial promoter, a Tie2 promoter, a promotor for expression of shRNA, a promotor for expression of siRNA, or an RNA polymerase III promoter.

10. The nucleic acid molecule of claim 7, wherein the nucleic acid molecule further comprises a promoter and the promoter is directed to or specific to a tissue, vascular endothelia, hepatocytes, smooth muscles, cardiomyocytes, hematopoietic stem/progenitors or their offspring, myeloid/erythroid progenitors or their offspring, an organ, brain, liver, kidney, spleen, heart, or lung.

11. The nucleic acid molecule of claim 7, wherein the nucleic acid molecule further comprises DNA that encodes for a protein, a lysosomal protein, α-L-iduronidase (IDUA), iduronate-2-sulfatase, heparan N-sulfatase, N-acetyl-alpha-D-glucosaminidase, acid alpha-glucosidase, arylsulfatase A, or a protein that can be transported via M6PR.

12. A composition comprising the nucleic acid molecule of claim 1.

13. The composition of claim 12, wherein the amount of the nucleic acid molecule is from about 0.0001% (by weight total composition) to about 99%.

14. A pharmaceutical composition comprising the nucleic acid molecule of claim 1.

15. The pharmaceutical composition of claim 14, wherein the amount of the nucleic acid molecule is from about 0.0001% (by weight total composition) to about 50%.

16. The nucleic acid molecule of claim 1, wherein at least one of the more than one RNA core molecules is SEQ ID NO:2, SEQ ID NO:5, or SEQ ID NO:6.

17. The nucleic acid molecule of claim 1, wherein the RNA molecule consists of from 110 to 255 ribonucleotides.

18. The nucleic acid molecule of claim 1, wherein at least one of the more than one RNA core molecules is SEQ ID NO:2 or SEQ ID NO:6.

19. The nucleic acid molecule of claim 1, wherein the nucleic acid molecule comprises an RNA molecule, where the RNA molecule consists of more than one RNA core molecule and one or more RNA core linkers, wherein the more than one RNA core molecules are linked together by one or more RNA core linkers which RNA core linkers each comprise one or more ribonucleotides;

wherein the more than one RNA core molecules are selected from the group consisting of SEQ ID NO:2, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:37, and SEQ ID NO:38, at least one of the one or more RNA core linkers consists of from 1 to 10 ribonucleotides, there is only one RNA core linker linking any two adjacent RNA core molecules, each RNA core linker can be the same or different, and the nucleic acid molecules of (B) consist of from 110 to 255 ribonucleotides.

* * * * *

SEQUENCE LISTING

<160> NUMBER OF SEQ ID NOS: 44

<210> SEQ ID NO 1
<211> LENGTH: 21
<212> TYPE: RNA
<213> ORGANISM: Artificial Sequence
<220> FEATURE:
<223> OTHER INFORMATION: RNA core original

<400> SEQUENCE: 1
gagcuacagu gcuucaucuc a                                              21

<210> SEQ ID NO 2
<211> LENGTH: 20
<212> TYPE: RNA
<213> ORGANISM: Artificial Sequence
<220> FEATURE:
<223> OTHER INFORMATION: RNA core

<400> SEQUENCE: 2
gagcuacaga cgucaucuca                                                20

<210> SEQ ID NO 3
<211> LENGTH: 25
<212> TYPE: RNA
<213> ORGANISM: Artificial Sequence
<220> FEATURE:
<223> OTHER INFORMATION: RNA core

<400> SEQUENCE: 3
gagcuacagu ggauccuuca ucuca                                          25

<210> SEQ ID NO 4
<211> LENGTH: 25
<212> TYPE: RNA
<213> ORGANISM: Artificial Sequence
<220> FEATURE:
<223> OTHER INFORMATION: RNA core

<400> SEQUENCE: 4
gagcuacagu gcuucaucga ucuca                                          25

<210> SEQ ID NO 5
<211> LENGTH: 25
<212> TYPE: RNA
<213> ORGANISM: Artificial Sequence
<220> FEATURE:
<223> OTHER INFORMATION: RNA core

<400> SEQUENCE: 5
ggaucagcua cagugcuuca ucuca                                          25

<210> SEQ ID NO 6
<211> LENGTH: 25
<212> TYPE: RNA
<213> ORGANISM: Artificial Sequence
<220> FEATURE:
<223> OTHER INFORMATION: RNA core

<400> SEQUENCE: 6
gaucgagcua cagugcuuca ucuca                                          25

<210> SEQ ID NO 7
<211> LENGTH: 24
<212> TYPE: RNA
<213> ORGANISM: Artificial Sequence

```
<220> FEATURE:
<223> OTHER INFORMATION: RNA core

<400> SEQUENCE: 7
gagcuacaga cgucaucgau cuca                                              24

<210> SEQ ID NO 8
<211> LENGTH: 28
<212> TYPE: RNA
<213> ORGANISM: Artificial Sequence
<220> FEATURE:
<223> OTHER INFORMATION: RNA core

<400> SEQUENCE: 8
ggaucagcua cagacgucau cgaucuca                                          28

<210> SEQ ID NO 9
<211> LENGTH: 18
<212> TYPE: RNA
<213> ORGANISM: Artificial Sequence
<220> FEATURE:
<223> OTHER INFORMATION: RNA core - M6PR binding site 1

<400> SEQUENCE: 9
aagccacaug caucucac                                                     18

<210> SEQ ID NO 10
<211> LENGTH: 23
<212> TYPE: RNA
<213> ORGANISM: Artificial Sequence
<220> FEATURE:
<223> OTHER INFORMATION: RNA core - M6PR binding site 2

<400> SEQUENCE: 10
gcuccgugcc cuaccucauc ucu                                               23

<210> SEQ ID NO 11
<211> LENGTH: 21
<212> TYPE: RNA
<213> ORGANISM: Artificial Sequence
<220> FEATURE:
<223> OTHER INFORMATION: RNA core - M6PR binding site 3

<400> SEQUENCE: 11
ugagcuguag gucucaucuc u                                                 21

<210> SEQ ID NO 12
<211> LENGTH: 220
<212> TYPE: RNA
<213> ORGANISM: Artificial Sequence
<220> FEATURE:
<223> OTHER INFORMATION: RNA sequence

<400> SEQUENCE: 12
cuagagagcu acagacguca ucucacgaug agcuacagug gauccuucau cucaucuaga        60
gagcuacaga cgucaucuca cgaugagcua caguggaucc uucaucucau cuagagagcu       120
acagacguca ucucacgaug agcuacagug gauccuucau cucaucuaga gagcuacaga       180
cgucaucuca cgaugagcua caguggaucc uucaucucau                             220

<210> SEQ ID NO 13
<211> LENGTH: 165
<212> TYPE: RNA
<213> ORGANISM: Artificial Sequence
<220> FEATURE:
```

<223> OTHER INFORMATION: RNA sequence

<400> SEQUENCE: 13

| cuagagagcu acagacguca ucucacgaug agcuacagug gauccuucau cucaucuaga | 60 |
| gagcuacaga cgucaucuca cgaugagcua caguggaucc uucaucucau cuagagagcu | 120 |
| acagacguca ucucacgaug agcuacagug gauccuucau cucau | 165 |

<210> SEQ ID NO 14
<211> LENGTH: 255
<212> TYPE: RNA
<213> ORGANISM: Artificial Sequence
<220> FEATURE:
<223> OTHER INFORMATION: RNA sequence

<400> SEQUENCE: 14

| agugagcuac agugcuucau cucauggagc uacaguggau ccuucaucuc aagugagcua | 60 |
| cagugcuuca ucucauggag cuacagugga uccuucaucu caagugagcu acagugcuuc | 120 |
| aucucaugga gcuacagugg auccuucauc ucaagugagc uacagugcuu caucucaugg | 180 |
| agcuacagug gauccuucau cucaagugag cuacagugcu ucaucucaug gagcuacagu | 240 |
| ggauccuuca ucuca | 255 |

<210> SEQ ID NO 15
<211> LENGTH: 102
<212> TYPE: RNA
<213> ORGANISM: Artificial Sequence
<220> FEATURE:
<223> OTHER INFORMATION: RNA sequence

<400> SEQUENCE: 15

| agugagcuac agugcuucau cucauggagc uacaguggau ccuucaucuc aagugagcua | 60 |
| cagugcuuca ucucauggag cuacagugga uccuucaucu ca | 102 |

<210> SEQ ID NO 16
<211> LENGTH: 129
<212> TYPE: RNA
<213> ORGANISM: Artificial Sequence
<220> FEATURE:
<223> OTHER INFORMATION: RNA sequence

<400> SEQUENCE: 16

| uggagcuaca guggauccuu caucucaagu gagcuacagu gcuucaucuc auggagcuac | 60 |
| aguggauccu ucaucucaag ugagcuacag ugcuucaucu cauggagcua caguggaucc | 120 |
| uucaucuca | 129 |

<210> SEQ ID NO 17
<211> LENGTH: 228
<212> TYPE: RNA
<213> ORGANISM: Artificial Sequence
<220> FEATURE:
<223> OTHER INFORMATION: RNA sequence

<400> SEQUENCE: 17

| caugagcuac aguggauccu ucaucucacg augagcuaca guggauccuu caucucacau | 60 |
| gagcuacagu ggauccuuca ucucacgaug agcuacagug gauccuucau cucacaugag | 120 |
| cuacagugga uccuucaucu cacgaugagc uacaguggau ccuucaucuc acaugagcua | 180 |
| caguggaucc uucaucucac gaugagcuac aguggauccu ucaucuca | 228 |

```
<210> SEQ ID NO 18
<211> LENGTH: 224
<212> TYPE: RNA
<213> ORGANISM: Artificial Sequence
<220> FEATURE:
<223> OTHER INFORMATION: RNA sequence

<400> SEQUENCE: 18
caugagcuac aguggauccu ucaucucaca ugagcuacag uggauccuuc aucucacaug      60
agcuacagug gauccuucau cucacaugag cuacagugga uccuucaucu cacaugagcu     120
acaguggauc cuucaucuca caugagcuac aguggauccu ucaucucaca ugagcuacag     180
uggauccuuc aucucacaug agcuacagug gauccuucau cuca                      224

<210> SEQ ID NO 19
<211> LENGTH: 156
<212> TYPE: RNA
<213> ORGANISM: Artificial Sequence
<220> FEATURE:
<223> OTHER INFORMATION: RNA sequence

<400> SEQUENCE: 19
uccaugagcu acaguggauc cuucaucuca agagcuacag ugcuuacucu cauccaugag      60
cuacagugga uccuucaucu caagagcuac agugcuuacu cucauccaug agcuacagug     120
gauccuucau cucaagagcu acagugcuuc aucuca                               156

<210> SEQ ID NO 20
<211> LENGTH: 180
<212> TYPE: RNA
<213> ORGANISM: Artificial Sequence
<220> FEATURE:
<223> OTHER INFORMATION: RNA sequence

<400> SEQUENCE: 20
cauaagccac augcaucuca cugcuccgug cccuaccuca ucucucauaa gccacaugca      60
ucucacugcu ccgugcccua ccucaucucu cauaagccac augcaucuca cugcuccgug     120
cccuaccuca ucucucauaa gccacaugca ucucacugcu ccgugcccua ccucaucucu     180

<210> SEQ ID NO 21
<211> LENGTH: 192
<212> TYPE: RNA
<213> ORGANISM: Artificial Sequence
<220> FEATURE:
<223> OTHER INFORMATION: RNA sequence

<400> SEQUENCE: 21
cugcuccgug cccuaccuca ucucuuauga gcuguagguc ucaucucucu gcuccgugcc      60
cuaccucauc ucuuaugagc uguaggucuc aucucucugc uccgugcccu accucaucuc    120
uuaugagcug uaggucucau cucucugcuc cgugcccuac cucaucucuu augagcugua    180
ggucucaucu cu                                                         192

<210> SEQ ID NO 22
<211> LENGTH: 150
<212> TYPE: RNA
<213> ORGANISM: Artificial Sequence
<220> FEATURE:
<223> OTHER INFORMATION: RNA sequence

<400> SEQUENCE: 22
cugcuccgug cccuaccuca ucucuuccau gagcuguagg ucucaucucu cugcuccgug      60
```

```
cccuaccuca ucucuuccau gagcuguagg ucucaucucu cugcuccgug cccuaccuca      120
ucucuuccau gagcuguagg ucucaucucu                                       150

<210> SEQ ID NO 23
<211> LENGTH: 200
<212> TYPE: RNA
<213> ORGANISM: Artificial Sequence
<220> FEATURE:
<223> OTHER INFORMATION: RNA sequence

<400> SEQUENCE: 23
cuucugagcu guaggucuca ucucucagcu ccgugcccua ccucaucucu cuucugagcu       60
guaggucuca ucucucagcu ccgugcccua ccucaucucu cuucugagcu guaggucuca      120
ucucucagcu ccgugcccua ccucaucucu cuucugagcu guaggucuca ucucucagcu      180
ccgugcccua ccucaucucu                                                  200

<210> SEQ ID NO 24
<211> LENGTH: 255
<212> TYPE: RNA
<213> ORGANISM: Artificial Sequence
<220> FEATURE:
<223> OTHER INFORMATION: RNA sequence

<400> SEQUENCE: 24
cucaugagcu guaggucuca ucucucgagc uccgugcccu accucaucuc ucucaugagc       60
uguaggucuc aucucucgag cuccgugccc uaccucaucu cucucaugag cuguaggucu      120
caucucucga gcuccgugcc cuaccucauc ucucaugaga gcuguagguc ucaucucucg      180
agcuccgugc ccuaccucau cucucaugag cuguagguc ucaucucuc gagcuccgug       240 cccuaccuca ucucu                                                       255

<210> SEQ ID NO 25
<211> LENGTH: 21
<212> TYPE: RNA
<213> ORGANISM: Artificial Sequence
<220> FEATURE:
<223> OTHER INFORMATION: miR-143

<400> SEQUENCE: 25
ugagaugaag cacuguagcu c                                                 21

<210> SEQ ID NO 26
<211> LENGTH: 23
<212> TYPE: DNA
<213> ORGANISM: Artificial Sequence
<220> FEATURE:
<223> OTHER INFORMATION: Primer - human M6PR mRNA, sense

<400> SEQUENCE: 26
gagctacgct catcaccttt ctc                                               23

<210> SEQ ID NO 27
<211> LENGTH: 21
<212> TYPE: DNA
<213> ORGANISM: Artificial Sequence
<220> FEATURE:
<223> OTHER INFORMATION: Primer - human M6PR mRNA, anisense

<400> SEQUENCE: 27
tggtgtacca ccggaagttg t                                                 21
```

```
<210> SEQ ID NO 28
<211> LENGTH: 24
<212> TYPE: DNA
<213> ORGANISM: Artificial Sequence
<220> FEATURE:
<223> OTHER INFORMATION: Primer - mouse M6PR mRNA, sense

<400> SEQUENCE: 28
cacactgatt accttcctct gtga                                          24

<210> SEQ ID NO 29
<211> LENGTH: 22
<212> TYPE: DNA
<213> ORGANISM: Artificial Sequence
<220> FEATURE:
<223> OTHER INFORMATION: Primer - mouse M6PR mRNA, antisense

<400> SEQUENCE: 29
ggtgtaccac cggaagttgt ag                                            22

<210> SEQ ID NO 30
<211> LENGTH: 20
<212> TYPE: DNA
<213> ORGANISM: Artificial Sequence
<220> FEATURE:
<223> OTHER INFORMATION: common probe

<400> SEQUENCE: 30
atatcaggaa gaggacaact                                               20

<210> SEQ ID NO 31
<211> LENGTH: 1304
<212> TYPE: DNA
<213> ORGANISM: Artificial Sequence
<220> FEATURE:
<223> OTHER INFORMATION: M6PR 3' UTR fragment

<400> SEQUENCE: 31
ctccgtggtg cctacagaag aaggtggagc catggacagc caagcacctc caaccaaata     60
agacttcagc tcgatgatgc gtctgtcatt ttgcctttaa caaaactgct tcaaagggaa    120
gagtttctgt aatgggggag aggatggggg aggtgggcac cactccttca tgatcgttta    180
cagtcaatgg aacaaggtgt tgcttgaatc ggccaagggc ggtacttcg tgcccagggg    240 tttgccccaa gtcctcactt acgatcatag ctgctgtgtg cttccaacag gtgcccaagc    300
cacatgcatc tcacaacaga gggctgtgtt tgaaaaaaac ccttgctgct ttagacccta    360
cggggtgacc atttatattt ttagcattgt aattctctcc cctatttatt gactttgaca    420
attactactc aggtttgcga aaaaggaaaa acaaaaacaa aaacaaaacc agtttctttt    480
gccagcaagg gcataaggtg aagctggccg tctgccggag ccgttgtcca tggctcctga    540
actggtcctt gatgcacact tagtgagctg cagtattcta ttcttcgctt tgcattttgt    600
gagggcacac acacatgcac aggtccccga gtgcctaggt ttgggaaggc ccacctgctc    660
cgtgccctac ctcatctctg tagttgcagc tctttgcacg aatccctctg ggtgttgctc    720
ttgccagctg gtgactccca gcagctcacc caggcgggcg ttcgcgcaca cggtggagtg    780
gaggctcttg ggaggagct gcgcttcagg tttgagctgt aggtctcatc tcttcagggt    840
ctcatagtgc cacctttact gtgctttttg cttttttttt tttttttttt aaggggggaaa    900 atgtttatca cccattcgac ctataagaag cctaatttg cacagggtga cttattacag    960
acaccgtgaa acgcggtggg ccagtgttgg tgtagggcca gtgttggtgt aggggctgtg   1020
```

```
ctagggcagt gtcccaggat ggaagggcag gcccagtcca ctggctgtgg attctttct    1080 tgatgtgttc agtgacttgt cacattatag agttgtatat aggtggcatt tacatacca    1140 aaagcaaagt accccgcaga atttcttggt ttatgcctga ttttgctagc ttatttgatt   1200
tcacattgag tgtatttta aaaattgatt tttctcttca ttttaatca acttgactgt     1260 aatatgaagt attcaatttc aataaagata aattattaac tagg                    1304
```

<210> SEQ ID NO 32
<211> LENGTH: 1721
<212> TYPE: DNA
<213> ORGANISM: Artificial Sequence
<220> FEATURE:
<223> OTHER INFORMATION: last exon of murine M6PR with the three
      binding sites

<400> SEQUENCE: 32

```
gtcagcaagg aggaggagac agatgagaat gagacagaat ggctgatgga agagatccag   60
gtgccagccc caagactagg caaggacggg caagaaaatg ccatatcac caccaaggcg   120 gtgaaagcag aagctctctc gtccctgcat ggggacgacc aggacagtga ggatgaggtc   180
ctgaccgttc cagaggtgaa agttcactca ggccgaggag cggaggtgga aagctcacag   240
cccctgagaa acccacagcg caaggtcctg aaggaaaggg agggtgagag gctggggctg   300
gtccgaggtg agaaggccag aaaagggaag ttcagacccg gacagcgcaa gccaacagcc   360
cctgccaagc tggtgtcctt ccatgatgac agcgacgaag acctcttaca catctaactc   420
cgtggtgcct acagaagaag gtggagccat ggacagccaa gcacctccaa ccaaataaga   480
cttcagctcg atgatgcgtc tgtcattttg cctttaacaa aactgcttca aagggaagag   540
tttctgtaat gggggagagg atgggggagg tgggcaccac tccttcatga tcgtttacag   600
tcaatggaac aaggtgttgc ttgaatcggc caaagggcgg tacttcgtgc ccaggggttt   660
gccccaagtc ctcacttacg atcatagctg ctgtgtgctt ccaacaggtg cccaagccac   720
atgcatctca aacagaggg ctgtgtttga aaaaaccct tgctgcttta gaccctacgg     780
ggtgaccatt tatattta gcattgtaat tctctcccct atttattgac tttgacaatt     840
actactcagg tttgcgaaaa aggaaaaaca aaaacaaaaa caaaaccagt ttcttttgcc    900
agcaagggca taaggtgaag ctggccgtct gccggagccg ttgtccatgg ctcctgaact   960
ggtccttgat gcacacttag tgagctgcag tattctattc ttcgctttgc attttgtgag  1020
ggcacacaca catgcacagg tccccgagtg cctaggtttg ggaaggccca cctgctccgt  1080
gccctacctc atctctgtag ttgcagctct ttgcacgaat ccctctgggt gttgctcttg  1140
ccagctggtg actcccagca gctcacccag gcgggcgttc gcgcacacgg tggagtggag  1200
gctcttgggg aggagctgcg cttcaggttt gagctgtagg tctcatctct tcagggtctc  1260
atagtgccac ctttactgtg ctttttgctt tttttttttt ttttttaag ggggaaaatg    1320 tttatcaccc attcgaccta taagaagcct taatttgcac agggtgactt attacagaca  1380
ccgtgaaacg cggtgggcca gtgttggtgt agggccagtg ttggtgtagg ggctgtgcta  1440
gggcagtgtc ccaggatgga agggcaggcc cagtccactg gctgtggatt cttttcttga  1500
tgtgttcagt gacttgtcac attatagagt tgtatatagg tggcatttac ataccccaaa  1560
gcaaagtacc ccgcagaatt tcttggtttta tgcctgattt tgctagctta tttgatttca  1620
cattgagtgt attttaaaaa attgattttt ctcttcattt ttaatcaact tgactgtaat  1680
atgaagtatt caatttcaat aaagataaat tattaactag g                      1721
```

<210> SEQ ID NO 33
<211> LENGTH: 55
<212> TYPE: DNA
<213> ORGANISM: Artificial Sequence
<220> FEATURE:
<223> OTHER INFORMATION: DNA related to miR143 - sense

<400> SEQUENCE: 33
ctagagagct acagacgtca tctcacgatg agctacagtg gatccttcat ctcat    55

<210> SEQ ID NO 34
<211> LENGTH: 55
<212> TYPE: DNA
<213> ORGANISM: Artificial Sequence
<220> FEATURE:
<223> OTHER INFORMATION: DNA related to miR143 - antisense

<400> SEQUENCE: 34
ctagatgaga tgaaggatcc actgtagctc atcgtgagat gacgtctgta gctct    55

<210> SEQ ID NO 35
<211> LENGTH: 6420
<212> TYPE: DNA
<213> ORGANISM: Artificial Sequence
<220> FEATURE:
<223> OTHER INFORMATION: full 3'UTR human M6PR

<400> SEQUENCE: 35
ctccgcagtg cctgcagggg agcacggagc cgcgggacag ccaagcacct ccaaccaaat      60
aagacttcca ctcgatgatg cttctataat tttgccttta acagaaactt tcaaaaggga     120 agagttttg tgatggggga gagggtgaag gaggtcaggc cccactcctt cctgattgtt      180
tacagtcatt ggaataaggc atggctcaga tcggccacag ggcggtacct tgtgcccagg     240
gttttgcccc aagtcctcat ttaaaagcat aaggccggac gcatctcaaa acagagggct     300
gcattcgaag aaacccttgc tgctttagtc ccgatagggt atttgacccc gatatatttt     360
agcattttaa ttctctcccc ctatttattg actttgacaa ttactcaggt ttgagaaaaa     420
ggaaaaaaaa acagccaccg tttcttcctg ccagcagggg tgtgatgtac cagtttgtcc     480
atcttgagat ggtgaggctg tcagtgtatg gggcagcttc cggcgggatg ttgaactggt     540
cattaatgtg tcccctgagt tggagctcat tctgtctctt ttctcttttg ctttctgttt     600
cttaagggca cacacgtg cgtgcgagca cacacacaca tacgtgcaca gggtccccga       660
gtgcctaggt tttggagagt ttgcctgttc tatgccttta gtcaggaatg gctgcacctt     720
tttgcatgat atcttcaagc ctgggcgtac agagcacatt tgtcagtatt tttgccggct     780
ggtgaattca acaacctgc ccaaagattg atttgtgtgt ttgtgtgtgt gtgtgtgtgt      840
gtgtgtgtgt gtgtgagtgg agttgaggtg tcagagaaaa tgaatttttt ccagatttgg     900
ggtataggtc tcatctcttc aggttctcat gataccacct ttactgtgct tattttttta     960
agaaaaaagt gttgatcaac cattcgacct ataagaagcc ttaatttgca cagtgtgtga    1020
cttacagaaa ctgcatgaaa aatcatgggc cagagcctcg gccctagcat tgcacttggc    1080
ctcatgctgg agggaggctg ggcgggtaca gcgcggagga ggagggaggc caggcgggca    1140
tggcgtggag gaggagggag gccgggcggt cacagcatgg aggaggaggg aggcgctgct    1200
ggtgttctta ttctggcggc agcgcctttc ctgccatgtt tagtgaatga ctttctcgc     1260 attgtagaat tgtatataga ctctggtgtt ctattgctga gaagcaaacc gccctgcagc    1320
atccctcagc ctgtaccggt ttggctggct tgtttgattt caacatgagt gtattttta    1380

```
aaattgattt ttctcttcat ttttttttca atcaacttta ctgtaatata aagtattcaa    1440
caatttcaat aaaagataaa ttattaattg ggtgttacca ttttttcctt gatagtgaga    1500
cgttcccgag cgagttaccc atctgcctgc ctgtcttttc tttctgttaa gtgactgaat    1560
ttgggtttta actctggtgt tctcgttgac cctttatgag gcagcacttt cattttctc    1620 cagagtctcc tggtcgtagg tgttaacttt gggtccaatc tgccttccct tggctctttc    1680
tagatccgat ttcttacct tctccaggcc aacctcgggg tgtggtcctg ttcatcaaaa    1740
caatgaacat ggagtttaga gtccagtgag tcaataaagc ttttttttgt gcaacctgat    1800
ctaacatgga gatgttttct cttgagtaaa ctcactgagt tttccatctt aaattactca    1860
gcagtgactg agagctacct gcatggaagc aggaagttac tccagtgtta taaacaaact    1920
tcttagactc aacatcctat tctccatccc tttttttttc ctgtagagtc caaaacctc    1980 aaccgtctca tttttaaatt atccaattgg agttaccttt ttaaaaagt tattcttaag    2040 gactttccaa tacctctcct gaggaagaca tgtcaggtct tctaaaagtt tacattatga    2100
ccaaagaaag atgctggtcc tcaggcattc tacccagggg gctgttctcc aggccattcc    2160
cacctcctgc taagaccatg gggagccctc tctgtaagga ggggcatatg cagggacctg    2220
cccatcccct tggtaagctg gatggcaaaa aggcatgttg tctgcaccac tggctgcctg    2280
ctaatgtcgc tgtcagtggg gaaggagaag tgacaacacg tttgagtgca tttgctttga    2340
ctcttagaaa cccaagcctc tgaaaaaaga gtaactactt gccagctgtt gttacagatg    2400
atatttttag gaaacatcc cgtgacagca aatcagaatt ggactctttt tcagagaaat    2460
gattttattg atggagtaca acctgggtat ttagcttcct ttcaacaaaa ttttttgtgc    2520
ccctttcttg agactgtcca tgaatgacag agacatagaa taagaactgg ggtgctaaag    2580
atggaatagg caaaccccac accaaggaaa tccacagtga agtggaaatc tggttcttat    2640
gaacatttta agagcatctg aagcctgtac ttcaccaacc ctaaaataat acgtaacacg    2700
agatgattcc tcaggaagga acatatagac atacagacag gagacaacat atagacatta    2760
gaacttacag gacaaagaac tcttttttccc tgaatcattt gagatgaagt ttcttcccat    2820
caccaggcat tcctacaaac aaggaccttc acacgactaa gatgccacct ggtgattaaa    2880
gaacactttg ggctggtccg atccattgta caagttaaag cactgatggg tacacaggtc    2940 ttaccctgt tggcgatcgg gtcacaagga gccagtgtgt tgtcaccag gaggttgtat    3000 ggacgagact ggatttctgg aaatatcctt tactgactct gaagaatccc atggctcagg    3060
gaggtacact catgtccttt cttacttctc cggttccact ctgttgacta gtagttggcc    3120
tcttgagcca tacttgctgt cagttctgga cattgttctg tgagaatggg gtcaacgggc    3180
agtcgtggtg caggtgagct tgtgtgcaag gcggcaagat agccacattg agttggggac    3240
agtatggcct gggggtgttg gataggtaag gcagaagcaa gcccagaact tggagcctgt    3300
tgtgactgtc acagtaagga gtttgaagtc ctgaaagcag ttgagagctg taggagggcc    3360
agattgggct tttgagcaag atagtctaga tgaaagtaaa gagatggaga cgcttcagca    3420
accagatggg aggttgggca tgggagctgt ggctgtgctg agctgagaag cctcagactg    3480
cctgcgaggc tctctctggg aggaagtcag gtctttcttt ccttcgtttc cttcctttca    3540
ttcctttcct ttccttcctt tttcctcttt cttttctttcc ttttctctct ctctcttttt    3600 cttttctctct ttctttcgag atggagtctc gctctgttgc caggctggag tgcagtggca    3660
tgatctcggc tcactgcaat ctctgcctcc cgggttcaag ggattctcct gcctcagcct    3720
```

```
ccctagtagc tgggattaaa ggcacgcact gccacgcccg gctaattttt gtattttttaa    3780 tagcgacagg gtttcaccgt gttggccagg atggtctcga tctcctgacc tcatgatcca    3840
cctgcctcgg cctccgaaag tgctgggatt acaggcgtga gccaccgtgc ccagccaggt    3900
ctttttctta aagagggaca gactgaaggt aggctgtgaa tggtcagtta tttgtatttc    3960 tttaccttt  atgctatctt gtagtttgac cagtttgcaa aacaaattga ataaaaagta    4020
attgataatg ttgttttgat gctcagtgtt tgagggaaac acaatctagt gaatggggtt    4080
attggttgtc acacctggga gagtgaaaat gaggggctca caacccaggt gaggtcatct    4140
ggtgccactc agccccatcc cagagaaagc agccttggga tgctggcctc ggtgacaacc    4200
aagaagtgat ggtgggttgc tagagacagg gtggagcaca gagccctgga aggaagcagg    4260
aagtcaggtt caagaaagga cttgtgacct cacccttggc ttcagggttt tattttttctt    4320 tcttttaaaa cattttgaga caacatgtag acattcaaac ttacagaaca aagaactatt    4380
ttttccctga atcatttgag actaagttcc ctcctatcac cagacatttc tacaaatgag    4440
gaccttcaca ggactaaggt gccaccatca gaaccacaat atgtggggac ggtactgcca    4500
gctaagcctt agtgctgttt cggtgttgac agctgtcaca atgatgccct tttcagtaga    4560
ggagcctgtg atggtcacgt gttgcaggtg atcattgtgc catttggttt acttctgtct    4620
ggaaagtttc tccttttctgt aacctccatg accttgacac atgaggtcac tcttctcacc    4680
cgccccacct ctgggagggt gcctgatttg ccctgcccca cccagcggct ttaggactca    4740
gctcttcagg aacaattagg gagagggccc ttgggtctaa ctgcaaaatc atacttgaac    4800
tagaaaatcc cgttggcata ggtatggatt gtcatataga aacattttc gcagtgtgcc    4860 ccgtggaaca cttgttctgt atgttgttaa cagatgtttt gcaaaaaatg aaaaggacct    4920
gagctctaat aagtttggga aatgctgaat tgaagtgaaa cagcttttct tggtgtgaga    4980
cctttcagag tctttaaagg agagttgctg accacacgtg aaatcacaat agaaaatggc    5040
cagcaggcct ccaggtaggc agcaattcct agacatttgc ctgtgttccc tgggggagct    5100
ggtggcctgt gaccatccac tgggaaattc ccttctgtgg cgaggttctg ttgttttcca    5160
gaggctccca cggagcatgc tgggtggggtg gtctgtatga gaccacaccg ttgatgagca    5220
gtgaggccca acaggtata  tcaaaaaatg ctcagcatcg ctgatcatca gggaaatgca    5280
catcataaac acagtgagac gttgcctcac acctgccaga atggctactg tcagacgaaa    5340
gacaacaagt gtgggtgagg atgtggagaa aagcgaacac ttgtccacct ttggtgagaa    5400
tgtaaattgg tatagccatt atggaaaaca ggaagttcct gaaaaaatta agaacagcta    5460
ccaggaatcc cacatctggg tgtatatcca aaagaaatga agtcagtacc ttgaagagat    5520
ctctgcagcc cctgttcatt gcagcattat tcacaatagc caagataggg aaaaagcctc    5580
agtgtctact gacaaataaa gatggatcaa gaaaatgcat gtatgtatac acacacacag    5640
tggaatacca agtcttgcag aagaaggaaa tcctgtcatt tgtgacaaca tggatgagct    5700
gagagaacat tatgctaagt gaaataagcc agacacagaa agaaaaatac cagatgatct    5760
cacttatatg tggaatctaa aaaggttgga ctcagaagca gagagtggaa tggtggttac    5820
caaaggccag agggtgcagg aagtgagcag atgttggtga agggtgcag  aggttcagct    5880 atgcaacatg aatgaattct ggagatccac tgtgcagcat ggtgactatg atactgcttt    5940
gtgtatttaa aattttcaga gagtagatct tgtgttcttt cccctctcca aataaaagga    6000
aattatttga ggtgatggat atgtttaact agccttgactg gggcaatgat tttgtaatga    6060
taagtatctc aaaacatcat gttgtacaac ataagtatac aattgaccct tgaacaatac    6120
```

```
aggtttgaac tctgtgggtc cacttacatg cggttttttt tttctgtaaa agttacaccc    6180
gatgcgtcag ccccttcttc tacctcttcc acctctggca cccttggcac agcaagacca    6240
accccccact tcctcctcct cctcctcagc ctactcaggg taaagacaag gatgaagacc    6300
tttatgatga tccacttcca cttaatatat aataaatata ttttctcctc atgattttct    6360
taaaactttt tctgtatttt attgtaagaa tacagtatat aatacataca acatcgaaaa    6420
```

<210> SEQ ID NO 36
<211> LENGTH: 6831
<212> TYPE: DNA
<213> ORGANISM: Artificial Sequence
<220> FEATURE:
<223> OTHER INFORMATION: Last exon of human M6PR

<400> SEQUENCE: 36

```
gtgaataagg aagaagagac agatgagaat gaaacagagt ggctgatgga agagatccag      60
ctgcctcctc cacggcaggg aaaggaaggg caggagaacg ccatattac caccaagtca     120 gtgaaagccc tcagctccct gcatggggat gaccaggaca gtgaggatga ggttctgacc     180
atcccagagg tgaaagttca ctcgggcagg ggagctgggg cagagagctc ccacccagtg     240
agaaacgcac agagcaatgc ccttcaggag cgtgaggacg atagggtggg gctggtcagg     300
ggtgagaagg cgaggaaagg gaagtccagc tctgcacagc agaagacagt gagctccacc     360
aagctggtgt ccttccatga cgacagcgac gaggacctct acacatctg actccgcagt     420 gcctgcaggg gagcacggag ccgcgggaca gccaagcacc tccaaccaaa taagacttcc     480
actcgatgat gcttctataa ttttgccttt aacagaaact ttcaaaaggg aagagttttt     540
gtgatggggg agagggtgaa ggaggtcagg ccccactcct tcctgattgt ttacagtcat     600
tggaataagg catggctcag atcggccaca gggcggtacc ttgtgcccag ggttttgccc     660
caagtcctca tttaaaagca taaggccgga cgcatctcaa aacagagggc tgcattcgaa     720
gaaacccttg ctgctttagt cccgataggg tatttgaccc cgatatattt tagcatttta     780
attctctccc cctatttatt gactttgaca attactcagg tttgagaaaa aggaaaaaaa     840
aacagccacc gtttcttcct gccagcaggg gtgtgatgta ccagtttgtc catcttgaga     900
tggtgaggct gtcagtgtat ggggcagctt ccggcgggat gttgaactgg tcattaatgt     960 gtccccctgag ttggagctca ttctgtctct tttctctttt gctttctgtt tcttaagggc    1020
acacacacgt gcgtgcgagc acacacacac atacgtgcac agggtccccg agtgcctagg    1080
ttttggagag tttgcctgtt ctatgccttt agtcaggaat ggctgcacct ttttgcatga    1140
tatcttcaag cctgggcgta cagagcacat ttgtcagtat ttttgccggc tggtgaattc    1200
aaacaacctg cccaaagatt gatttgtgtg tttgtgtgtg tgtgtgtgtg tgtgtgtgtg    1260
tgtgtgagtg gagttgaggt gtcagagaaa atgaattttt tccagatttg gggtataggt    1320
ctcatctctt caggttctca tgataccacc tttactgtgc ttattttttt aagaaaaaag    1380
tgttgatcaa ccattcgacc tataagaagc cttaatttgc acagtgtgtg acttacagaa    1440
actgcatgaa aaatcatggg ccagagcctc ggccctagca ttgcacttgg cctcatgctg    1500
gagggaggct gggcgggtac agcgcggagg aggagggagg ccaggcgggc atggcgtgga    1560
ggaggaggga ggccgggcgg tcacagcatg gaggaggagg gaggcgctgc tggtgttctt    1620
attctggcgg cagcgccttt cctgccatgt ttagtgaatg acttttctcg cattgtagaa    1680
ttgtatatag actctggtgt tctattgctg agaagcaaac cgccctgcag catccctcag    1740
```

```
cctgtaccgg tttggctggc ttgtttgatt tcaacatgag tgtattttt  aaaattgatt   1800
tttctcttca ttttttttc  aatcaacttt actgtaatat aaagtattca acaatttcaa   1860
taaaagataa attattaatt gggtgttacc attttttcct tgatagtgag acgttcccga   1920
gcgagttacc catctgcctg cctgtctttt ctttctgtta agtgactgaa tttgggtttt   1980
aactctggtg ttctcgttga ccctttatga ggcagcactt tcattttct  ccagagtctc   2040
ctggtcgtag gtgttaactt tgggtccaat ctgccttccc ttggctcttt ctagatccga   2100
tttctttacc ttctccaggc caacctcggg gtgtggtcct gttcatcaaa acaatgaaca   2160
tggagtttag agtccagtga gtcaataaag cttttttg   tgcaacctga tctaacatgg   2220
agatgttttc tcttgagtaa actcactgag ttttccatct taaattactc agcagtgact   2280
gagagctacc tgcatggaag caggaagtta ctccagtgtt ataaacaaac ttcttagact   2340
caacatccta ttctccatcc cttttttttt cctgtagagt ccaaaaacct caaccgtctc   2400
atttttaaat tatccaattg gagttaccct tttaaaaaag ttattcttaa ggactttcca   2460
atacctctcc tgaggaagac atgtcaggtc ttctaaaagt ttacattatg accaaagaaa   2520
gatgctggtc ctcaggcatt ctacccaggg ggctgttctc caggccattc ccacctcctg   2580
ctaagaccat ggggagccct ctctgtaagg aggggcatat gcaggacct  gcccatcccc   2640
ttggtaagct ggatggcaaa aaggcatgtt gtctgcacca ctggctgcct gctaatgtcg   2700
ctgtcagtgg ggaaggagaa gtgacaacac gtttgagtgc atttgctttg actcttagaa   2760
acccaagcct ctgaaaaaag agtaactact tgccagctgt tgttacagat gatattttta   2820
ggaaaacatc ccgtgacagc aaatcagaat tggactcttt ttcagagaaa tgattttatt   2880
gatggagtac aacctgggta tttagcttcc tttcaacaaa attttttgtg cccctttctt   2940
gagactgtcc atgaatgaca gagacataga ataagaactg gggtgctaaa gatggaatag   3000
gcaaaccccca caccaaggaa atccacagtg aagtggaaat ctggttctta tgaacatttt   3060
aagagcatct gaagcctgta cttcaccaac cctaaaataa tacgtaacac gagatgattc   3120
ctcaggaagg aacatataga catacagaca ggagacaaca tatagacatt agaacttaca   3180
ggacaaagaa ctctttttcc ctgaatcatt tgagatgaag tttcttccca tcaccaggca   3240
ttcctacaaa caaggacctt cacacgacta agatgccacc tggtgattaa agaacacttt   3300
gggctggtcc gatccattgt acaagttaaa gcactgatgg gtacacaggt cttacccctg   3360
ttggcgatcg ggtcacaagg agccagtgtg tgtgtcacca ggaggttgta tggacgagac   3420
tggatttctg gaaatatcct ttactgactc tgaagaatcc catggctcag ggaggtacac   3480
tcatgtcctt tcttacttct ccggttccac tctgttgact agtagttggc ctcttgagcc   3540
atacttgctg tcagttctgg acattgttct gtgagaatgg ggtcaacggg cagtcgtggt   3600
gcaggtgagc ttgtgtgcaa ggcggcaaga tagccacatt gagttgggga cagtatggcc   3660
tgggggtgtt ggataggtaa ggcagaagca agcccagaac ttggagcctg ttgtgactgt   3720
cacagtaagg agtttgaagt cctgaaagca gttgagagct gtaggagggc cagattgggc   3780
ttttgagcaa gatagtctag atgaaagtaa agagatggag acgcttcagc aaccagatgg   3840
gaggttgggc atgggagctg tggctgtgct gagctgagaa gcctcagact gcctgcgagg   3900
ctctctctgg gaggaagtca ggtctttctt tccttcgttt ccttcctttc attcctttcc   3960
tttccttcct ttttcctctt tctttctttc cttttctctc tctctctttt tctttctctc   4020
tttctttcga gatggagtct cgctctgttg ccaggctgga gtgcagtggc atgatctcgg   4080
ctcactgcaa tctctgcctc ccgggttcaa gggattctcc tgcctcagcc tccctagtag   4140
```

```
ctgggattaa aggcacgcac tgccacgccc ggctaatttt tgtatttttta atagcgacag   4200 ggtttcaccg tgttggccag gatggtctcg atctcctgac ctcatgatcc acctgcctcg   4260 gcctcccgaaa gtgctgggat tacaggcgtg agccaccgtg cccagccagg tctttttctt   4320
aaagagggac agactgaagg taggctgtga atggtcagtt atttgtattt ctttacccttt   4380 tatgctatct tgtagtttga ccagtttgca aaacaaattg aataaaaagt aattgataat   4440
gttgttttga tgctcagtgt ttgagggaaa cacaatctag tgaatggggt tattggttgt   4500
cacacctggg agagtgaaaa tgaggggctc acaacccagg tgaggtcatc tggtgccact   4560
cagccccatc ccagagaaag cagccttggg atgctggcct cggtgacaac caagaagtga   4620
tggtgggttg ctagagacag ggtggagcac agagccctgg aaggaagcag gaagtcaggt   4680
tcaagaaagg acttgtgacc tcacccttgg cttcagggtt ttattttttct ttcttttaaa   4740 acatttgag acaacatgta gacattcaaa cttacagaac aaagaactat ttttccctg   4800 aatcatttga gactaagttc cctcctatca ccagacattt ctacaaatga ggaccttcac   4860
aggactaagg tgccaccatc agaaccacaa tatgtgggga cggtactgcc agctaagcct   4920
tagtgctgtt tcggtgttga cagctgtcac aatgatgccc ttttcagtag aggagcctgt   4980
gatggtcacg tgttgcaggt gatcattgtg ccatttggtt tacttctgtc tggaaagttt   5040 ctccttttctg taacctccat gaccttgaca catgaggtca ctcttctcac ccgccccacc   5100
tctgggaggg tgcctgattt gccctgcccc acccagcggc tttaggactc agctcttcag   5160
gaacaattag ggagagggcc cttgggtcta actgcaaaat catacttgaa ctagaaaatc   5220
ccgttggcat aggtatggat tgtcatatag aaacattttt cgcagtgtgc cccgtggaac   5280
acttgttctg tatgttgtta acagatgttt tgcaaaaaat gaaaaggacc tgagctctaa   5340
taagtttggg aaatgctgaa ttgaagtgaa acagcttttc ttggtgtgag acctttcaga   5400
gtctttaaag gagagttgct gaccacacgt gaaatcacaa tagaaaatgg ccagcaggcc   5460
tccaggtagg cagcaattcc tagacatttg cctgtgttcc ctgggggagc tggtggcctg   5520
tgaccatcca ctgggaaatt cccttctgtg gcgaggttct gttgttttcc agaggctccc   5580
acggagcatg ctgggtgggt ggtctgtatg agaccacacc gttgatgagc agtgaggccc   5640
aaacaggtat atcaaaaaat gctcagcatc gctgatcatc agggaaatgc acatcataaa   5700
cacagtgaga cgttgcctca cacctgccag aatggctact gtcagacgaa agacaacaag   5760
tgtgggtgag gatgtggaga aaagcgaaca cttgtccacc tttggtgaga atgtaaattg   5820
gtatagccat tatggaaaac aggaagttcc tgaaaaaatt aagaacagct accaggaatc   5880
ccacatctgg gtgtatatcc aaaagaaatg aagtcagtac cttgaagaga tctctgcagc   5940
ccctgttcat tgcagcatta ttcacaatag ccaagatagg gaaaaagcct cagtgtctac   6000
tgacaaataa agatggatca agaaaatgca tgtatgtata cacacacaca gtggaatacc   6060
aagtcttgca gaagaaggaa atcctgtcat ttgtgacaac atggatgagc tgagagaaca   6120
ttatgctaag tgaaataagc cagacacaga aagaaaaata ccagatgatc tcacttatat   6180
gtggaatcta aaaaggttgg actcagaagc agagagtgga atggtggtta ccaaaggcca   6240
gagggtgcag gaagtgagca gatgttggtg aaagggtgca gaggttcagc tatgcaacat   6300
gaatgaattc tggagatcca ctgtgcagca tggtgactat gatactgctt tgtgtattta   6360 aaatttcag agagtagatc ttgtgttctt tcccctctcc aaataaaagg aaattatttg   6420
aggtgatgga tatgttttaac tagcttgact ggggcaatga ttttgtaatg ataagtatct   6480
```

-continued

```
caaaacatca tgttgtacaa cataagtata caattgaccc ttgaacaata caggtttgaa      6540
ctctgtgggt ccacttacat gcggttttt ttttctgtaa aagttacacc cgatgcgtca       6600 gcccttctt ctacctcttc cacctctggc acccttggca cagcaagacc aaccccccac       6660
ttcctcctcc tcctcctcag cctactcagg gtaaagacaa ggatgaagac ctttatgatg      6720
atccacttcc acttaatata taataaatat attttctcct catgattttc ttaaaactt       6780 ttctgtattt tattgtaaga atacagtata taatacatac aacatcgaaa a               6831
```

<210> SEQ ID NO 37
<211> LENGTH: 23
<212> TYPE: RNA
<213> ORGANISM: Artificial Sequence
<220> FEATURE:
<223> OTHER INFORMATION: RNA core

<400> SEQUENCE: 37

```
uuugggguau aggucucauc ucu                                              23
```

<210> SEQ ID NO 38
<211> LENGTH: 23
<212> TYPE: RNA
<213> ORGANISM: Artificial Sequence
<220> FEATURE:
<223> OTHER INFORMATION: RNA core

<400> SEQUENCE: 38

```
gcauaaggcc ggacgcaucu caa                                              23
```

<210> SEQ ID NO 39
<211> LENGTH: 110
<212> TYPE: RNA
<213> ORGANISM: Artificial Sequence
<220> FEATURE:
<223> OTHER INFORMATION: RNA sequence

<400> SEQUENCE: 39

```
cuagagagcu acagacguca ucucacgaug agcuacagug gauccuucau cucaucuaga      60
gagcuacaga cgucaucuca cgaugagcua caguggaucc uucaucucau                 110
```

<210> SEQ ID NO 40
<211> LENGTH: 55
<212> TYPE: RNA
<213> ORGANISM: Artificial Sequence
<220> FEATURE:
<223> OTHER INFORMATION: RNA sequence

<400> SEQUENCE: 40

```
cuagagagcu acagacguca ucucacgaug agcuacagug gauccuucau cucau           55
```

<210> SEQ ID NO 41
<211> LENGTH: 18
<212> TYPE: RNA
<213> ORGANISM: Artificial Sequence
<220> FEATURE:
<223> OTHER INFORMATION: Mut1

<400> SEQUENCE: 41

```
aagccacaug gccgcgcc                                                    18
```

<210> SEQ ID NO 42
<211> LENGTH: 23
<212> TYPE: RNA
<213> ORGANISM: Artificial Sequence

```
<220> FEATURE:
<223> OTHER INFORMATION: Mut2

<400> SEQUENCE: 42
gcuccgugcc cuacccgccg cgu                                              23

<210> SEQ ID NO 43
<211> LENGTH: 21
<212> TYPE: RNA
<213> ORGANISM: Artificial Sequence
<220> FEATURE:
<223> OTHER INFORMATION: Mut3

<400> SEQUENCE: 43
ugagcuguag guccgccgcg u                                                21

<210> SEQ ID NO 44
<211> LENGTH: 50
<212> TYPE: RNA
<213> ORGANISM: Artificial Sequence
<220> FEATURE:
<223> OTHER INFORMATION: RNA sponge

<400> SEQUENCE: 44
gagcuacaga cgucaucuca cgaugagcua caguggaucc uucaucucau                 50
```